US012582689B2

(12) United States Patent
Wu et al.

(10) Patent No.: US 12,582,689 B2
(45) **Date of Patent: *Mar. 24, 2026**

(54) USE OF TERPENOIDS IN THE TREATMENT OR PREVENTION OF FIBROTIC DISEASES

(71) Applicant: ARJIL BIOTECH HOLDING COMPANY LIMITED, Hsinchu (TW)

(72) Inventors: Yeh-B Wu, Hsinchu (TW); Jir-Mehng Lo, Hsinchu (TW); Hui-Ju Liang, Taipei (TW); Pei-Hsin Lin, Hsinchu County (TW)

(73) Assignee: ARJIL BIOTECH HOLDING COMPANY LIMITED, Hsinchu (TW)

( * ) Notice: Subject to any disclaimer, the term of this patent is extended or adjusted under 35 U.S.C. 154(b) by 440 days.

This patent is subject to a terminal disclaimer.

(21) Appl. No.: 17/926,677

(22) PCT Filed: May 19, 2021

(86) PCT No.: PCT/US2021/033225

§ 371 (c)(1),
(2) Date: Nov. 21, 2022

(87) PCT Pub. No.: WO2021/236811

PCT Pub. Date: Nov. 25, 2021

(65) Prior Publication Data

US 2023/0190850 A1 Jun. 22, 2023

Related U.S. Application Data

(60) Provisional application No. 63/027,029, filed on May 19, 2020.

(51) Int. Cl.

| | |
|---|---|
| ***A61K 36/53*** | (2006.01) |
| ***A61K 31/575*** | (2006.01) |
| ***A61K 36/07*** | (2006.01) |
| ***A61P 1/16*** | (2006.01) |
| ***A61P 9/10*** | (2006.01) |
| ***A61P 11/00*** | (2006.01) |
| ***A61P 13/12*** | (2006.01) |

(52) U.S. Cl.

CPC ............ *A61K 36/53* (2013.01); *A61K 31/575* (2013.01); *A61K 36/07* (2013.01); *A61P 1/16* (2018.01); *A61P 9/10* (2018.01); *A61P 11/00* (2018.01); *A61P 13/12* (2018.01); *A61K 2236/333* (2013.01); *A61K 2236/39* (2013.01)

(58) Field of Classification Search

CPC ...... A61K 36/53; A61K 31/575; A61K 36/07; A61K 2236/333; A61K 2236/39; A61P 11/00; A61P 9/10; A61P 1/16; A61P 13/12

See application file for complete search history.

(56) References Cited

U.S. PATENT DOCUMENTS

| | | | |
|---|---|---|---|
| 8,969,410 | B1 | 3/2015 | Shih et al. |
| 9,801,918 | B2 | 10/2017 | Joshi et al. |
| 2015/0202180 | A1 | 7/2015 | Eriksson et al. |
| 2020/0009110 | A1 | 1/2020 | Wu et al. |

OTHER PUBLICATIONS

Wang et al. (European J. of pharmacology; 812(2017) 9-17).*
Royce et al. (Molecular and Cellular Endocrinology ; 351(2012) 167-175).*
Chen-Yuan (European J. of Pharmacology 819, 15 (2018, 16-29).*
Xiao-Ming et al. (Nature Reviews Nephrology 2014).*
Farrell et al. (Gut and Liver, vol. 6, No. 2, Apr. 2012 ).*
International Search Report, issued in PCT/US2021/033225, PCT/ISA/210, dated Sep. 8, 2021.
Lien et al., "Antibacterial activity of ovatodiolide isolated from Anisomeles indica against Helicobacter pylori", Scientific Reports, Mar. 12, 2019, vol. 9, p. 1-7.
Written Opinion of the International Searching Authority, issued in PCT/US2021/033225, PCT/ISA/237, dated Sep. 8, 2021.

* cited by examiner

*Primary Examiner* — Shirley V Gembeh
(74) *Attorney, Agent, or Firm* — Birch, Stewart, Kolasch & Birch, LLP

(57) ABSTRACT

The present invention relates to a method of preventing or treating a fibrotic condition, comprising administering an effective amount of composition to a subject in need thereof; wherein the composition comprises triterpenes extracted from *Antrodia-camphorate* or *Anisomeles indica.*

4 Claims, 48 Drawing Sheets

Control

Cisplatin (5 mg/Kg)

AR101-DS1 (40 mg/Kg)

AR101-DS1 (20 mg/Kg)

AR101-DS3 (40 mg/Kg)

AR101-DS3 (20 mg/Kg)

AR101-DS4 (40 mg/Kg)

AR101-DS4 (20 mg/Kg)

AR100-DS1 (40 mg/Kg)

AR100-DS1 (20 mg/Kg)

Regimen:

| Group | Treatment | Dose (mg/kg) | Gavaged volume (ml/kg) | Drug conc. (mg/ml) | Route | Frequency | # animals |
|---|---|---|---|---|---|---|---|
| 1 | Vehicle | - | 10 | - | PO | BID | 8 |
| 2 | 50 mg/kg AR100-DS1 | 50 | 10 | 5 | PO | BID | 8 |
| 3 | Naïve | - | - | - | - | - | 3 |
| | | | | | | | |

Data are expressed as mean ± SEM (n = 3-8). p < 0.01 and *p < 0.001, compared with the Vehicle group by Student's t-test.

| Weeks after CCl4 administration | | | | | |
|---|---|---|---|---|---|
| AST | W0 | W2 | W4 | W6 | W8 |
| Vehicle | 123.13± 7.08 | 609.50± 62.65 | 820.38± 95.71 | 1870.63± 204.80 | 7575.00± 539.56 |
| 50 mg/kg AR100-DS1 | 121.50± 5.42 | 593.71± 60.90 | 915.71± 143.58 | 1025.71± 113.17 ** | 3902.86± 359.58 *** |
| Naïve | 113.00± 8.74 | 93.67± 8.67 *** | 123.67± 9.96 *** | 136.67± 13.38 *** | 127.67± 32.67 *** |

Data are expressed as mean ± SEM (n = 3-8). p < 0.01 and *p < 0.001, compared with the Vehicle group by Student's t-test.

| | Weeks after CCl4 administration | | | | |
|---|---|---|---|---|---|
| ALT | W0 | W2 | W4 | W6 | W8 |
| Vehicle | 53.88± 2.51 | 605.13± 101.14 | 1263.63± 215.58 | 2631.25± 338.40 | 7013.33± 504.69 |
| 50 mg/kg AR100-DS1 | 52.63± 2.54 | 686.71± 102.76 | 1800.71± 481.68 | 1407.86± 188.15 ** | 4458.57± 586.22 ** |
| Naïve | 54.67± 8.82 | 45.67± 1.86 *** | 49.67± 0.88 *** | 49.00± 2.31 *** | 55.00± 7.00 *** |

Data are expressed as mean ± SEM (n = 3-8). *p < 0.05 and **p < 0.01, compared with the Vehicle group by Student's t-test.

| | Weeks after CCl4 administration | | | | |
|---|---|---|---|---|---|
| AST/ALT ratio | W0 | W2 | W4 | W6 | W8 |
| Vehicle | 2.31± 0.15 | 1.08± 0.08 | 0.69± 0.04 | 0.74± 0.07 | 1.12± 0.15 |
| 50 mg/kg AR100-DS1 | 2.34± 0.14 | 0.91± 0.09 | 0.58± 0.05 | 0.75± 0.04 | 0.91± 0.06 |
| Naïve | 2.20± 0.46 | 2.06± 0.19 * | 2.49± 0.22 * | 2.78± 0.17 ** | 2.26± 0.30 * |

TG (mg/dl)
80
70
60
50
40
30
20
10
0
ND
HF
L
ARH003
ARH004
AR101-DS2

TC (mg/dl)
80
70
60
50
40
30
20
10
0
ND
HF
L
ARH003
ARH004
AR101-DS2

HDL-C (mg/dl)
45
40
35
30
25
20
15
10
5
0
ND
HF
L
ARH003
ARH004
AR101-DS2

LDL-C (mg/dl)
25
20
15
10
5
0
ND
HF
L
ARH003
ARH004
AR101-DS2

| | | | ND | HFD | LOVA | ARH003 | ARH004 | AR101-DS2 |
|---|---|---|---|---|---|---|---|---|
| N/M ratio (%) | 1 | N | 0 | 6328 | 3665 | 1336 | 743 | 955 |
| | | M | 0 | 27788 | 36852 | 27909 | 29237 | 29206 |
| | | N/M % | 0 | 22.7724 | 9.99946 | 4.78699 | 2.5413 | 3.26988 |
| | 2 | | ND | HFD | LOVA | ARH003 | ARH004 | AR101-DS2 |
| | | N | 0 | 5846 | 3937 | 1446 | 1192 | 1028 |
| | | M | 0 | 26933 | 37664 | 25656 | 29153 | 32180 |
| | | N/M % | 0 | 21.7057 | 10.453 | 5.63611 | 4.08877 | 3.19453 |
| | 3 | | ND | HFD | LOVA | ARH003 | ARH004 | AR101-DS2 |
| | | N | 0 | 6612 | 3681 | 1354 | 1300 | 866 |
| | | M | 0 | 26607 | 40899 | 25435 | 29168 | 32422 |
| | | N/M % | 0 | 24.8506 | 9.00022 | 5.32337 | 4.45694 | 2.67103 |
| | 4 | | ND | HFD | LOVA | ARH003 | ARH004 | AR101-DS2 |
| | | N | 0 | 8207 | 4139 | 1376 | 1354 | 1091 |
| | | M | 0 | 23555 | 38332 | 26182 | 29272 | 32895 |
| | | N/M % | 0 | 34.8419 | 10.7978 | 5.25552 | 4.62558 | 3.31661 |
| | 5 | | ND | HFD | LOVA | ARH003 | ARH004 | AR101-DS2 |
| | | N | 0 | 6276 | 3305 | 1867 | 241 | 1393 |
| | | M | 0 | 27060 | 38964 | 26769 | 30134 | 32718 |
| | | N/M % | 0 | 23.1929 | 8.48219 | 6.97449 | 0.79976 | 4.2576 |

CH (50 mg/kg) + bleomycin (7.5 mg/kg)

CM (25 mg/kg) + + bleomycin (7.5 mg/kg)

DH (50 mg/kg) + bleomycin (7.5 mg/kg)

DM (25 mg/kg) + + bleomycin (7.5 mg/kg)

EH (50 mg/kg) + bleomycin (7.5 mg/kg)

EM (25 mg/kg) + + bleomycin (7.5 mg/kg)

Control bleomycin (7.5 mg/kg)

DEX + bleomycin (7.5 mg/kg)

ACH (1.0 g/kg) + bleomycin (7.5 mg/kg)

ACM (0.5 g/kg) + + bleomycin (7.5 mg/kg)

AH (50 mg/kg) + bleomycin (7.5 mg/kg)

AM (25 mg/kg) + + bleomycin (7.5 mg/kg)

BH (50 mg/kg) + bleomycin (7.5 mg/kg)

BM (25 mg/kg) + + bleomycin (7.5 mg/kg)

CH (50 mg/kg) + bleomycin (7.5 mg/kg)

CM (25 mg/kg) + + bleomycin (7.5 mg/kg)

DH (50 mg/kg) + bleomycin (7.5 mg/kg)

DM (25 mg/kg) + + bleomycin (7.5 mg/kg)

EH (50 mg/kg) + bleomycin (7.5 mg/kg)

EM (25 mg/kg) + + bleomycin (7.5 mg/kg)

USE OF TERPENOIDS IN THE TREATMENT OR PREVENTION OF FIBROTIC DISEASES

CROSS REFERENCE TO RELATED APPLICATIONS

This application is the National Phase of PCT International Application No. PCT/US2021/033225, filed on May 19, 2021, which claims priority under 35 U.S.C. 119 (e) to U.S. Provisional Application No. 63/027,029, filed on May 19, 2020, all of which are hereby expressly incorporated by reference into the present application.

FIELD OF THE INVENTION

The invention relates to herbal terpenoids from *Antrodia camphorata* and *Anisomeles indica* extract, particularly to a medicinal and edible formula to moderate fibrotic diseases effectively.

BACKGROUND OF THE INVENTION

Fibroproliferative disorders are troubling problems for an increasing number of individuals and is a common pathological sequela of many persistent inflammatory diseases, such as pulmonary fibrosis, progressive kidney disease, liver cirrhosis, atherosclerosis and benign prostatic hyperplasia.

Impaired renal repair after acute kidney injury induces fibrosis which may ultimately lead to the development of chronic kidney disease. Kidney injury activates multipotent progenitor cells to repair tissue. However, these cells become dysfunctional and induce fibrogenic repair as the injury sustains initiating kidney fibrosis. The pathogenesis of renal fibrosis is a progressive process that ultimately leads to end-stage renal failure, a devastating disorder that requires dialysis or kidney transplantation.

Non-alcoholic fatty liver disease (NAFLD) is a leading form of chronic liver disease with large unmet need. Non-alcoholic steatohepatitis (NASH), a progressive variant of NAFLD, can lead to fibrosis, cirrhosis, and hepatocellular carcinoma. NAFLD and NASH are entities that are becoming subject of interest of the medical community in general, especially because of the increased prevalence of diabetes and obesity in the world population. Clinical evaluation of every patient with abnormal aminotransferase levels should take into account non-alcoholic fatty liver and its spectrum, especially if the subject is obese or diabetic. The prognosis of simple NAFLD is generally benign, but if there is fibrosis, ballooning of the hepatocytes, inflammation and Mallory bodies there is risk to progression to cirrhosis.

Autoimmune hepatitis (AIH) is a chronic liver disease without a clear etiology but can be characterized by hepatocellular inflammation. Severe AIH may progress into liver cirrhosis, hepatocellular carcinoma, or even death. Cirrhosis develops in as many as 40% of treated patients with autoimmune hepatitis depending on the length of observation. Anti-fibrotic therapies are emerging that can supplement the anti-inflammatory and immunosuppressive actions of current regimens, and these regimens promise to re-direct the objectives of treatment in autoimmune hepatitis to the prevention, stabilisation and reversal of hepatic fibrosis.

Atherosclerosis, which is one of the primary causes of the development of cardiovascular disease, is associated with vascular fibrosis. Vascular fibrosis involves accumulation of extracellular matrix (ECM) proteins, particularly collagen and fibronectin in the vascular media and contributes to structural remodeling and scar formation. A lack of elastin or excessive collagen in the vascular wall leads to vascular fibrosis and increased stiffness.

In benign prostatic hyperplasia, the deposition of collagen fibers in prostate is for replacing broken myofibers, however results in stiffness and weakness of the muscular tissue and deposition of prostatic fluid in gland tubes. Prostatic fibrosis plays a central role in the development of bladder outlet obstruction in aging men.

Medicinal fungus *Antrodia camphorata* (AC) is a well-known Chinese folk medicine, known to possess numerous biological activities, especially an anti-tumor effect in in vitro cancer cells and in vivo animal models. It is considered an efficient alternative phyto-therapeutic agent or an adjuvant to cancer treatment and immune-related diseases given its diverse bioactive compounds. To date, a total of 225 compounds have been isolated, identified, and structurally elucidated, including macromolecules (nucleic acids, proteins, and polysaccharides), small molecules (benzenoids, lignans, benzoquinones, and maleic/succinic, acid derivatives), terpenoids (lanostane triterpenes, ergostane triterpenes, diterpenes, monoterpenes, and steroids), nucleotides (nucleobase and nucleoside), fatty acids, and fatty acid esters.

Cumulative in vitro and in vivo studies have revealed its anti-diabetic and anti-hyperlipidemic, anti-hypertensive, anti-inflammatory, antioxidant, antimicrobial, cardiovascular disease preventive, immunomodulatory, hepatoprotective, and neuroprotective effects. However, the efficacy of *Antrodia camphorata* and its components in the treatment of fibrosis has not been evaluated.

*Anisomeles indica* commonly known as 'Indian Catmint' is a source of medicinally active compounds and have various pharmacological effects. The plant is used traditionally as an analgesic, anti-inflammatory and in skin problems. Medicinally it has been proven to possess various pharmacological activities like antioxidant, antimicrobial, anti-HIV anti-*Helicobacter pylori* and anti-cancer activity. It is also used in chronic rheumatism. Further studies reveal the presence of various phytochemical constituents mainly triterpenes, β-sitosterol, stigmasterol, flavones, apigenin and ovatodiolides etc.

DETAILED DESCRIPTION OF THE INVENTION

Figure 1:
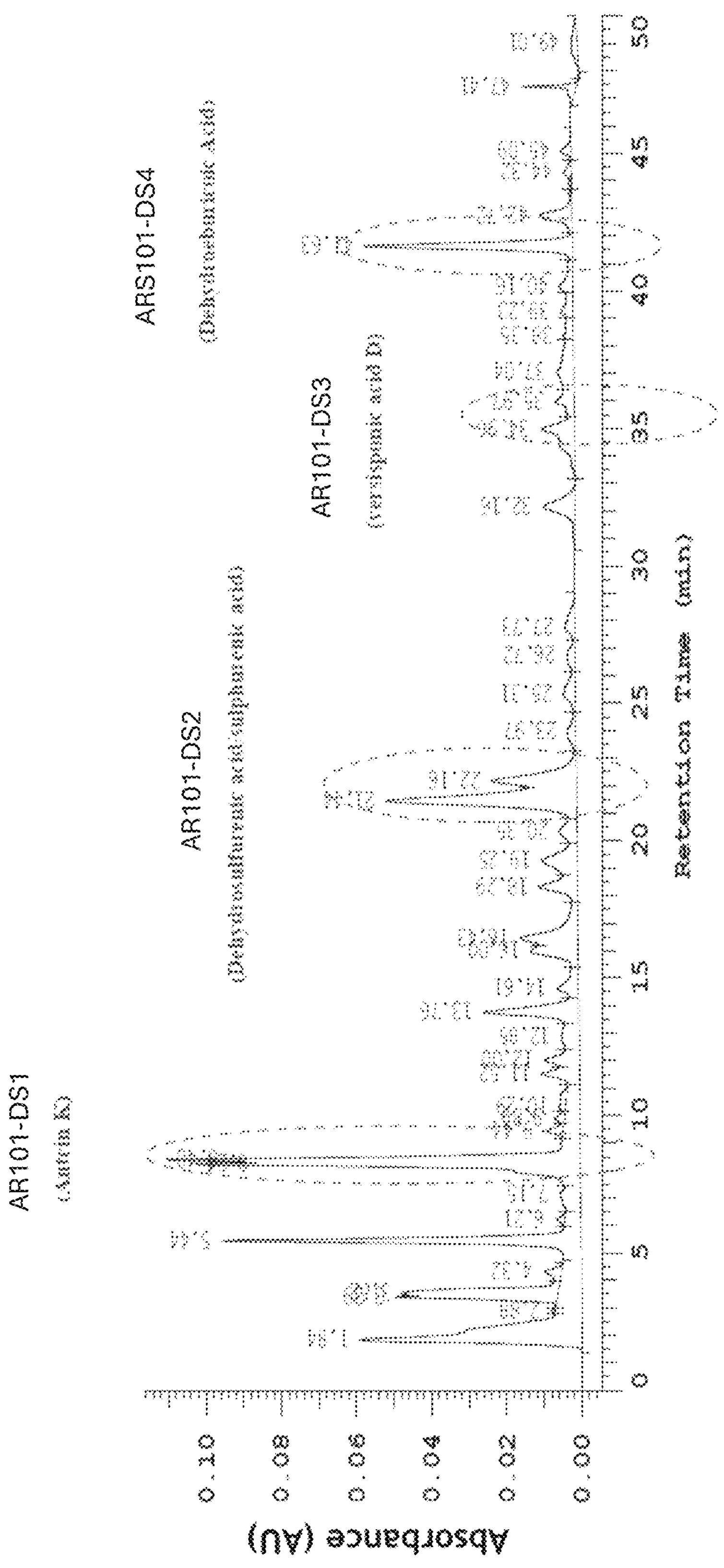
FIG. 1 depicts the separation of antcin K, dehydrosulphurenic acid/sulphurenic acid, versisponic acid D and dehydroehuricoic acid from *Antrodia camphorata* extract FIG. 2 Protective effects of *Antrodia camphorata* Extract and Compounds on cisplatin-induced kidney damage in AKI mice. To analyze the effects of *Antrodia camphorata* Extract and compounds, mice are given daily for 7 days, starting from 3 weeks after first dose of cisplatin, and sacrificed at 4 weeks. The morphological changes in the kidneys (A). Blood urea nitrogen (BUN) levels (B). Serum creatinine (CRE) levels (C). The data are presented as the means±S.E.M (n=5). ###denotes $p<0.001$ compared with sample of control group. $p<0.01$ and *$p<0.001$ compared with cisplatin group.

For the convenience of the description of the present invention, the central idea expressed in the above summary of the invention is expressed by way of specific examples. Various items in the embodiments are depicted in terms of ratios, dimensions, amounts of deformation, or displacements that are suitable for illustration, and are not drawn to the proportions of actual elements, as set forth above.

The term "terpenes" refers to a large and diverse class of organic compounds, whose basic structure follows a general principle: 2-Methylbutane residues, less precisely but usually also referred to as isoprene units, $(C_5)_n$, build up the carbon skeleton of terpenes. About 30 000 terpenes are known at present in the literature. Depending on the number of 2-methylbutane (isoprene) subunits one differentiates between hemi-($C_5$), mono-($C_{10}$), sesqui-($C_{15}$), di-($C_{20}$), sester-($C_{25}$), tri-($C_{30}$), and tetraterpenes ($C_{40}$).

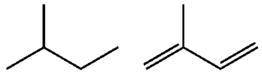

2-Methylbutane Isoprene

The terms "subject," "individual," "host, and "patient" are used interchangeably herein to refer to a living animal, including a human and a non-human animal. The Subject may, for example, be an Organism possessing immune cells capable of responding to antigenic stimulation, and stimulatory and inhibitory signal transduction through cell Surface receptor binding. The Subject may be a mammal. Such as a human or non-human mammal, for example, dogs, cats, pigs, cows, sheep, goats, horses, rats, and mice. The term subject does not preclude individuals that are entirely normal with respect to a disease, or normal in all respects.

The term "treatment" refers to a therapeutic or preventative measure. The treatment may be administered to a subject having a medical disorder or who ultimately may acquire the disorder, in order to prevent, cure, delay, reduce the severity of or ameliorate one or more symptoms of a disorder or recurring disorder, or in order to prolong the Survival of a subject beyond that expected in the absence of such treatment.

The term "therapeutically effective amount' means the amount of the subject compound that may elicit a desired response, for example, a biological or medical response of a tissue, System, animal, or human that is sought, for example, by a researcher, veterinarian, medical doctor, or other clinician.

Determination of biochemical parameters Serum creatinine and serum urea are assessed using colorimetric kits according to manufacturer's instructions. Kits of the former markers are purchased from (HUMAN Diagnostics Worldwide, Magdeburg, Germany) with a chemical analyzer (Roche Diagnostics, Cobas Mira Plus, Rotkreuz, Switzerland).

Kidney histopathology The anterior portion of the left lateral liver lobe from each mouse is fixed in 10% formaldehyde phosphate butler, embedded in paraffin, cut into 5 μm sections, and then treated with an hematoxylin and eosin (H&E) stain for histological examination under the light microscopy (Nikon, ECLIPSE, TS100, Tokyo, Japan). Images are captured with a digital camera (NIS-Elements D 2.30, SP4, Build 387) at an original magnification of 400×.

TNF-α, IL-6, and IL-1β cytokines in serum The serum concentration of the pro-inflammatory cytokines (i.e. tumor necrosis factor-α (TNF-α), interleukin-6 (IL-β), and IL-1β) in serum are assessed with relevant enzyme-linked immunosorbent assay (ELBA) kits (Biosource International Inc., Sunnyvale, CA, USA), based on the manufacturer's instructions.

Western blot analysis of the kidney tissues Lysis buffer, composed of 0.6% NP-40, 150 mM NaCl, 10 mM HEPES (pH 7.9), 1 mM EDTA, and 0.5 mM PMSF, is used in the homogenization of liver tissues at 4° C. The homogenized samples are then centrifuged at 3000 revolutions per minute (rpm) at 4° C. for 10 min to obtain the supernatant. The equal total cellular protein amounts of supernatant are determined by the protein standard of bovine serum albumin (BSA). Protein samples (50 μg) are resolved by denaturing 10% sodium dodecyl sulfate-polyacrylamide gel electrophoresis (SDS-PAGE) using standard methods, and then are transferred onto PVDF membranes (Immobilon, Millipore, Bedford, MA, USA) for electroblotting and blocking with 10% skim milk. The membranes are incubated with an appropriate dilution of specific primary antibodies at 4° C., washed three times with TBS/tween (TBST) buffer, and subsequently incubated for 1 h at 37° C. with horseradish peroxidase-conjugated secondary antibodies (overnight). The membranes are washed three times before examination for immuno-reactive proteins by enhanced chemiluminescence (ECL) reagent (Thermo Scientific, Hudson, NH, USA). Band intensity on scanned films are quantified and represented as relative intensity by comparing with the control group using Image 3 Software Bethesda, MD, USA).

Statistical analysis Data obtained from animal experiments are expressed as the means and standard errors of the means (+S.E.M.). Student's t-test are used to examine the differences among multiple groups or between two groups. Statistical significance is expressed as *$p<0.05$, $p<0.01$ and *$p<0.001$.

EXAMPLE 1

Preparation of *Antrodia camphorata* Extract 100 grams of *Antrodia camphorata* fruiting body is reflux with methanol for 6 hours, and the extract is collected and dried, thereby obtaining a total of 15 grams of methanol extract of *Antrodia camphorata.*

EXAMPLE 2

Preparation of Active Ingredients: Antcin K, Dehydrosulphurenic Acid/Sulphurenic Acid, Versisponic Acid D and Dehydroeburicoic Acid The methanol extract of *Antrodia camphorata* is further separated by silica column chromatography using n-hexane/ethyl acetate/methanol as eluent to provide the fractions (shown in FIG. 1):

ARH101-DS1 (RS-Antcin K),

ARH101-DS2 (Dehydrosulphurenic acid/Sulphurenic acid),

ARH101-DS3 (Versisponic acid D) and

ARH101-DS4 (Dehydroeburicoic Acid).

25R-Antcin K

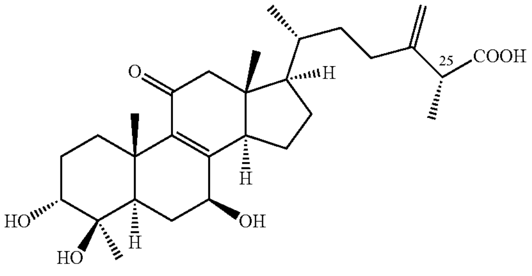

-continued

25S-Antcin K

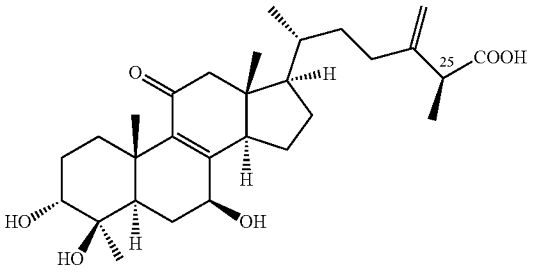

Dehydrosulphurenic acid

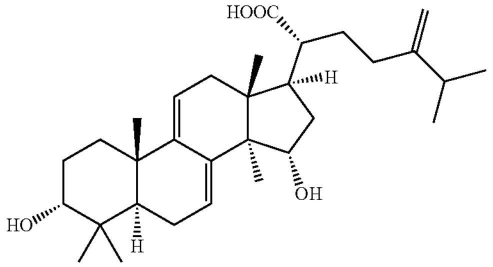

Sulphurenic acid

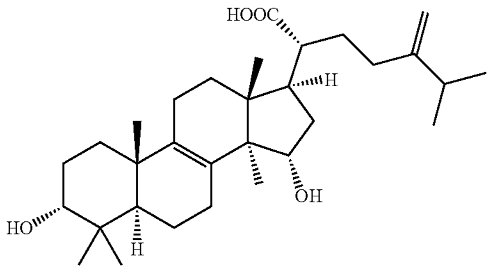

Verisponic acid D

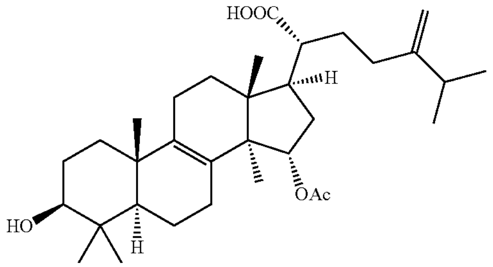

Dehydroeburicoic Acid

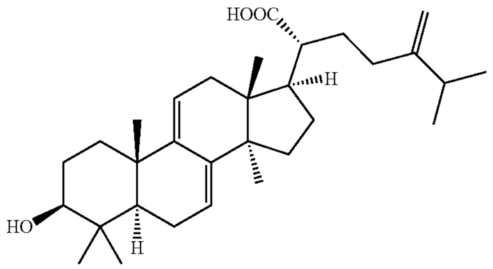

EXAMPLE 3

Preparation of AR003 Extract 100 grams of *Antrodia camphorata* (petri dish culture) is reflux with methanol for 6 hours, and the extract is collected and dried under reduced pressure to obtain 15 grams of the *Antrodia camphorate* ARH003 extract.

EXAMPLE 4

Preparation of AR003-E Extract 200 grams of *Antrodia camphorata* (petri dish culture) is reflux with ethanol for 6 hours, and the extract is collected and dried, thereby obtaining a total of 18 grams of ethanol extract of AR003-E *Antrodia camphorata.*

EXAMPLE 5

Preparation of AR004 Extract 100 grams of *Antrodia camphorata* (wood culture) is reflux with methanol for 6 hours, and the extract is collected and dried under reduced pressure to obtain the *Antrodia camphorate* ARH004 extract.

EXAMPLE 6

Preparation of AR005-EA Extract 100 grams of *Antrodia camphorata* (solid culture) is reflux with ethyl acetate for 6 hours, and the extract is collected and dried, thereby obtaining a total of 12 grams of EA extract of *Antrodia camphorata.*

EXAMPLE 7

Preparation of *Anisomeles indica* Extract

The *Anisomeles indica* extract is prepared by the following process: (1) An ethanol extract of *Anisomeles indica* is taken, added into a silica-filled chromatographic column, and subjected to a gradient elution with the eluents "n-hexane/ethyl acetate", "hexane ethyl acetate/methanol" and "methanol" to obtain an *Anisomeles indica* parting liquid. (2) The *Anisomeles indica* parting liquid is separated by using silica-filled chromatographic column, and subjected to a gradient elution with the eluents "dichloromethane", "dichloromethane/methanol" and "methanol" to obtain a separated concentrating substance; (3) the separated concentrating substance is recrystallized with the solvent "n-hexane/ethyl acetate" to obtain the *Anisomeles indica* crystallite.

EXAMPLE 8

Preparation of Active Ingredients: Ovatodiolide (AR100-DS1)

200 g of ethanol extract of *Anisomeles indica* is taken, added into a silica-filled chromatographic column (10×15 cm), and subjected to a gradient elution with 1200 ml of each of the eluents: "n-hexane ethyl acetate (with a ratio of 10/1, 5/1, 3/1, 1/1)", "hexane/ethyl acetate/methanol (with a ratio of 6/4/1, 3/2/1)" and "methanol" to obtain 140 g of an initial parting liquid.

The 140 g of the initial parting liquid is separated by using silica-filled chromatographic column (10×15 cm), and subjected to a gradient elution with 1000 ml of each of the eluents: "dichloromethane", "dichloromethane/methanol (with a ratio of 10/1, 5/1, 7/3)" and "methanol" to obtain a separated concentrating substance. The separated concentrating substance is further recrystallized with the solvent: "n-hexane/ethyl acetate" to obtain a crystal. The crystal is identified as a diterpenoid compound whose chemical structure is ovatodiolide by a nuclear magnetic resonance spectroscopy (H1-NMR). The crystal is compared with the standard product of ovatodiolide by high performance liquid chromatography (HPLC) analysis, and is recognized to have ovatodiolide compounds.

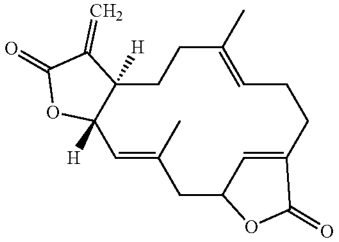

Ovatodiolide

Metabolites from Ovatodiolide (AR100-DS1):

+O, +Cysteine: m/z: 466, M2, M3, M4

+Glutathione: m/z: 636, M6, M7

+O: m/z:345, M8, M9

| Compound No. | Compound name and structure |
|---|---|
| AR101-DS1 | 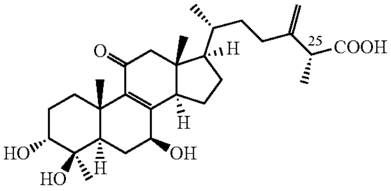 25R-Antcin K |
| | 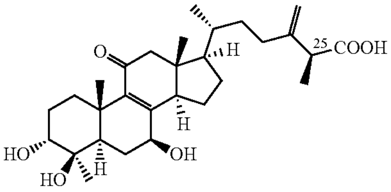 25R-Antcin K |
| AR101-DS2 | 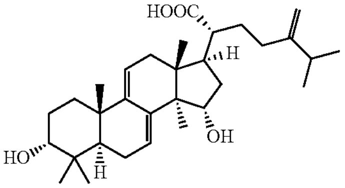 Dehydrosulphurenic acid |
| | 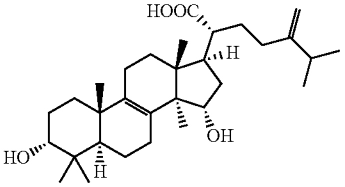 Sulphurenic acid |

-continued

| Compound No. | Compound name and structure |
|---|---|
| AR101-DS3 | 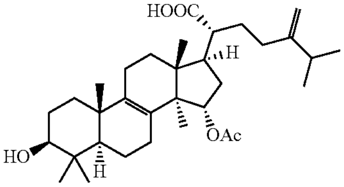 Versiponic acid D |
| AR101-DS4 | 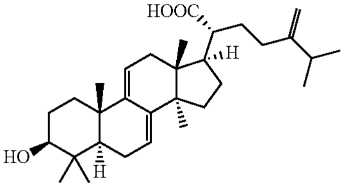 Dehydroeburicoic Acid |
| AR100-DS1 | 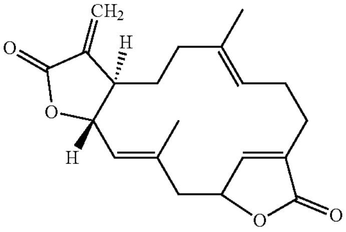 Ovatodiolide |
| AR100-DS4 | 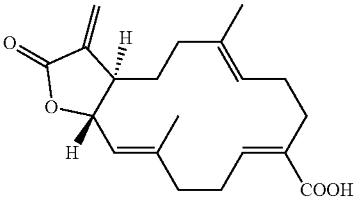 Anisomelic acid |
| AR100-DS5 | 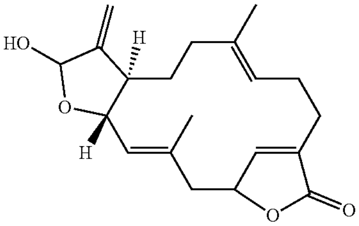 [SMILES: C=C1C(O)O[C@H]2/C=C(\C)CC3C=C(CC/C=C(\C)CC[C@H]12)C(=O)O3] |
| AR100-DS6 | 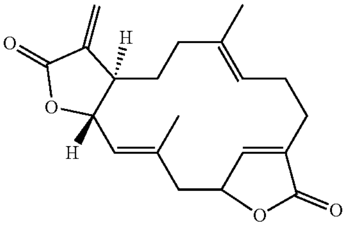 [SMILES: C=C1C(=O)O[C@H]2/C=C(\C)CC3C=C(CC/C=C(\C)CC[C@H]12)C(=O)O3] |

-continued

| Compound No. | Compound name and structure |
|---|---|
| AR100-DS7 | 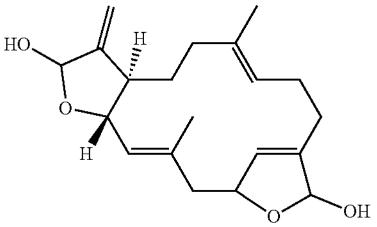 [SMILES: C=C1C(O)O[C@H]2/C=C(\C)CC3C=C(CC/C=C(\C)CC[C@H]12)C(O)O3] |
| AR100-DS8 | 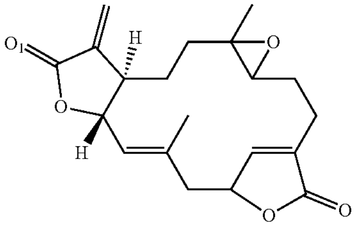 |
| AR100-DS9 | 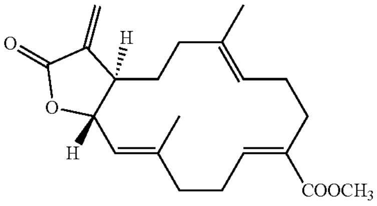 [SMILES: C=C1C(=O)O[C@H]2/C=C(\C)CC/C=C(\C(=O)OC)CC/C=C(\C)CC[C@H]12] |
| AR100-DS10 | 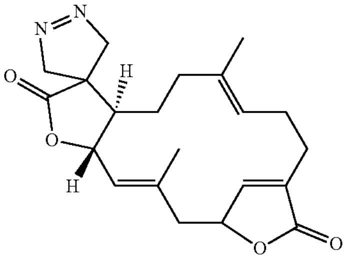 [SMILES: C/C1=C\CCC2=CC(C/C(C)=C/[C@@H]3OC(=O)C4(CN=NC4)[C@H]3CC1)OC2=O] |
| AR100-DS11 | 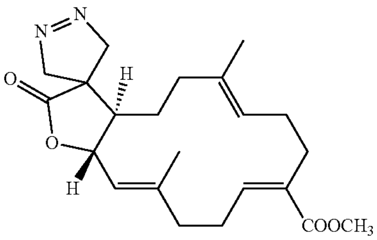 [SMILES: COC(=O)/C1=C\CC/C(C)=C/[C@@H]2OC(=O)C3(CN=NC3)[C@H]2CC/C(C)=C/CC1] |
| AR100-DS12 | 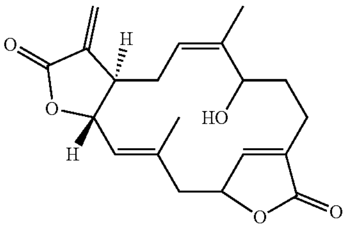 [SMILES: C=C1C(=O)O[C@H]2/C=C(\C)CC3C=C(CCC(O)/C(C)=C\C[C@H]12)C(=O)O3] |

-continued

| Compound No. | Compound name and structure |
|---|---|
| AR100-DS13 | 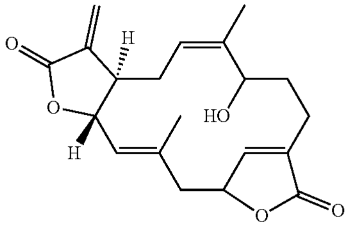 [SMILES: C=C1C(=O)O[C@H]2/C=C(\C)CC3C=C(CCC(O)/C(C)=C\C[C@H]12)C(=O)O3] |

EXAMPLE 9

Mice Model of Cisplatin-Induced Renal Injury

Seven-to-eight-week-old male C57BL/6 mice are obtained from the BioLASCO Taiwan Co., Ltd, (Taipei, Taiwan). The animals are housed in Plexiglas cages at a constant temperature of 22±1° C. and a relative humidity of 55±5% on a 12 h dark-light cycle for at least 2 weeks before the experiment. Animals are provided food and water ad libitum. All experimental procedures are performed according to the guidelines of the institutional Animal Ethics Committee, and the protocol is approved by the Committee for the Purpose of Control and Supervision of Experiments on Animals.

Renal fibrosis is induced via multiple injections of low-dose cisplatin. Intraperitoneal injections of cisplatin (5 mg/kg/injection; P4394, Sigma-Aldrich, St Louis, MO) are performed at 0, 1, and 3 weeks, for a total of 3 injections. Mice are sacrificed at 6 weeks after the first dose of cisplatin (n=6). To analyze the effects of samples, mice are given daily intraperitoneal injections for 7 days, starting from 4 weeks after first dose of cisplatin, and sacrificed at 4 weeks (n=6).

EXAMPLE 10

Figure 2A:
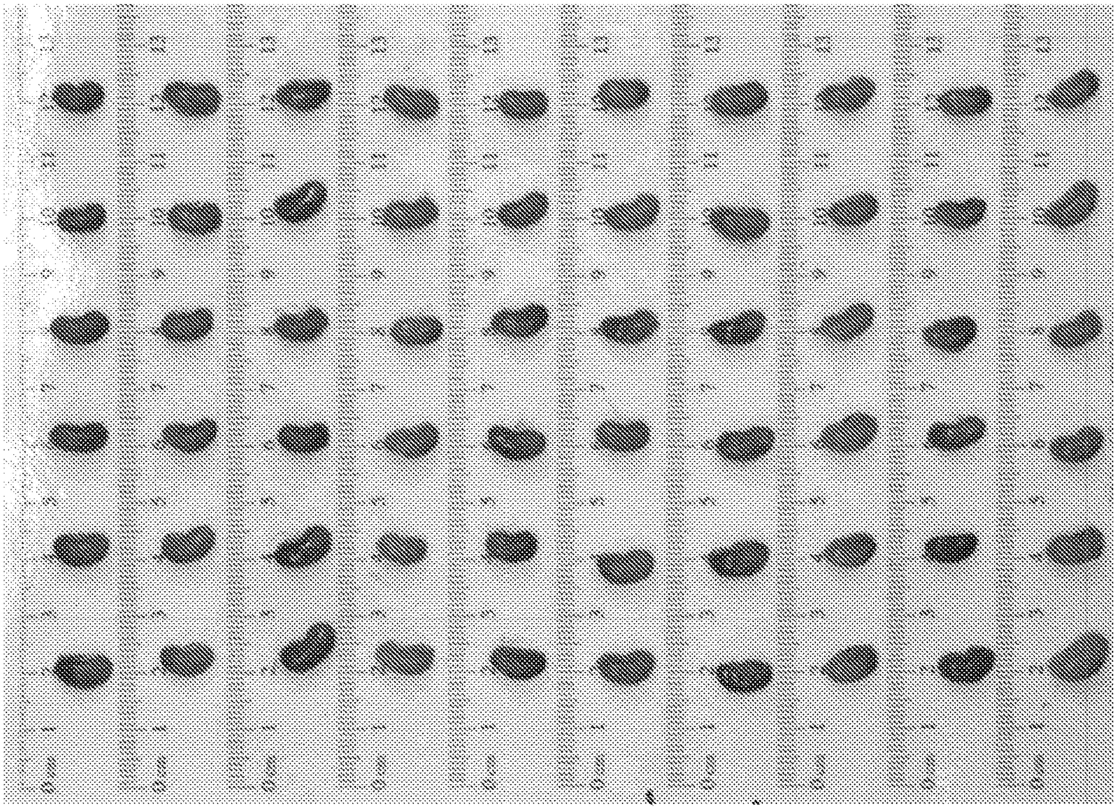
Figure 2B:
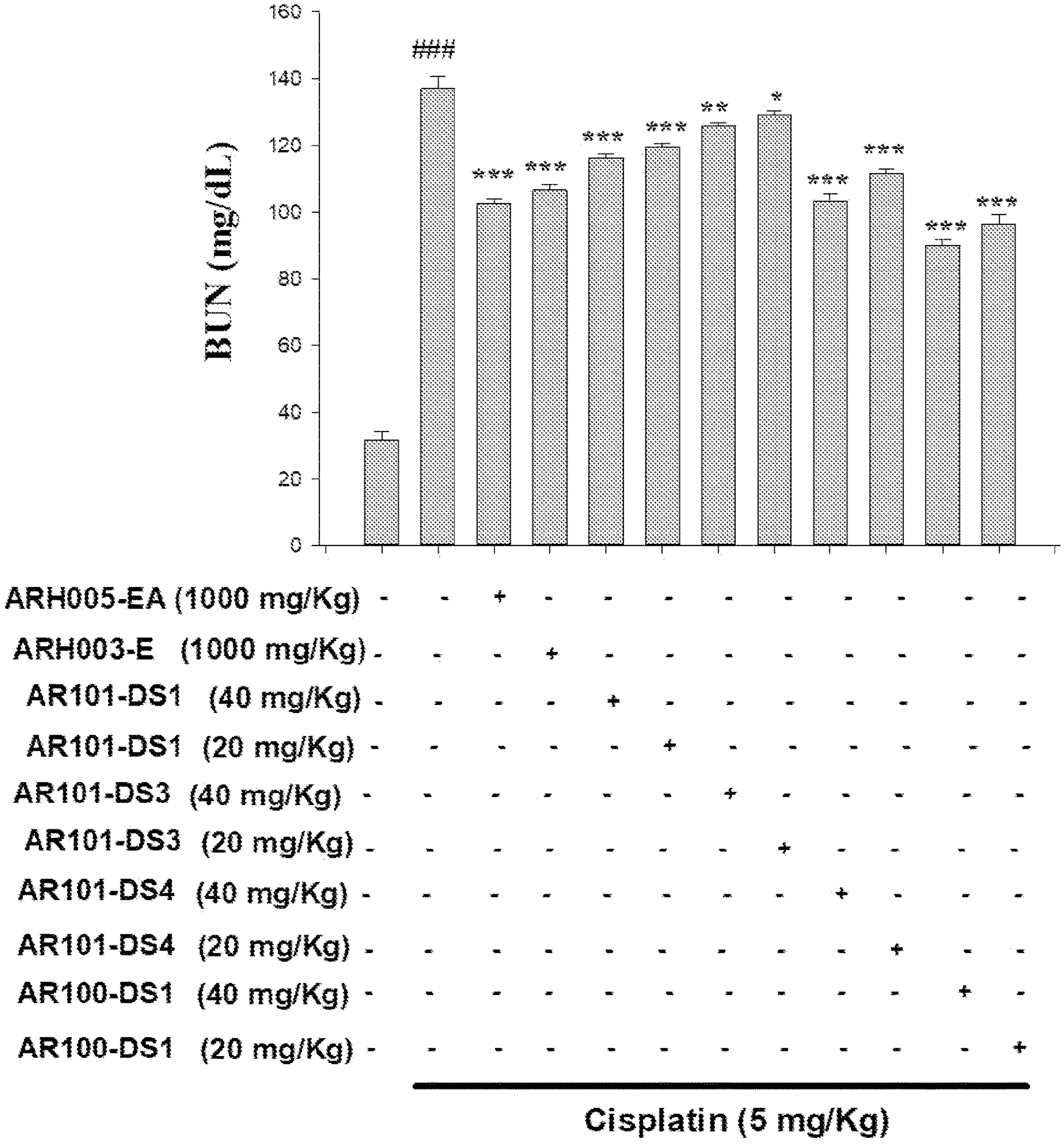
Figure 2C:
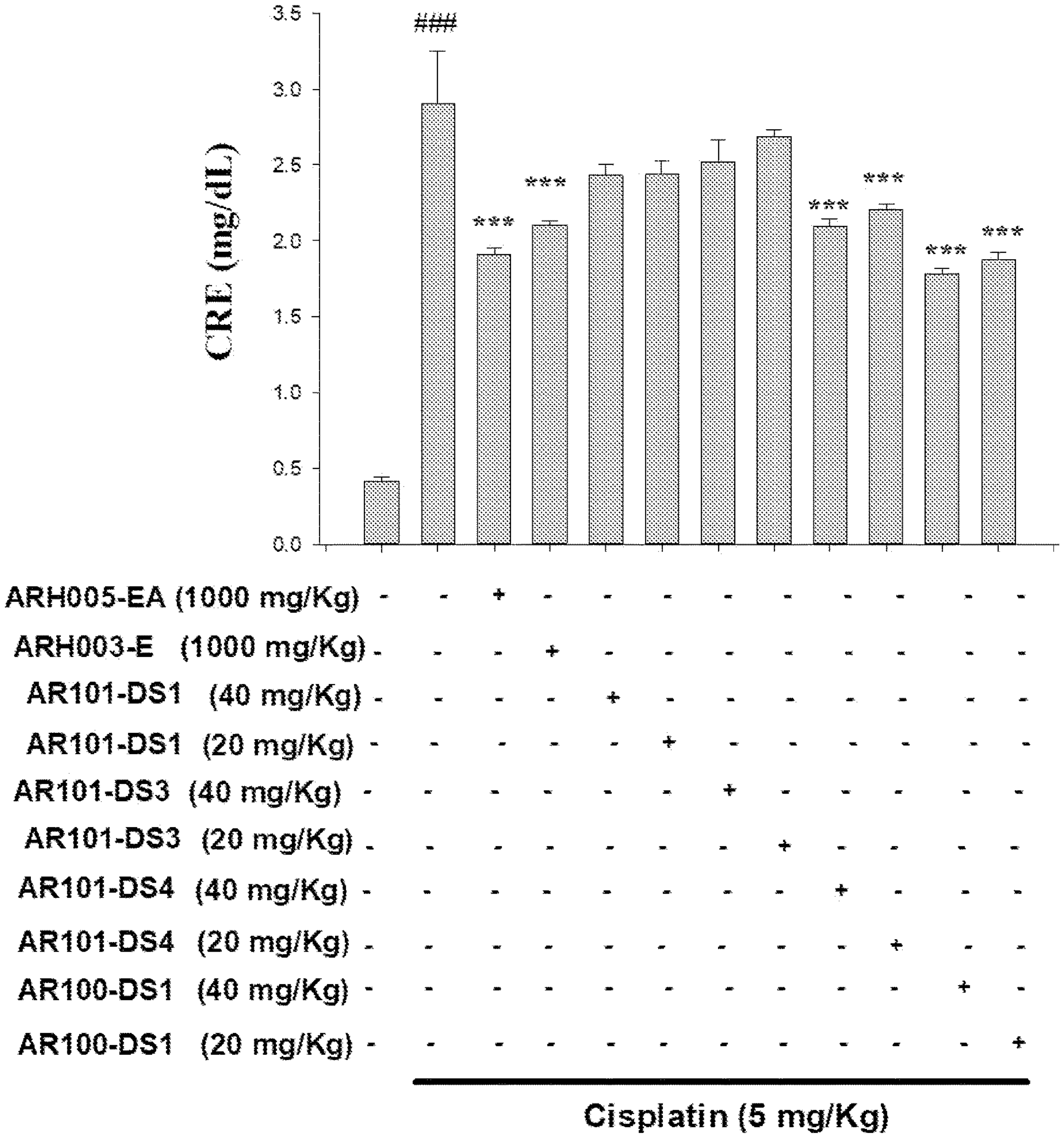

*Antrodia camphorata* Extract and Compounds Reduced Renal Dysfunction and Histopathological Changes in Cisplatin-Induced Mice The morphological changes in the kidneys are shown in the FIG. 2A. CRE and BUN are hallmarks of kidney function. FIGS. 2B and 2C show that, compared to the control group, cisplatin injection at the three 10 mg/kg CP doses (at 0, 1, 3 weeks) highly increased the serum CRE and BUN levels (p<0.001), indicating the generation of nephrotoxicity in the cisplatin-treated mice. Treatment with ARH005-EA and ARH003-E at doses of 1000 mg/kg and compounds (AR101-DS4 and AR100-DS1) exerted a significant renal protection effect in a dose-dependent manner, as demonstrated by the normalization of CRE and BUN (p<0.001) compared to cisplatin-stimulated group.

EXAMPLE 11

Figure 3:
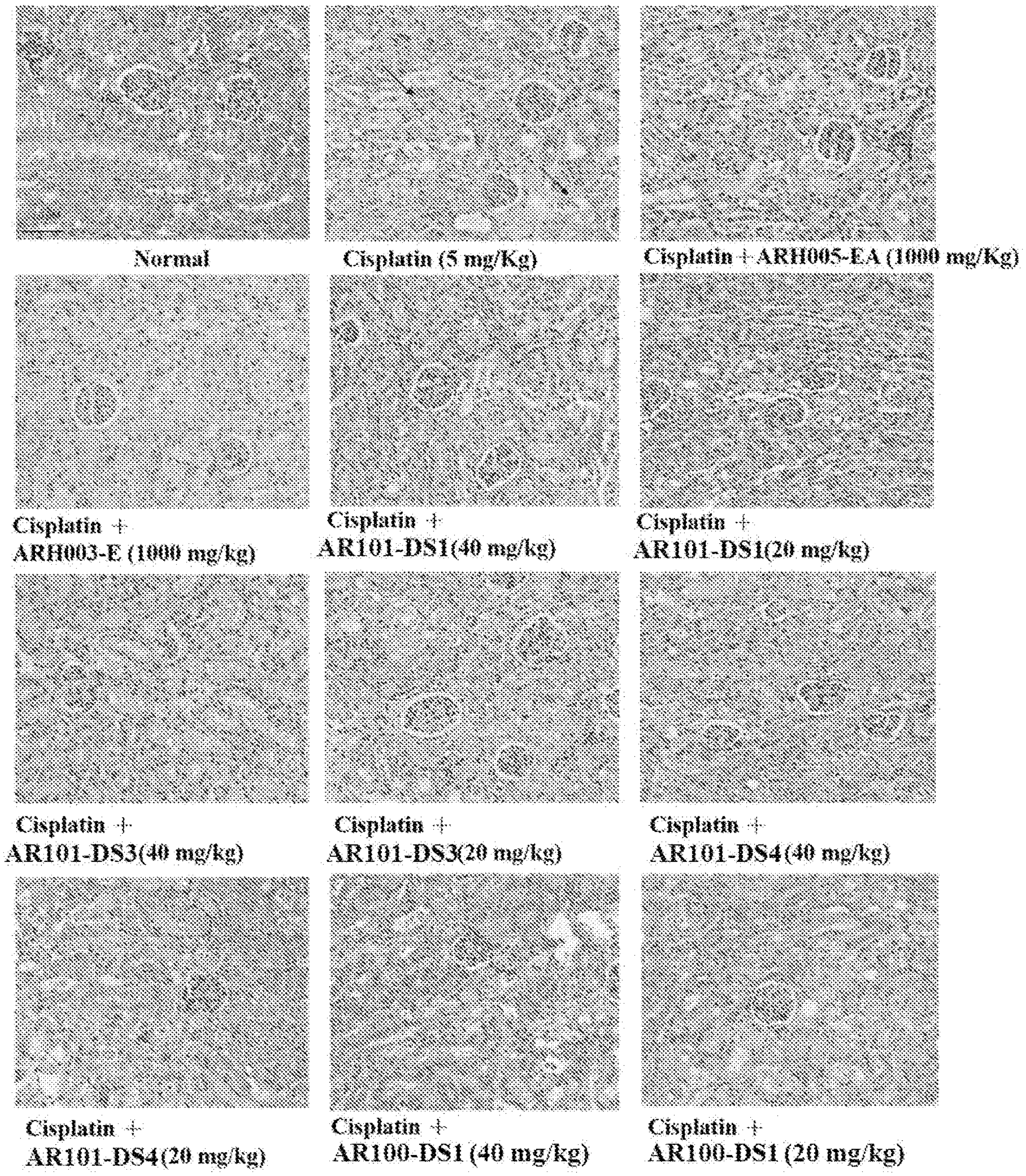
FIG. 3 Protective effects of *Antrodia camphorata* Extract and Compounds on cisplatin-induced kidney damage in AKI mice. To analyze the effects of *Antrodia camphorata* Extract and compounds, mice are given daily for 7 days, starting from 3 weeks after first dose of cisplatin, and sacrificed at 4 weeks. Kidneys stained with H&E. After cisplatin challenge, kidneys in each group are prepared for histological evaluation. Representative histological section of the kidneys is stained by H&E staining, magnification (400×). The data are presented as the means±S.E.M (n=5). ###denotes p<0.001 compared with sample of control group. p<0.01 and *p<0.001 compared with cisplatin group. Tubular cell necrosis is marked with arrows; the bar indicates 50 μm.
Figure 4A:
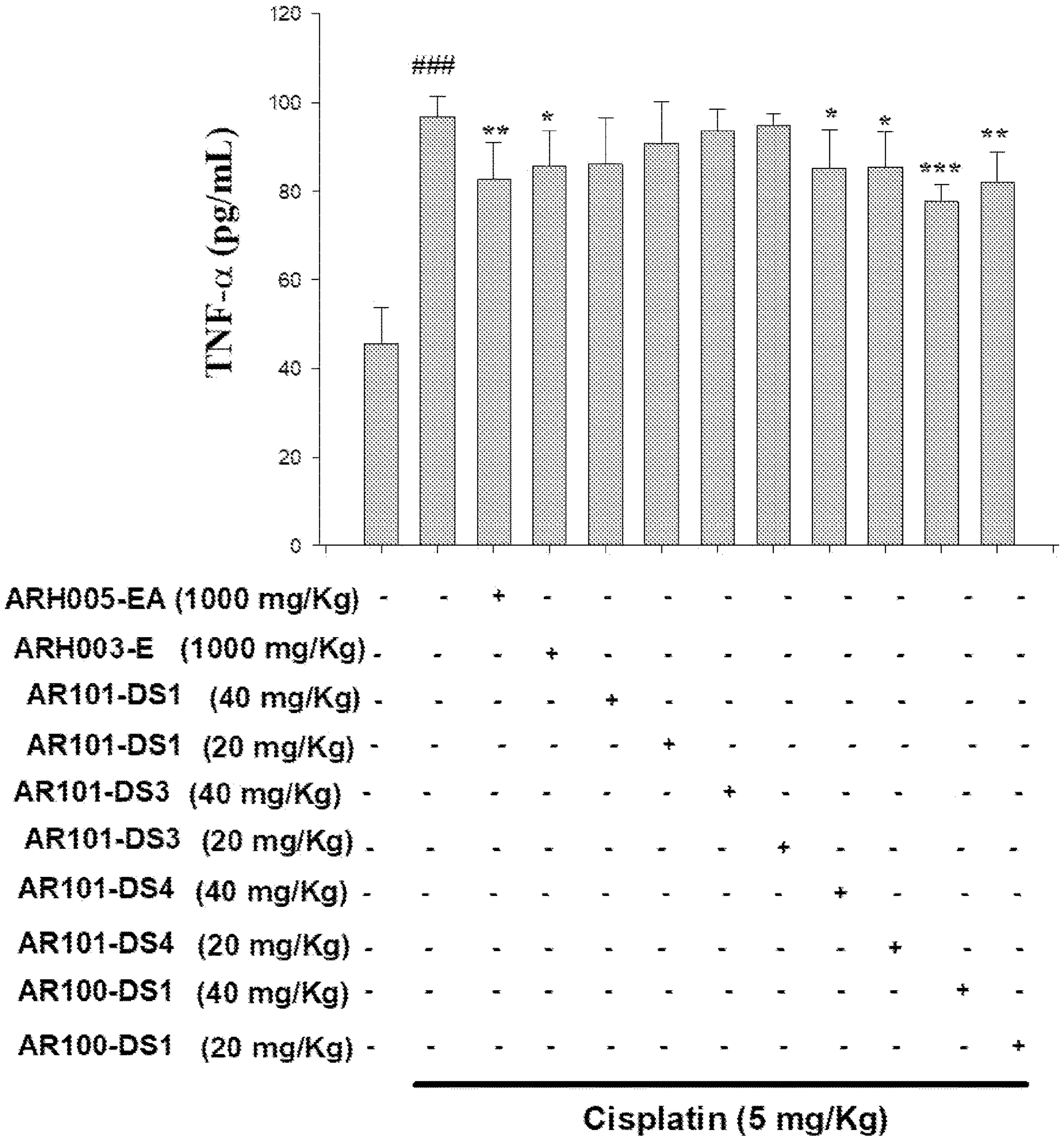
FIG. 4 *Antrodia camphorata* Extract and Compounds regulated (A) TNF-α (B) IL-1β, (C) IL-6 (D) TGF-β and (E) albumin in serum. Serum levels of TNF-α, IL-1β, IL-6, TGF-β and albumin are determined by commercial ELISA kits. Data are represented as mean±S.E.M. (n=5). ###denotes p<0.001 compared with sample of control group. p<0.01 and *p <0.001 compared with cisplatin-only group.
Figure 4B:
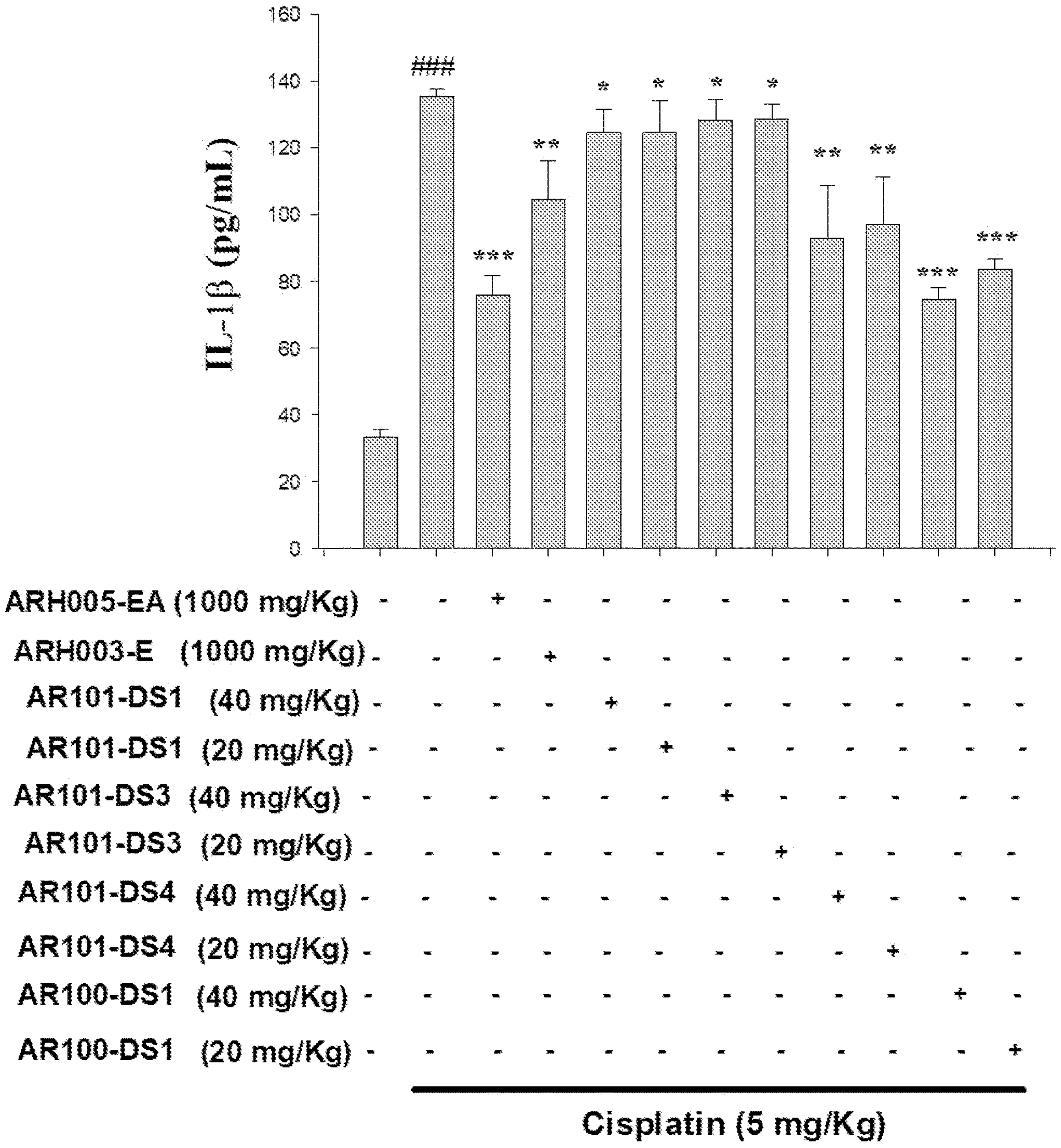
Figure 4C:
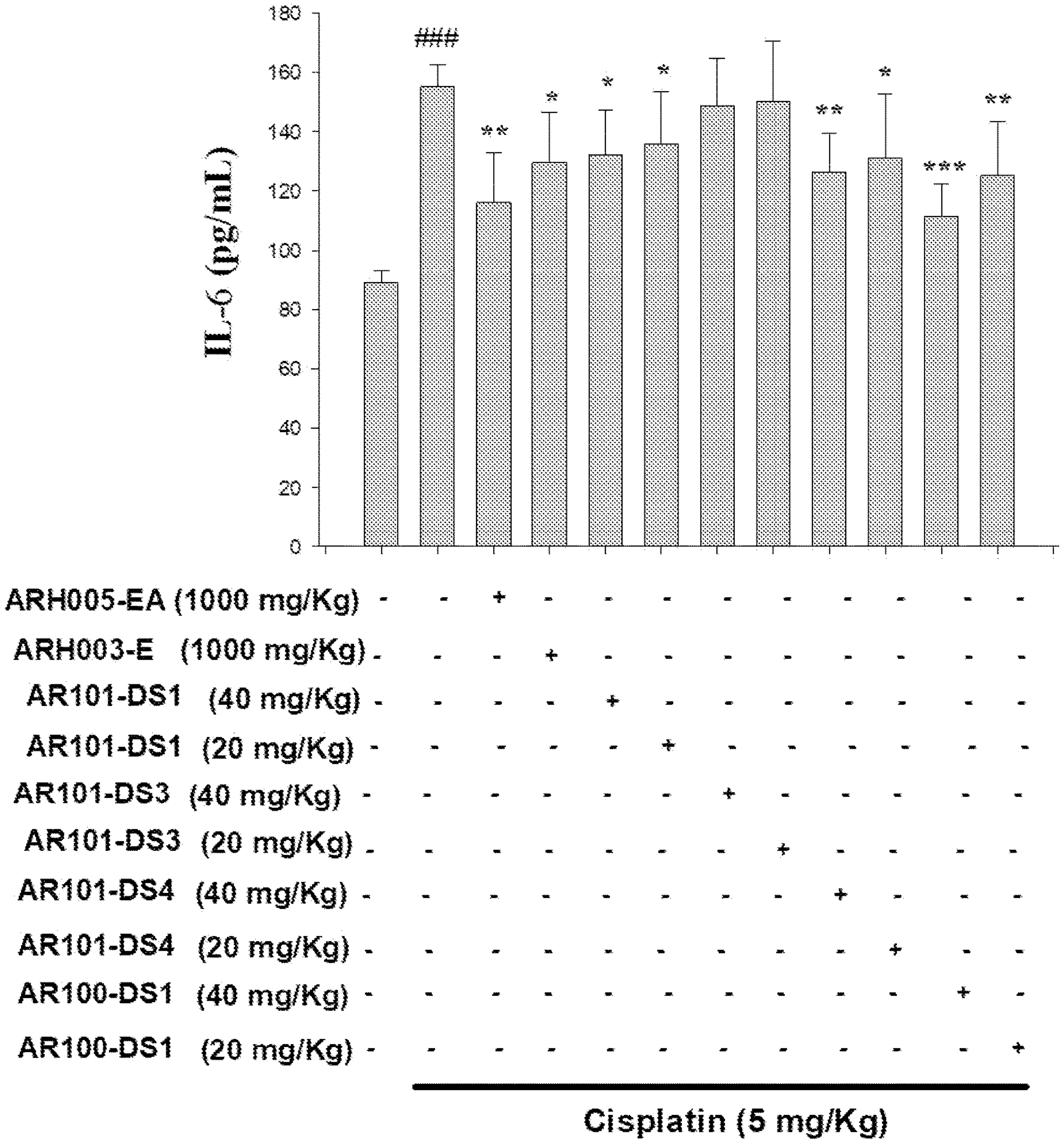
Figure 4D:
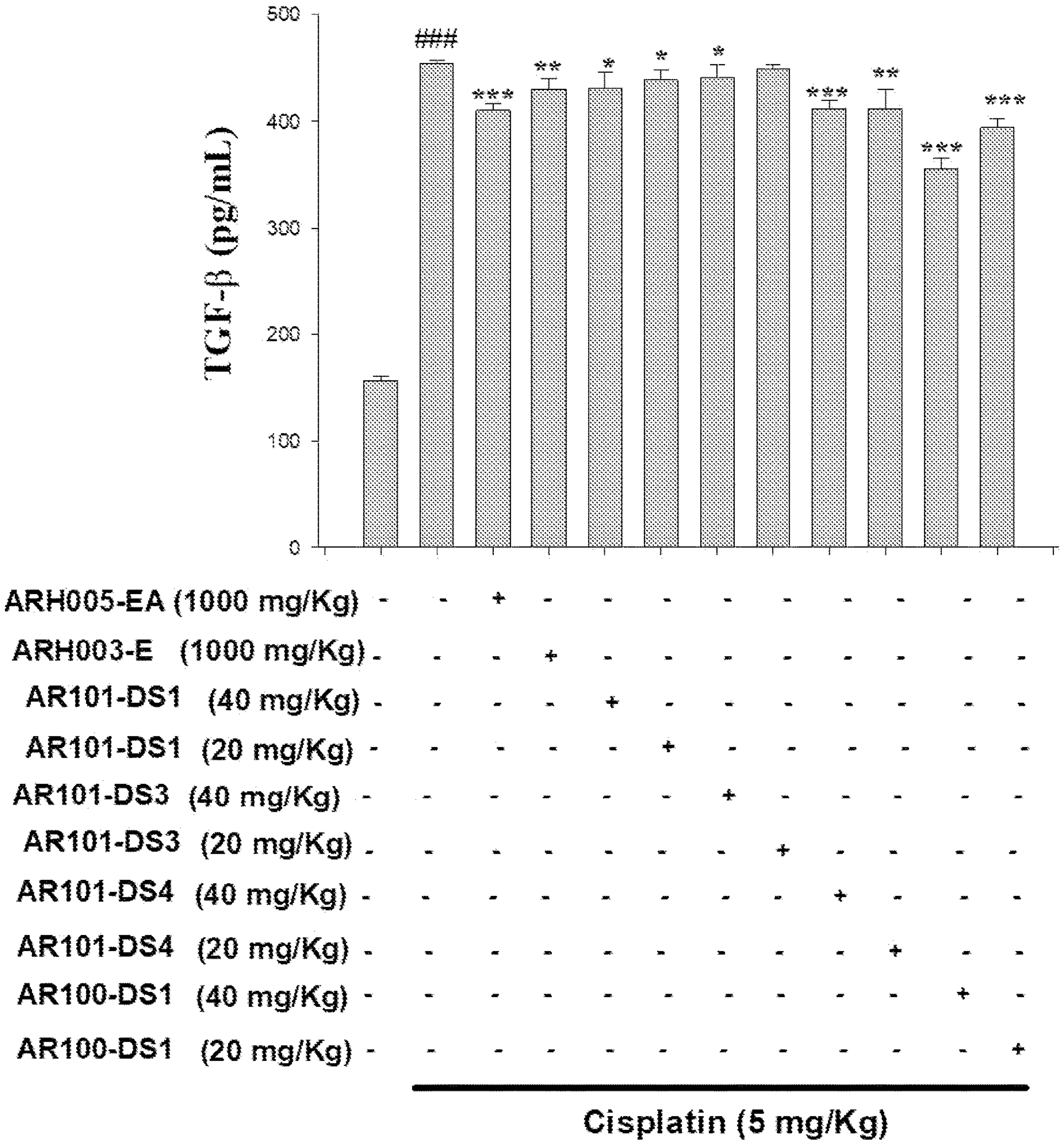
Figure 4E:
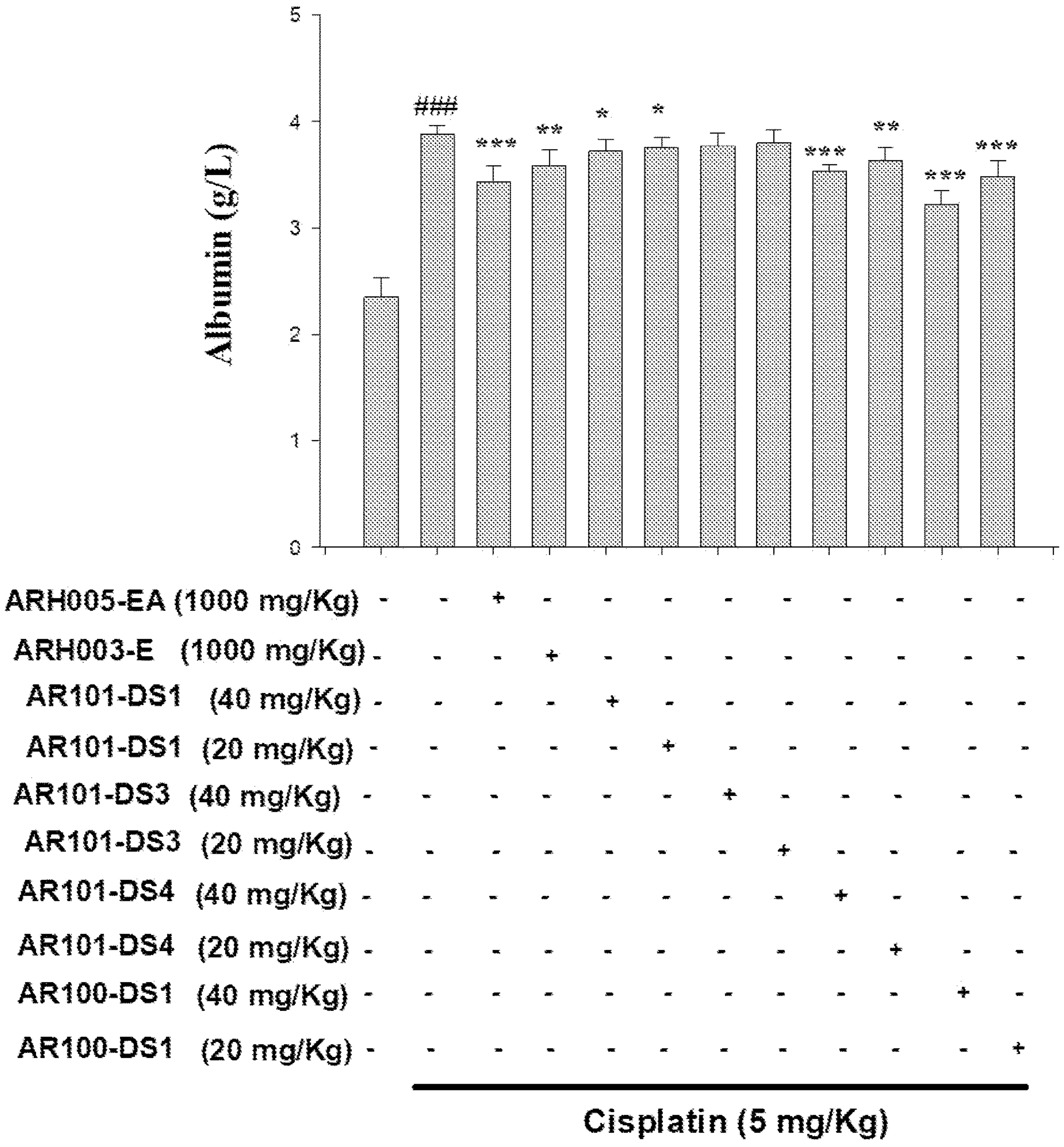

*Antrodia camphorata* Extract and Compounds Alleviates Renal Dysfunction and Renal Injury Induced By Multiple Cisplatin Treatment The histopathological changes are analyzed to determine whether *Antrodia camphorata* extract and compounds affected renal failure in cisplatin-stimulated mice. The kidney tissue of the control group is completely normal and characterized by a transparent tubular and glomerular structure with clear and normal nuclei. Kidneys had severe kidney damage in the cisplatin-stimulated mice, inducing tubular epithelial damage, inflammatory cell infiltration, tubular cell swelling, formation of intratubular casts, and tubular dilatation. However, treatment with *Antrodia camphorata* extract (AR005-EA) at doses of 1000 mg/kg and compounds (AR100-DS1) significantly improved necrosis and inflammatory infiltrating cells in the kidney tissue (see FIG. 3).

EXAMPLE 12

*Antrodia camphorata* Extract and Compounds Alerted the Cisplatin Induced Changes in Pro-Inflammatory Cytokines and Albumin Evaluation of proinflammatory cytokine TNF-α, IL-1β, IL-6 and TGF-β levels in serum are performed by ELISA. Cisplatin-treated kidney injury mice had significantly increased NO, TNF-α, IL-1β, and IL-6 levels in serum, compared to the control group (FIGS. 4A-4E, respectively). Treatment with *Antrodia camphorata* Extract (AR005-EA) at doses of 1000 mg/kg and compounds (AR100-DS1) significantly improved necrosis and inflammatory infiltrating cells in the kidney tissue treatment improved NO, TNF-α, IL-1β, and IL-6 production after cisplatin challenge.

EXAMPLE 13

Figure 5A:
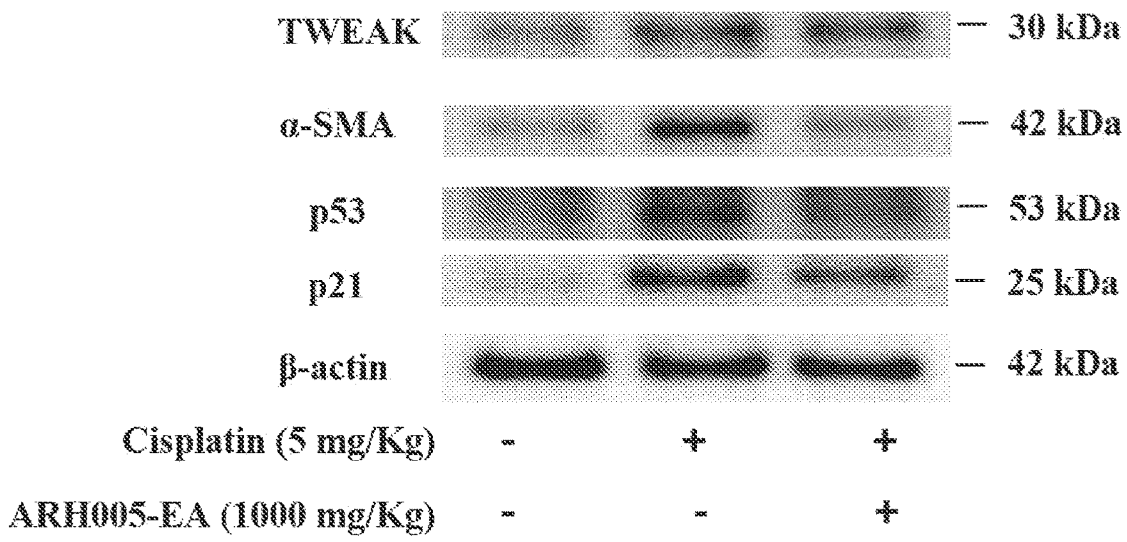
FIG. 5 Effects of ARH005-EA (A) and ARH (B) on cisplatin-induced TWEAK, α-SMA, P53 and P21 signaling expression in kidneys. Protein levels of TWEAK, α-SMA, P53 and P21 protein expression in kidney homogenates are evaluated by western blot analysis after cisplatin challenge.
Figure 5B:
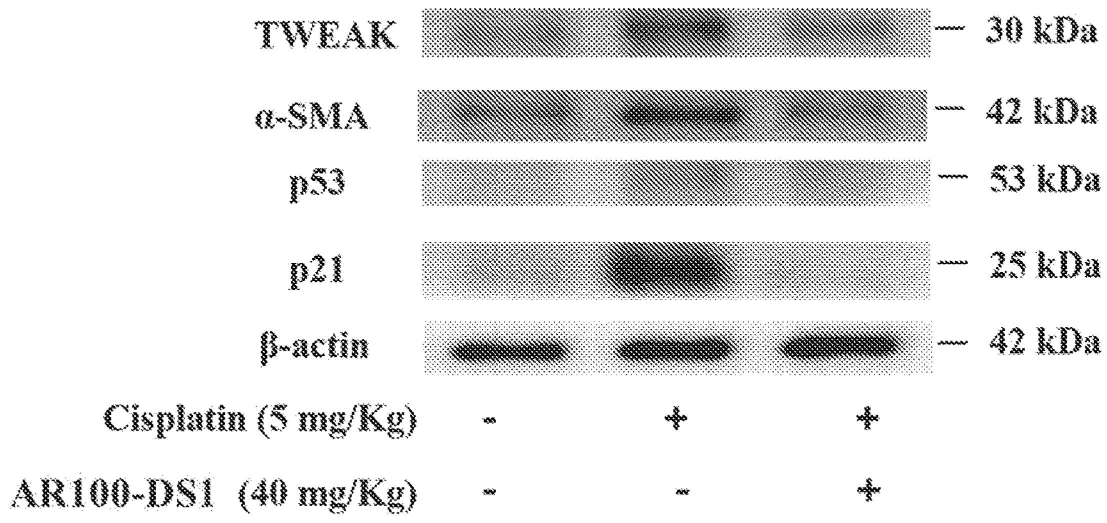

Inhibition of Cisplatin-Induced Renal Injury TWEAK, α-SMA, P53 and P21 Protein Expression The results are examined whether pretreatment with *Antrodia camphorata* Extract (ARH005-EA) and compounds (AR100-DS1) inhibited cisplatin-induced TWEAK, α-SMA, P53 and P21 protein expression. The results revealed that treatment with ARH005-EA and ARH inhibited the protein expression of TWEAK, α-SMA, P53 and P21 in the kidney tissues after the cisplatin challenge (FIGS. 5A and 5B).

EXAMPLE 14

$CCl_4$-Induced Chronic Liver Fibrosis in Rat

Figure 6:
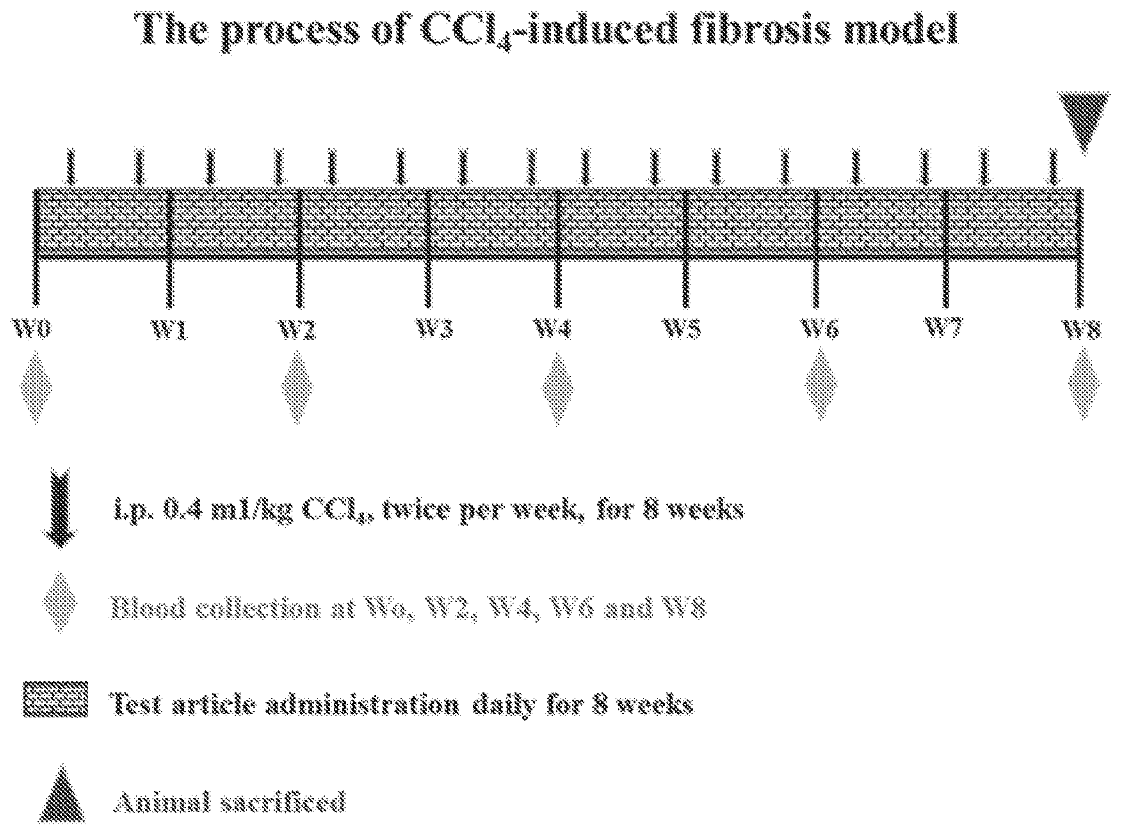
FIG. 6 depicts the process of $CCl_4$-induced fibrosis model
Figure 7A:
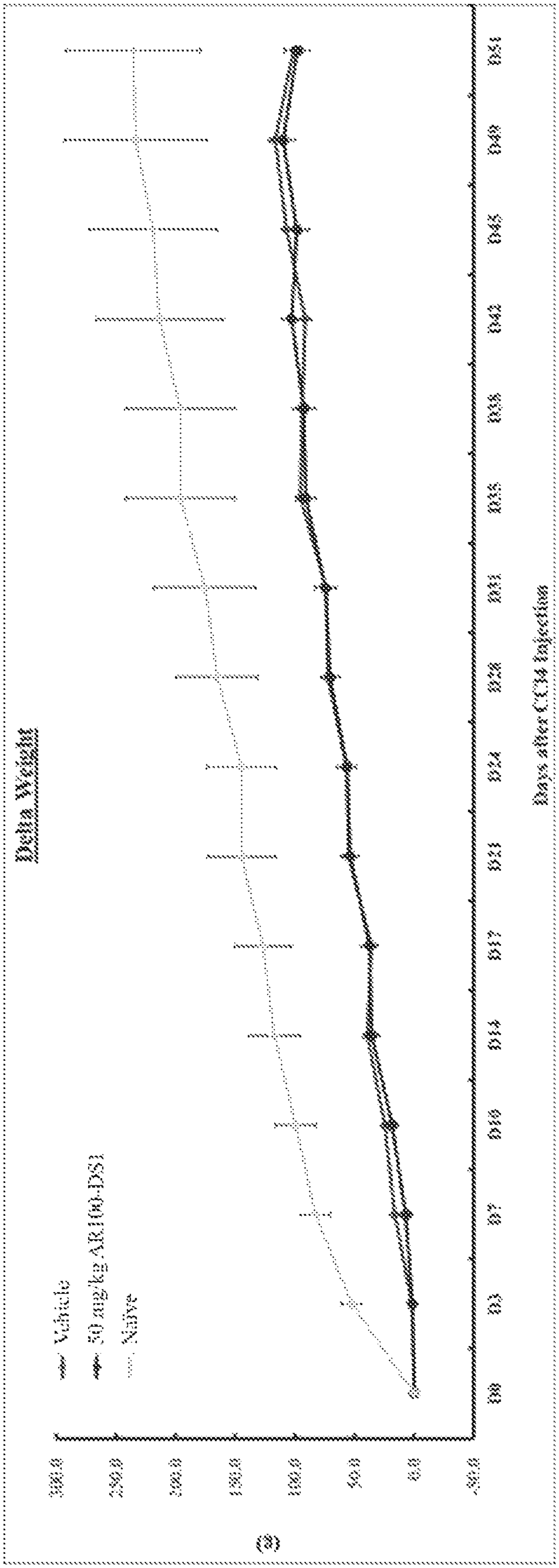
FIG. 7 depict (A)delta weight, (B)liver weight, and (C)liver/body-weight ratio, respectively.
Figure 7B:
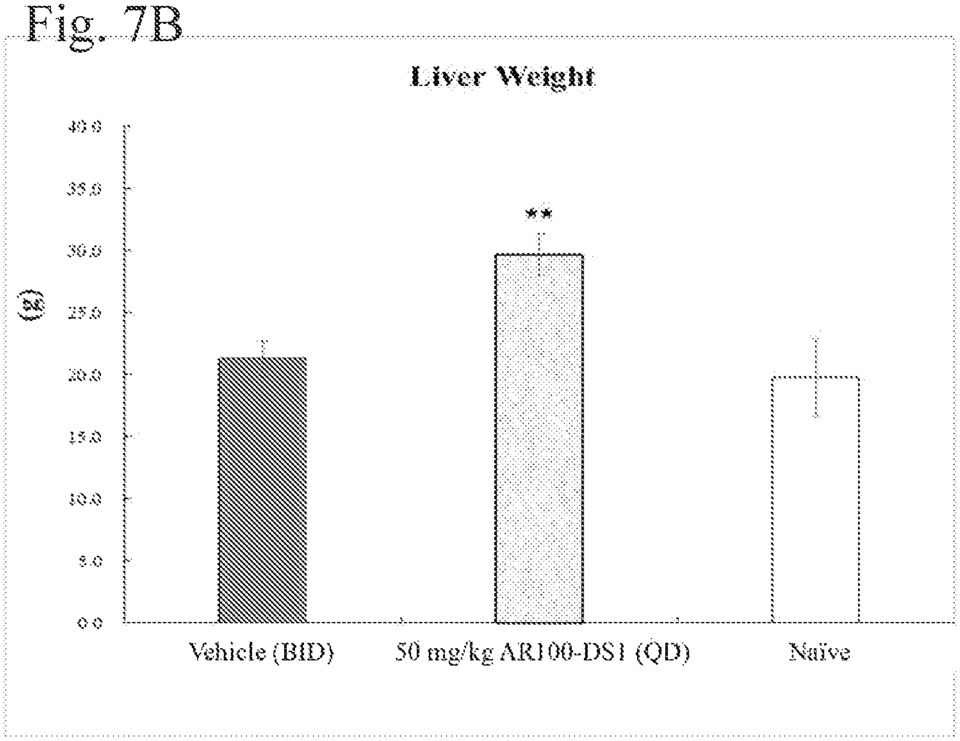
Figure 7C:
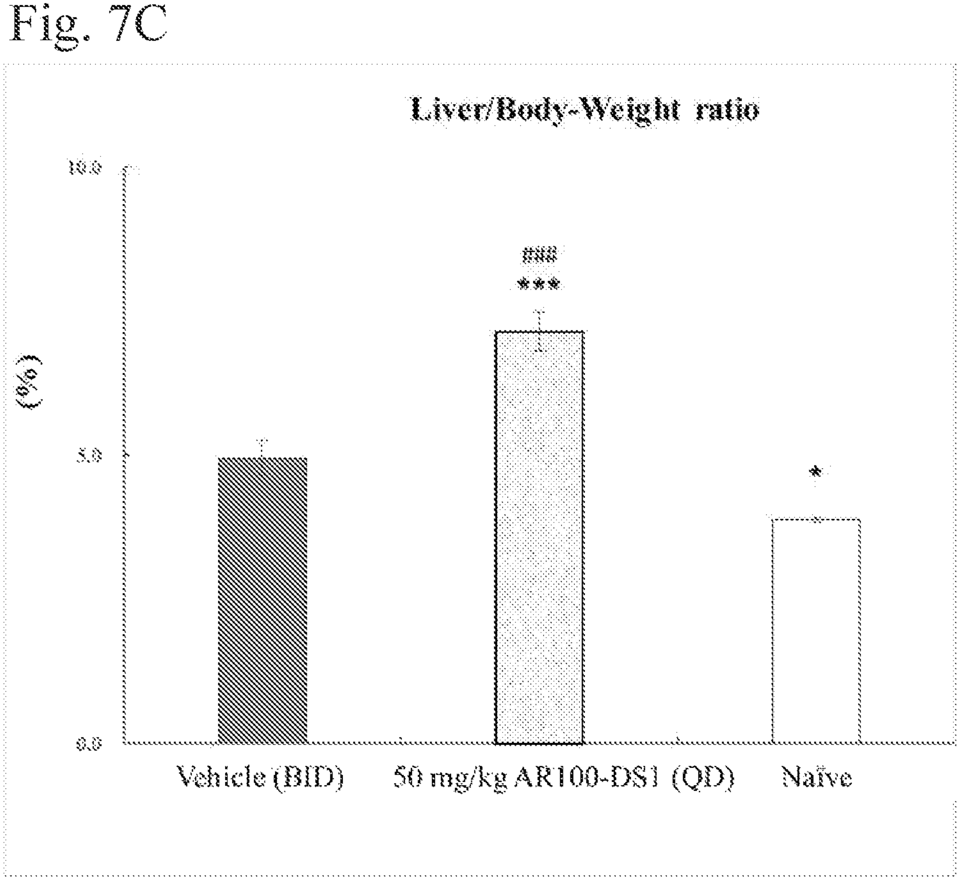

As shown in FIG. 6, eight-week-old male SD rats are administered $CCl_4$ at 0.4 mg/kg as twice per week for 8 weeks. Blood samples are collected at week 0, 2, 4, 6, and 8. The animals are sacrificed at the end of the 8-week for histopathological examinations. FIGS. 7A, 7B, 7C depict delta weight, liver weight, and liver/body-weight ratio, respectively. The liver weight of Naïve group is not significantly different from that of Vehicle group; however, the liver/body-weight ratio of Naïve group is significantly smaller than that of Vehicle group. The liver weight and liver/body-weight ratio of 50 mg/kg AR100-DS1 group are significantly larger comparing to that of Vehicle and Naïve group.

EXAMPLE 15

Serum Liver Enzymes Profile

Figure 8A:
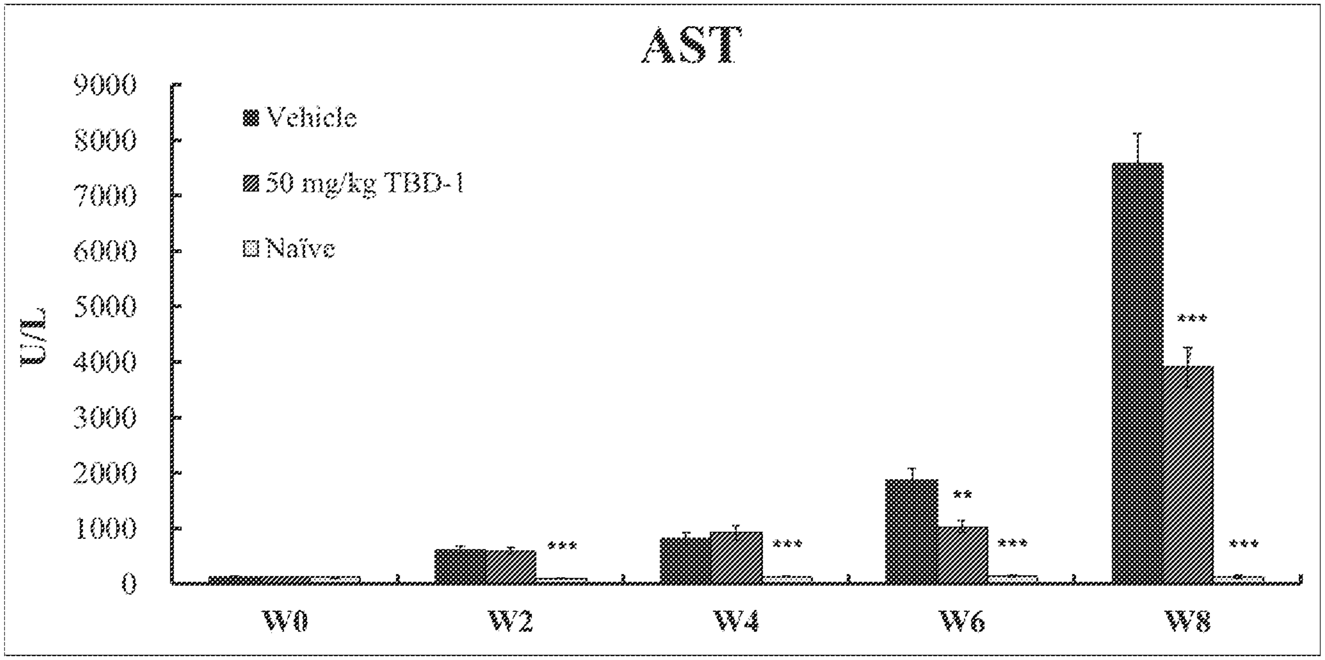
FIG. 8 depict serum levels of (A)AST, (B)ALT, and (C)AST/ALT respectively in rats following $CCl_4$-induced hepatic damage, FIG. 9 depict (A)inflammation, (B)vacuolation, (C)necrosis, (D)fibrosis, (E)total histological score in liver.
Figure 8B:
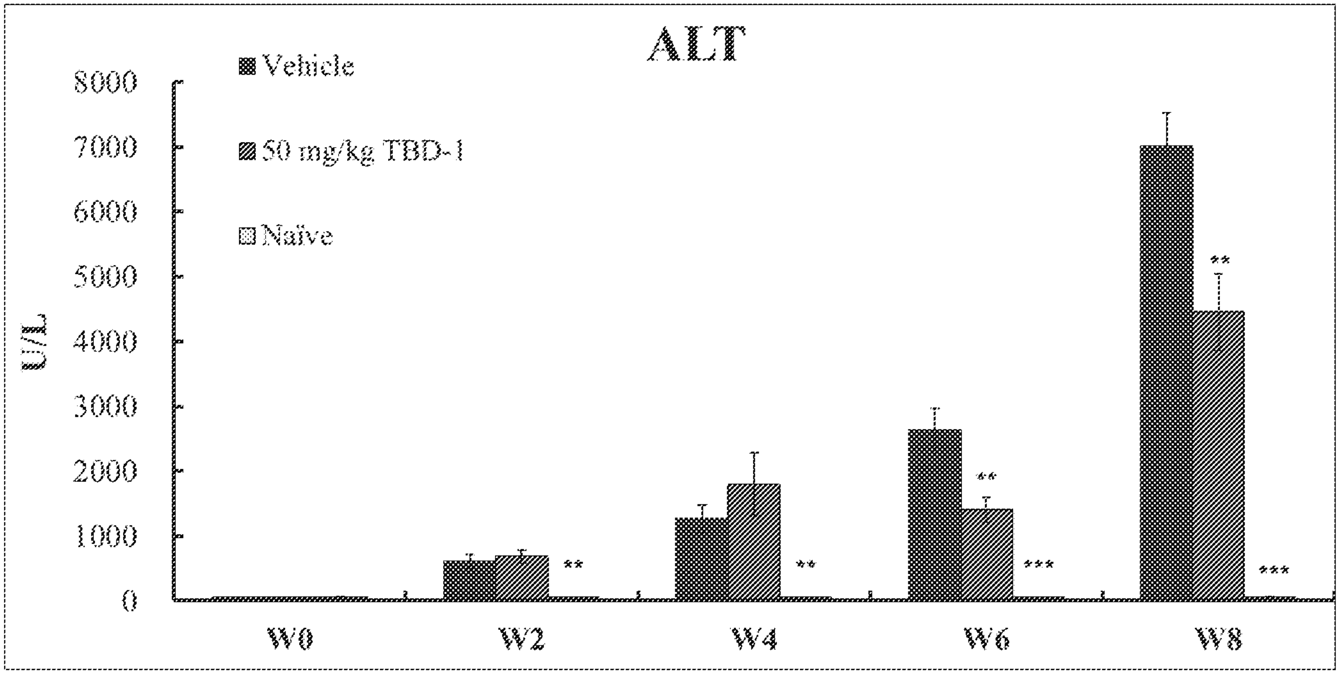
Figure 8C:
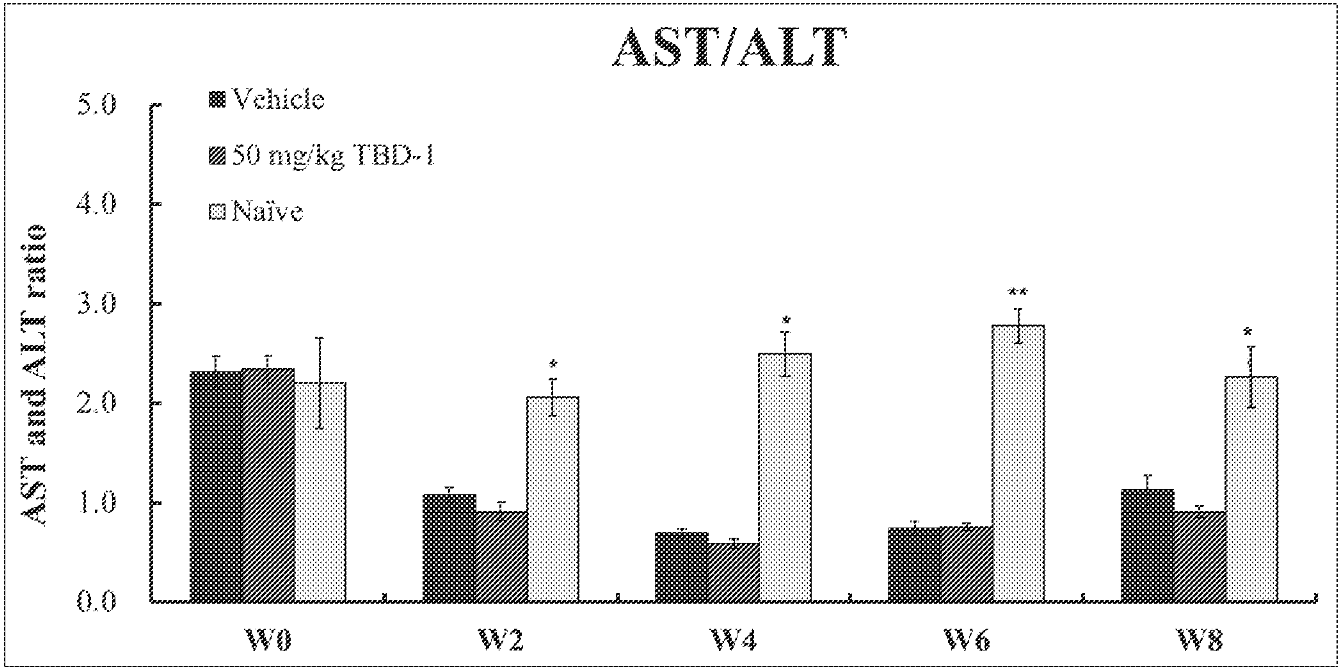
Figure 9A:
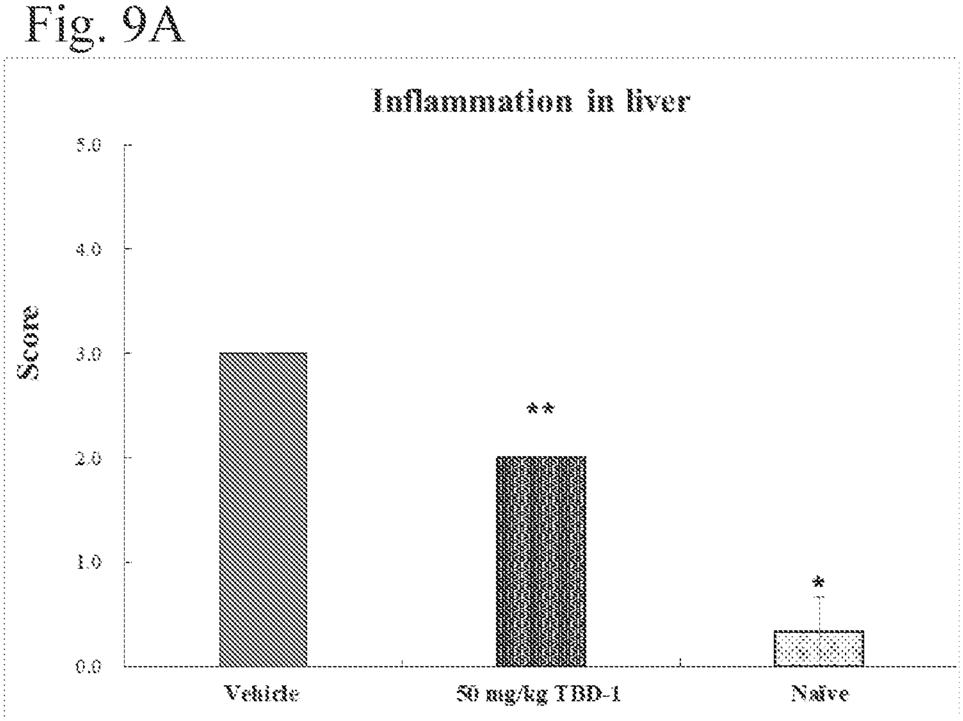
Figure 9B:
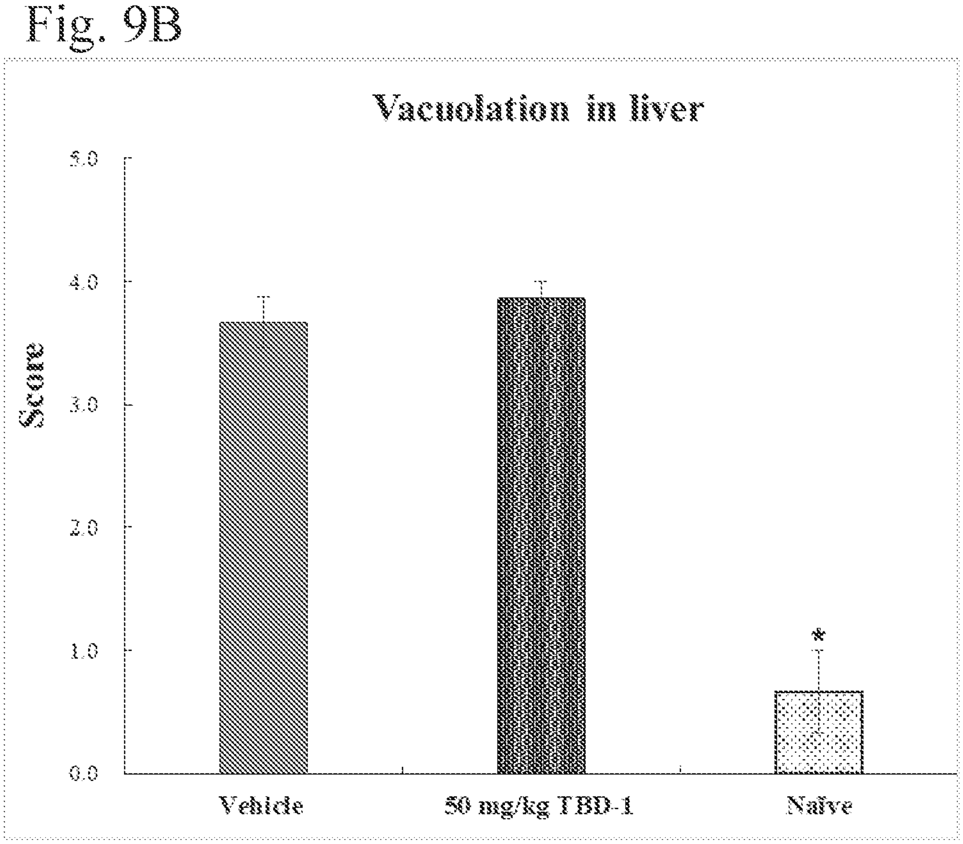
Figure 9C:
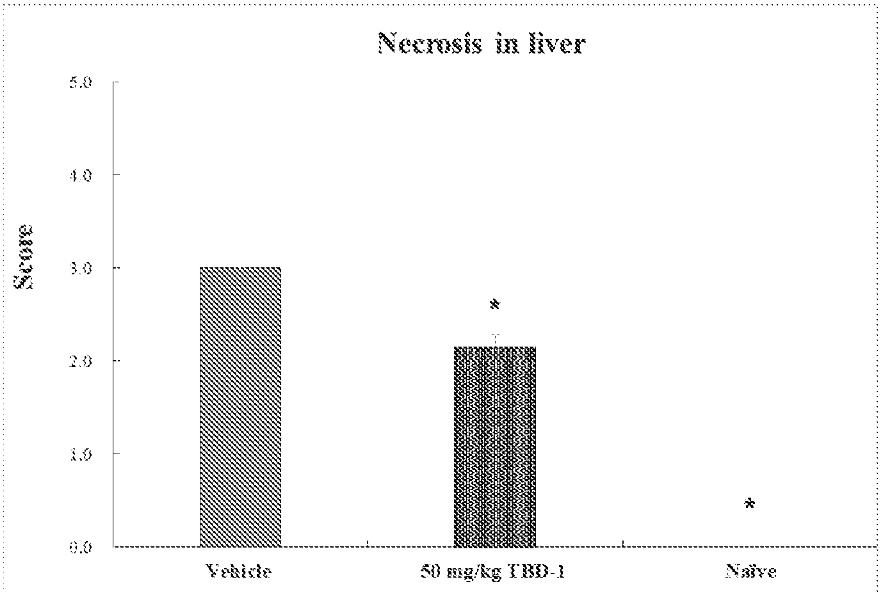
Figure 9D:
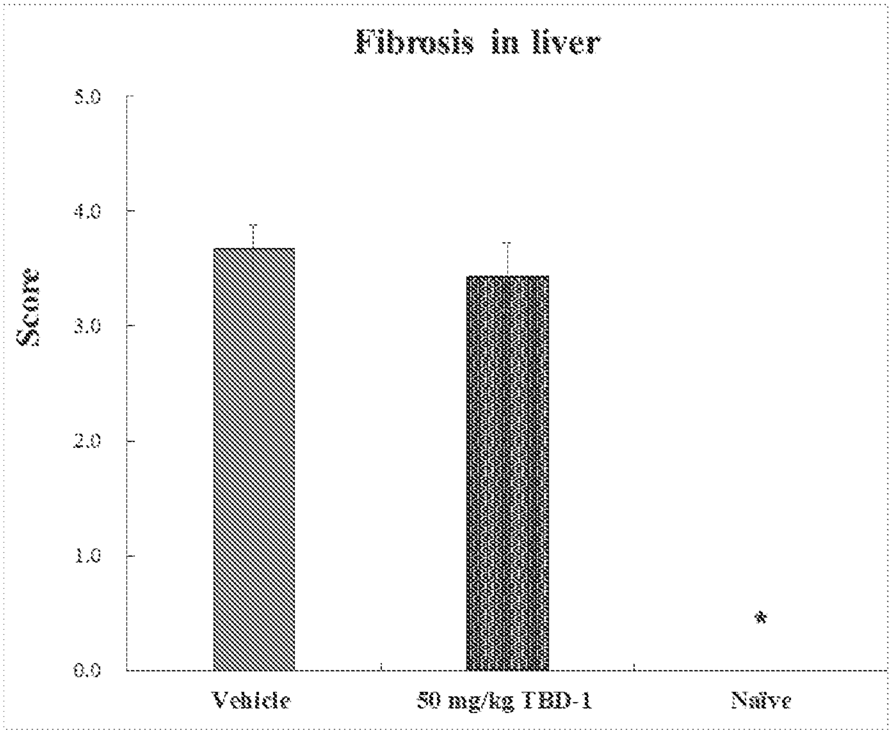
Figure 9E:
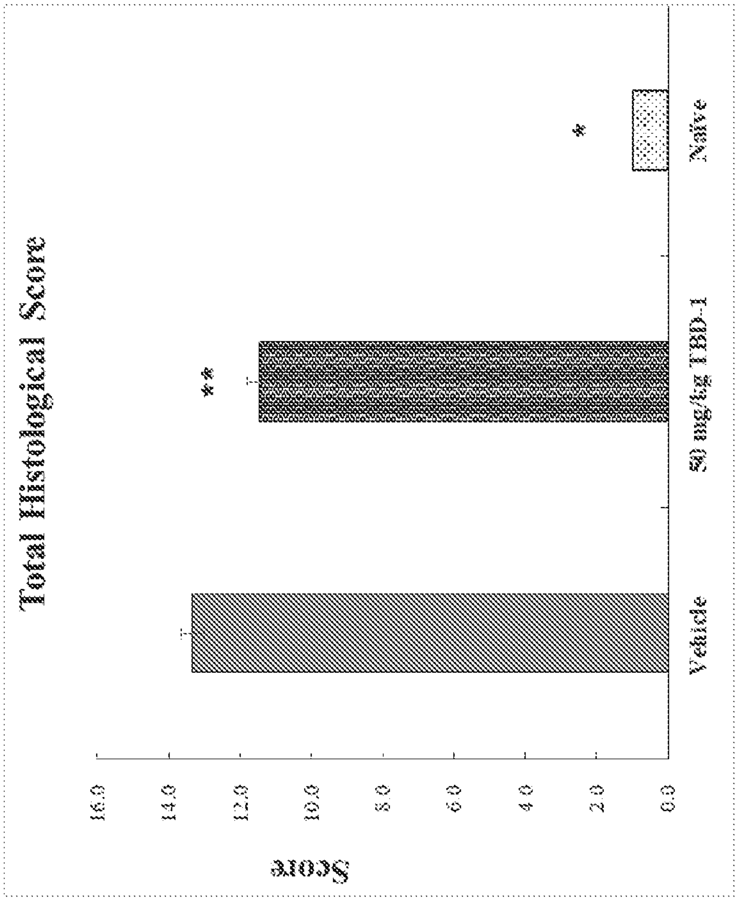
Figure 10:
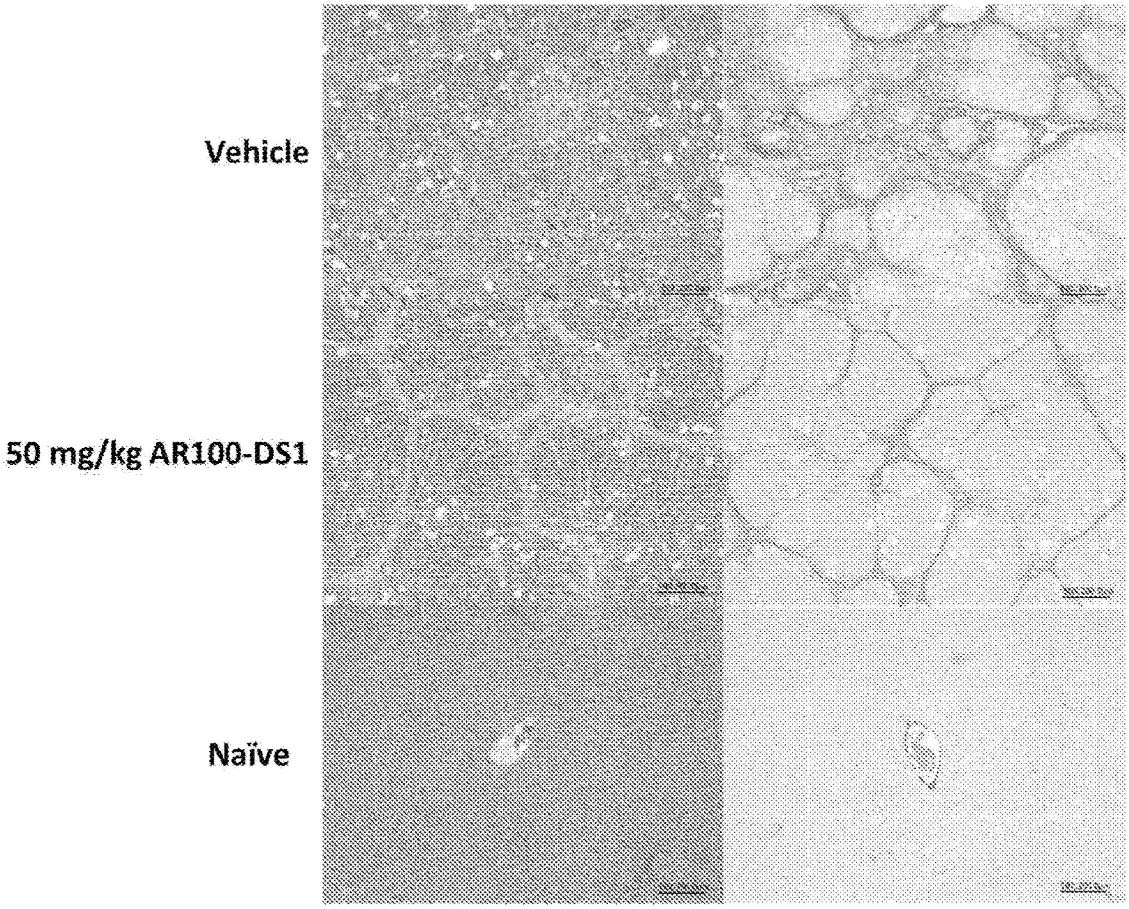
FIG. 10 Representative histological section of the liver is stained by H&E staining.

The level of clinical biochemistry such as aspartate aminotransferase (AST), alanine aminotransferase (ALT), is evaluated to determine the enzymatic activities of the livers of the control groups and the experimental groups (shown in FIGS. 8A-8C). The level of AST, ALT and AST/ALT ratio of Naïve group showed no significant changes during the experiment. The serum AST and AU level of the animals in each test group increased significantly with the progress of the experiment; however, compared with the vehicle group, less AST and ALT increases can be observed in the 50 mg/kg AR100-DS1 group at W6 and W8.

EXAMPLE 16

Liver Histological Evaluation

After 8 weeks of $CCl_4$ induction, the Vehicle group significantly suffered from liver injury such as increased AST and ALT, decreased AST/ALT ratio, inflammation, fibrosis, vacuolation and necrosis. As shown in FIGS. 9A-9E and 10, the liver of 50 mg/kg AR100-DS1 group has a smooth surface without atrophy and sclerosis, and the liver weight and liver/body weight-ratio are significantly larger than that of Vehicle and Naïve group. Overall, AR100-DS1 has been shown to have the potential to partially repair $CCl_4$-induced liver injury.

EXAMPLE 17

Effects of Ovatodiolide (AR100-DS1) on Con A (Concanavalin A) Induced Acute Hepatitis in BALB/c Mice Intravenous injection of concanavalin A (Con A) is a widely used strategy to study T cell mediated hepatitis. Con A is a lectin that can activate $CD4^+$ T cells, produce cytokines, and lead to liver cell damage. Dexamethasone (Dex) is a long acting synthetic corticosteroid, and has been used as anti-inflammatory and immunosuppressive medication. The effects of Ovatodiolide (AR100-DS1) on serum glutamic-pyruvic transaminase (GOT), glutamic-oxaloacetic transaminase (GPT), circulating cytokines and liver histopathology on Con A-induced acute hepatitis are evaluated in BALB/c mice.

Con A and Dex were purchased from Sigma Aldrich (USA). ProcartaPlex™ immunoassays kit was purchased from Corning Inc. (USA). GOP and GPT Fuji Dri-Chem slides were purchased from Winning Medical Inc. (Taiwan).

Male BALB/c mice (7-9 weeks old) were purchased from BioLASCO Taiwan Co., Ltd or National Laboratory Animal Center (NLAC, Taiwan). Animals are housed five per cage with food and water provided ad libitum throughout the experiments. Room temperature is maintained at 23±2° C. with an alternating 12 h light dark cycle. Animals are acclimatized for one week to minimize the effect of stress before the experiments. All experimental protocols involving animals and their care are approved by the Institutional Animal Care and Use Committee (IACUC) in ITRI (ITRI-IACUC-2018-041 and ITRI-IACUC-2018-050; accredited by AAALAC) and are carried out according to the regulations of the Council of Agriculture, Taiwan.

Figure 11:
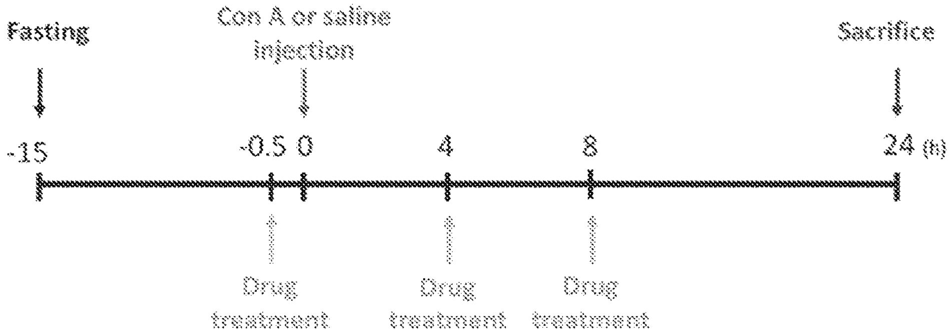
FIG. 11 depicts the process of Con A (concanavalin A) induced acute hepatitis model.

Con A is dissolved in pyrogen free saline at a concentration of 3 mg/mL and intravenously injected at a dose of 15 mg/kg or 20 mg/kg of body weight to induce hepatitis. Ovatodiolide (AR100-DS1) and Dex are orally administered 30 min before and then 4 h and 8 h after Con A treatment. Blood and liver tissues are collected 24 h after Con A treatment (FIG. 11). Serum are stored at 80° C. until analysis.

Figures 12A, 12B, 12C:
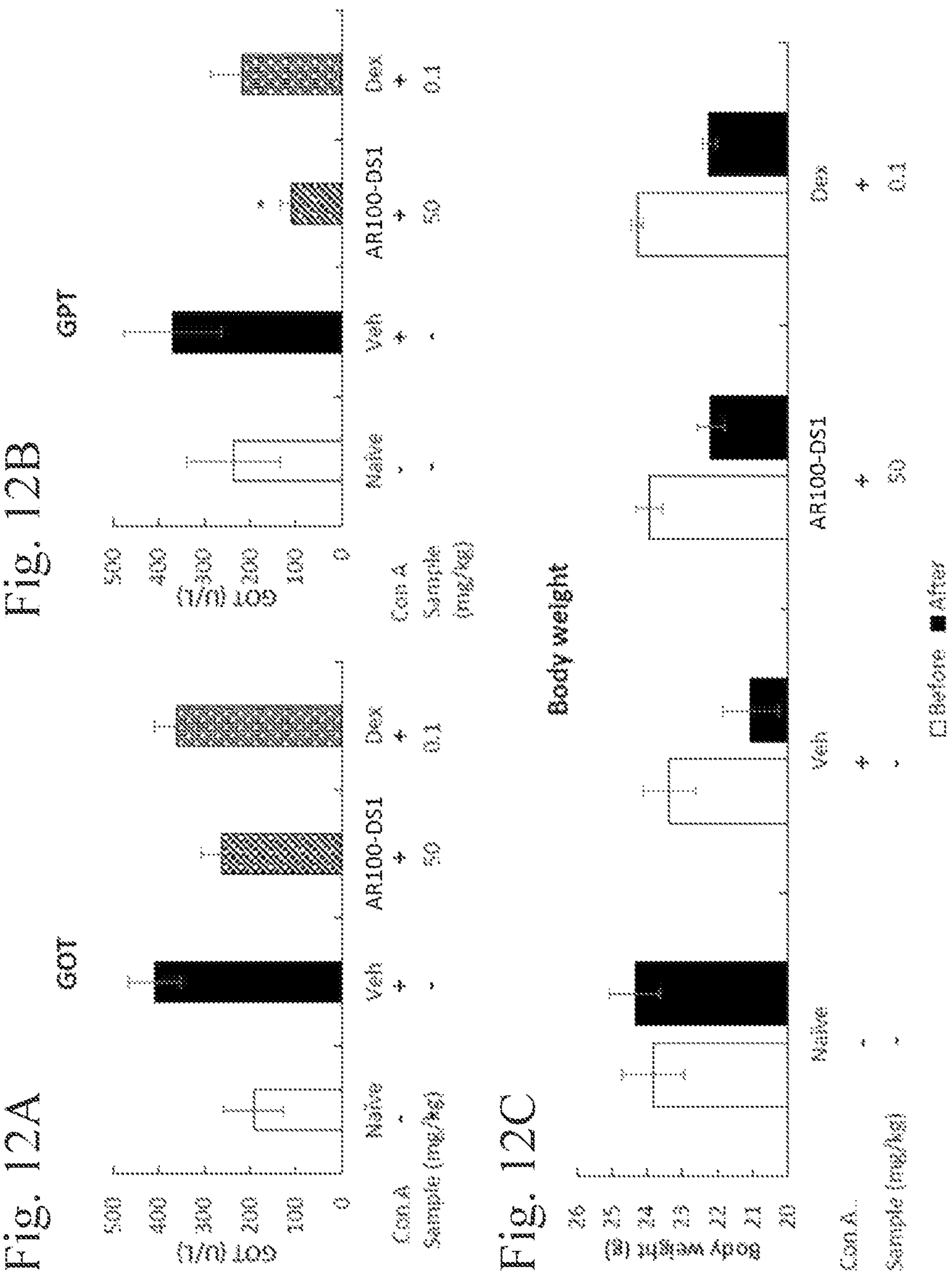
FIG. 12 depict the process of Ovatodiolide (AR100-DS1) on GOT, GPT and body weight. (A) Serum GOT and (B) serum GPT 24 h after 15 mg/kg Con A challenge. (C) body weight before and after 15 mg/kg Con A challenge. Data are presented as mean SEM (n=9). p<0.05 versus Veh by the t test. Veh, vehicle; Dex, dexamethasone.

To assess the level of hepatocellular injury after Con A treatment, serum GPT and GOT levels are measured by Fuji Dri-Chem slides (Fuji, Japan). The serum of the same group is pooled for cytokine assay. Cytokine levels are measured by ProcartaPlex™ immunoassays kit according to manufacturer's instructions. Data are presented as mean±SEM. T test is used to analyze the differences between drug and vehicle treated groups. The difference is regarded statistically significant when p value is less than 0.05. Ovatodiolide (AR100-DS1) at 50 mg/kg significantly reduced GPT level that is increased by Con A (109±25 vs 368±107 U/L, $p<0.05$) and slightly improved elevation of GOT (261±45 vs 410±56 U/L) (FIG. 12).

Figure 13:
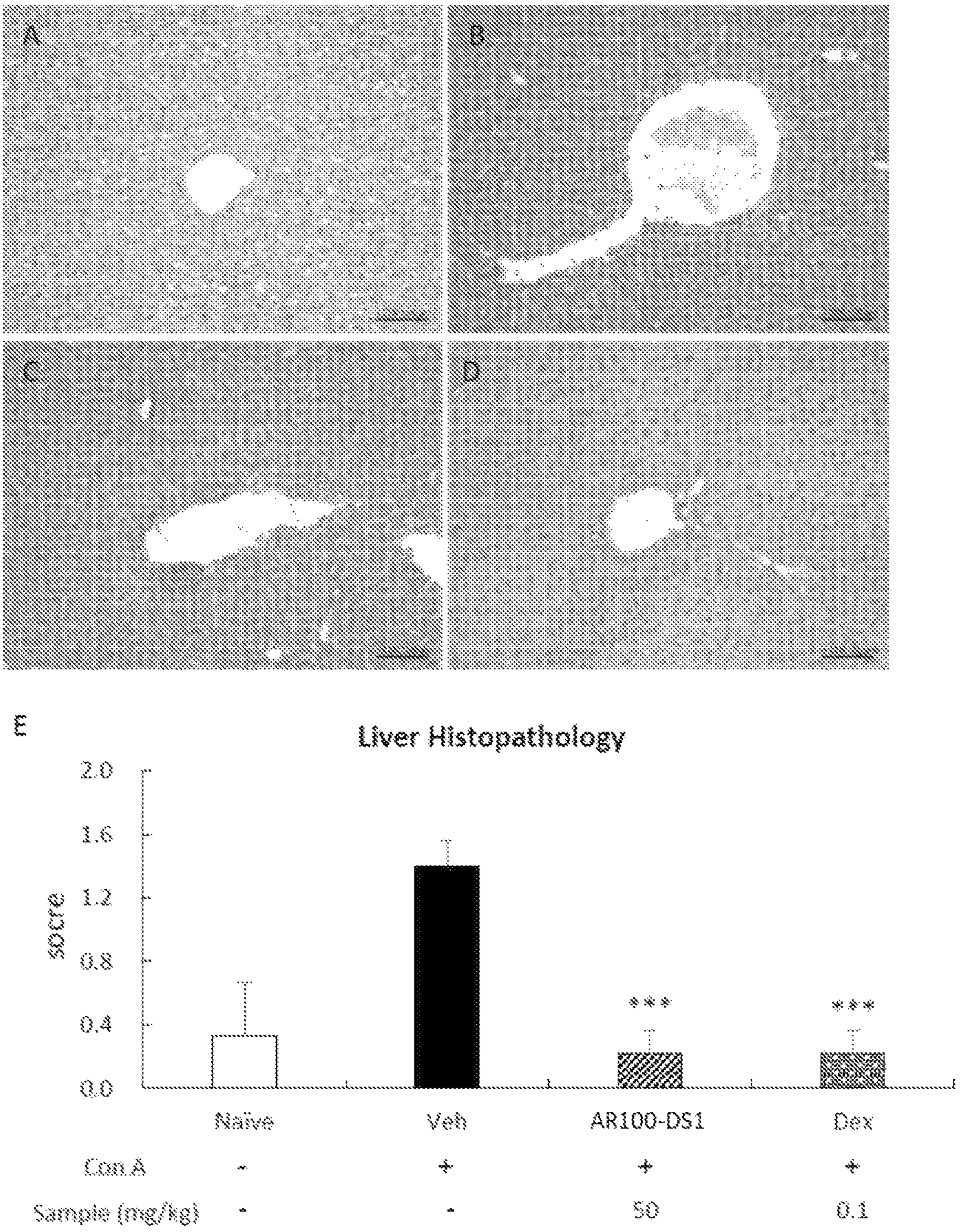
FIG. 13 Effects of Ovatodiolide (AR100-DS1) on liver injury. Liver histopathology of (A) Naïve, (B) 15 mg/kg Con A (Veh), (C) 2019-0321-1 and (D) dexamethasone, and (E) histopathological scores of necrosis. Data are presented as mean±SEM (n=9). ***p<0.001 versus Veh by the Student's t test. Veh, vehicle; Dex, dexamethasone.

Liver tissues are fixed in 10% phosphate buffered formaldehyde, embedded in paraffin, and stained with hematoxylin and eosin (H&E) in order to confirm tissue lesions. Tissue lesions are examined microscopically by a veterinary pathologistat BioLASCO Taiwan Co., Ltd. The criteria of severity grading system for all microscopic lesions are graded from 0 to 4 as follows: 0=none; 1=individual cell necrosis; 2=≤30% lobular necrosis; 3=≤60% lobular necrosis; 4=>60% lobular necrosis. The histopathological analysis showed Ovatodiolide (AR100-DS1) ameliorated liver necrosis (score 0.2±0.2 vs 1.4±0.2, $p<0.05$) (FIG. 13), The results show that ovatodiolide (AR100-DS1) reduced serum GOP and GPT and attenuated Con A induced liver necrosis.

EXAMPLE 18

Figure 14:
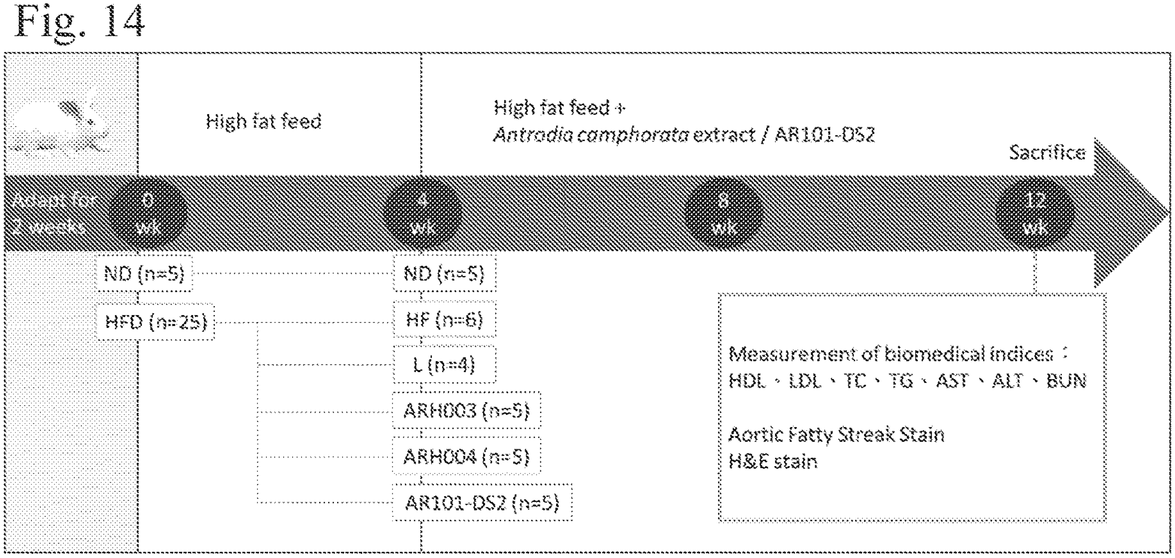
FIG. 14 depicts the process of atherosclerosis rabbit model.
Figure 15:
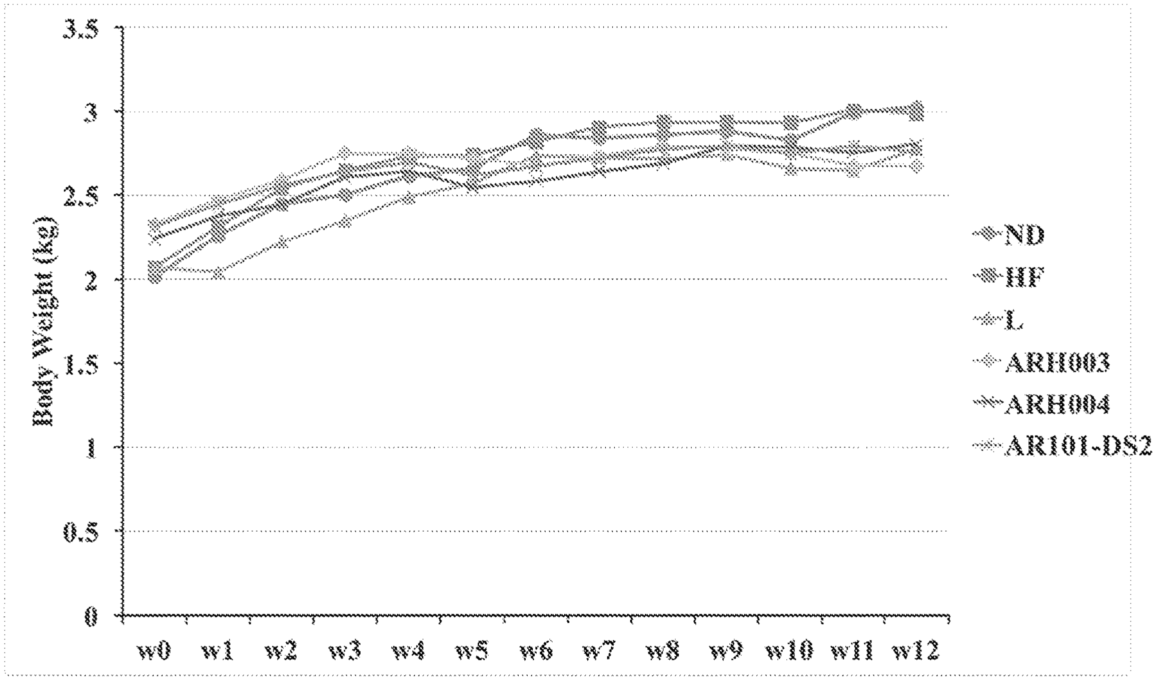
FIG. 15 depicts initial and final average body weight of rabbits. † and * indicate a P<0.05 as compared with the control group and FT group, respectively.
Figure 16B:
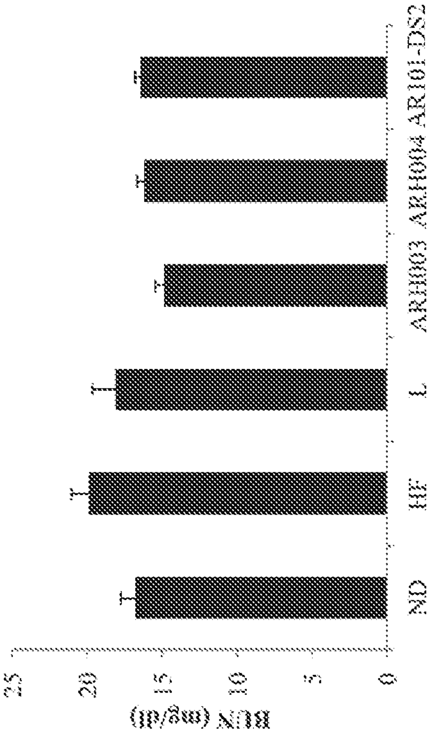
FIG. 16 depict changes in AST, ALT, BUN between WO groups in each group of rabbits † and * indicate a P<0.05 as compared with the control group and HF group, respectively.
Figure 16A:
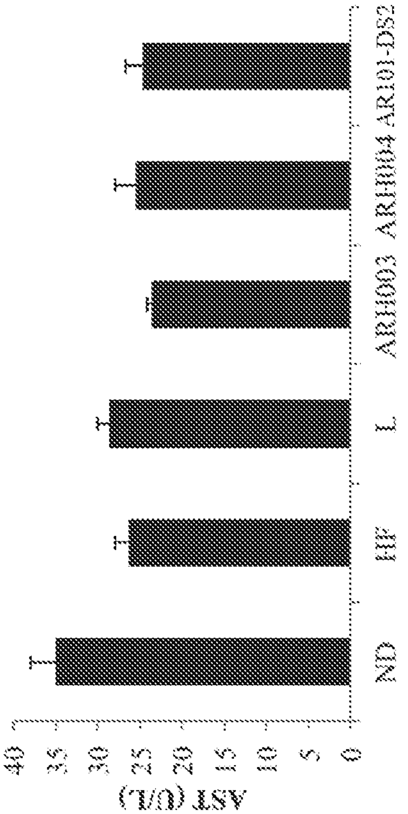
Figure 16C:
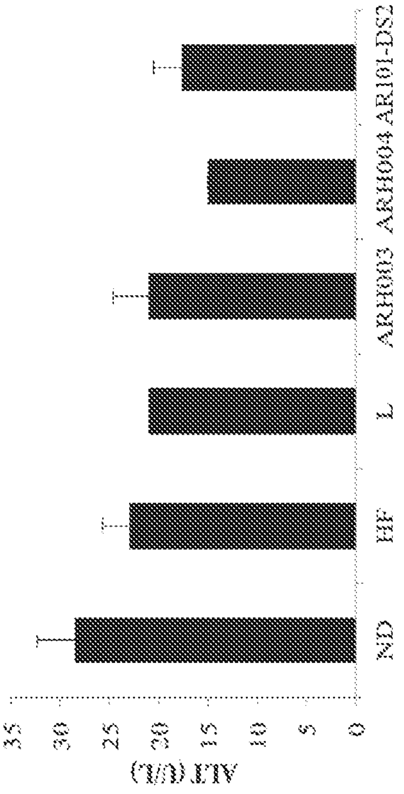
Figures 17A, 17B, 17C, 17D:
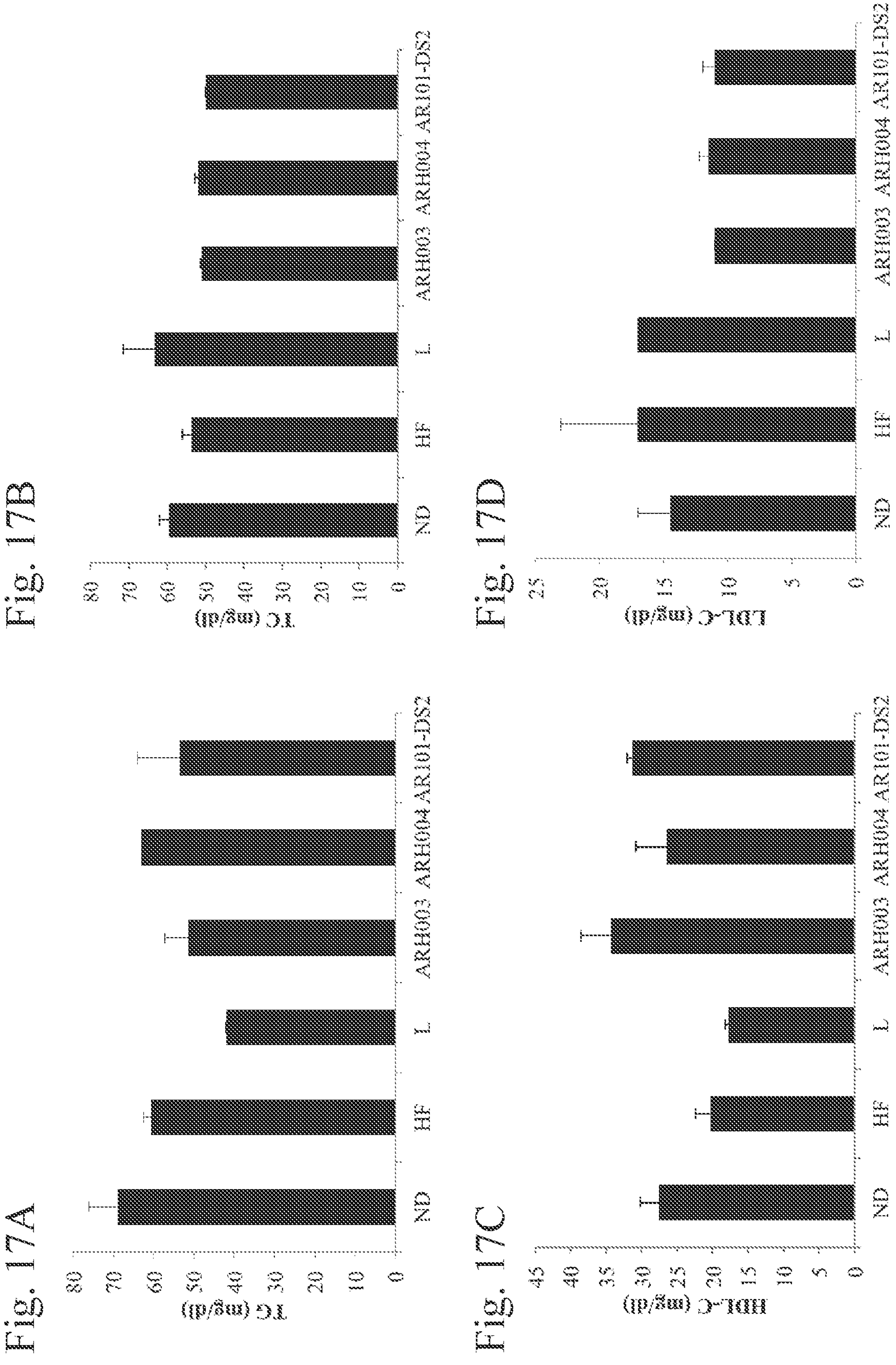
FIG. 17 depict changes in TG, TC, HDL-C, IDL-C between WO groups in each group of rabbits † and * indicate a P<0.05 as compared with the control group and HF group, respectively.
Figure 18B:
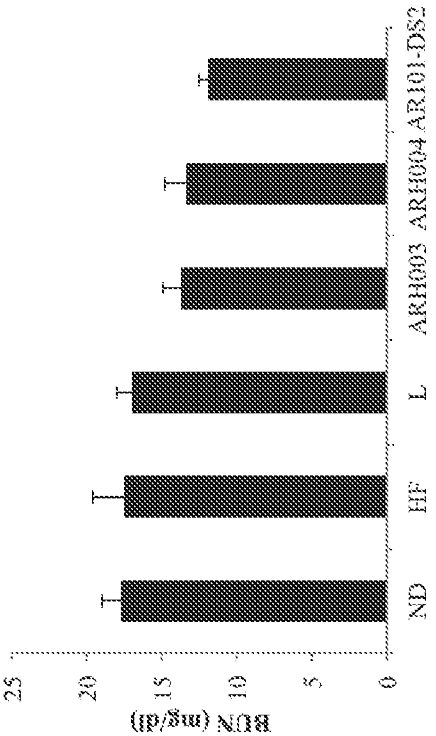
FIG. 18 depict changes in AST, ALT, BUN between W4 groups in each group of rabbits † and * indicate a P<0.05 as compared with the control group and HF group, respectively.
Figure 18A:
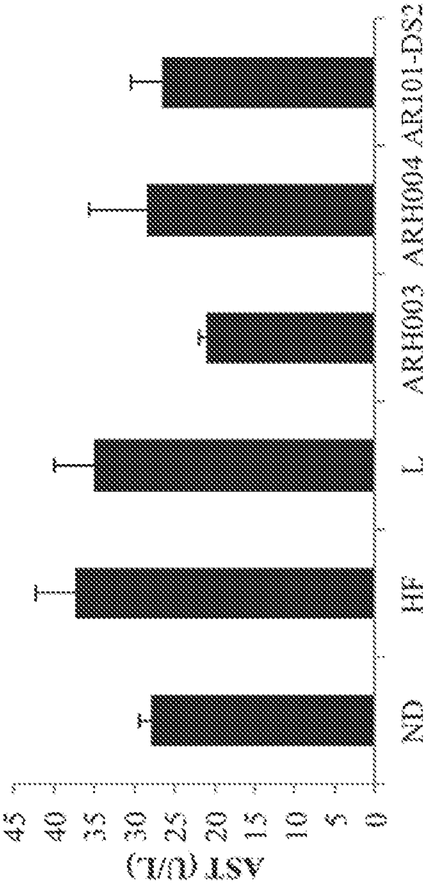
Figure 18C:
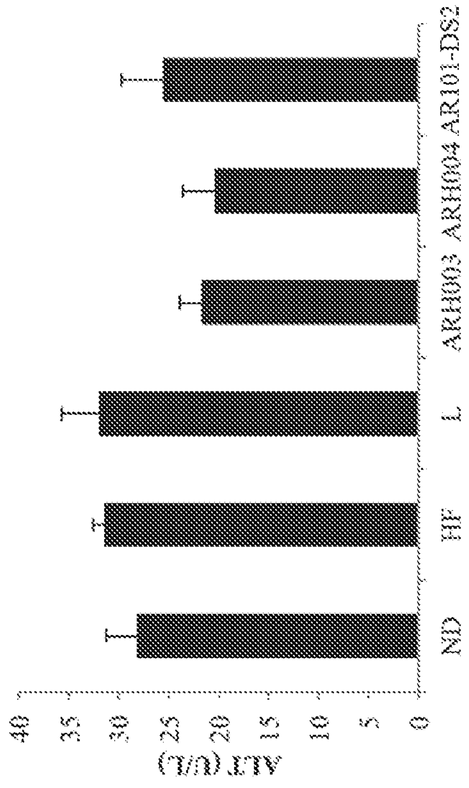
Figure 19A:
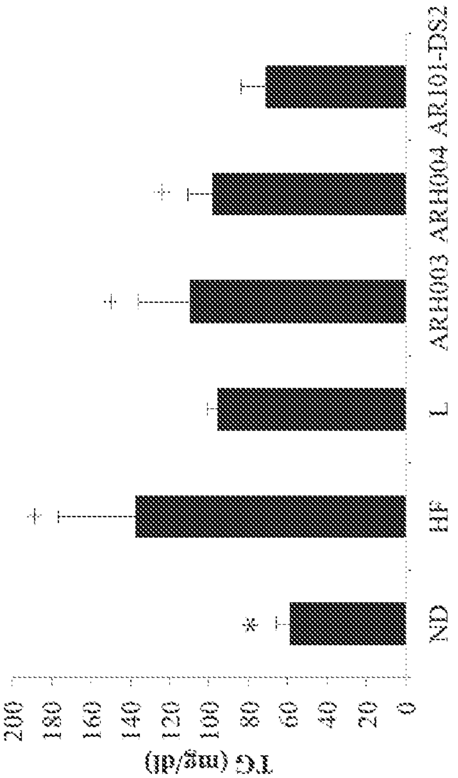
FIG. 19 depict changes in TG, TC, HDL-C, LDL-C between W4 groups in each group of rabbits. † and * indicate a P<0.05 as compared with the control group and HF group, respectively, FIG. 20 depict changes in AST, ALT, BUN between W8 groups in each group of rabbits † and * indicate a P<0.05 as compared with the control group and HF group, respectively.
Figure 19B:
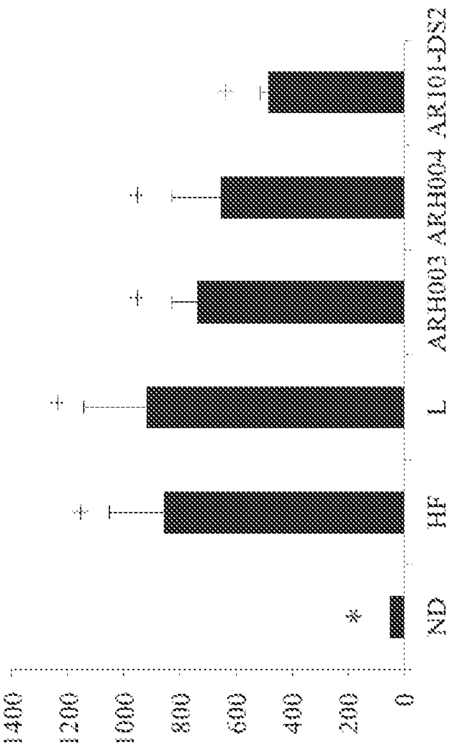
Figure 19C:
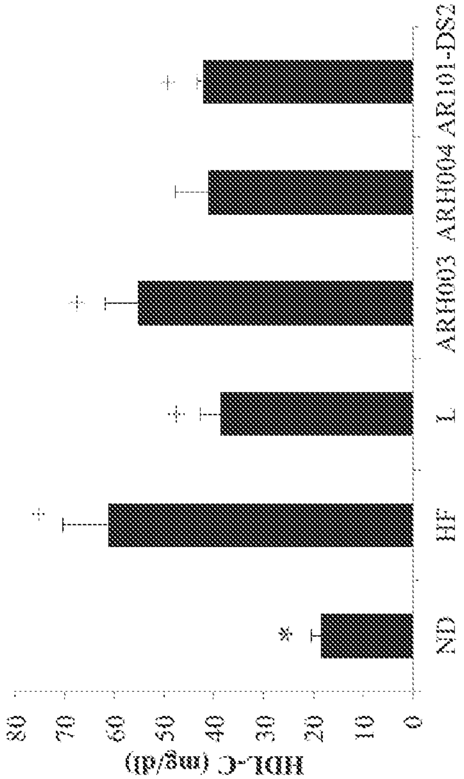
Figure 19D:
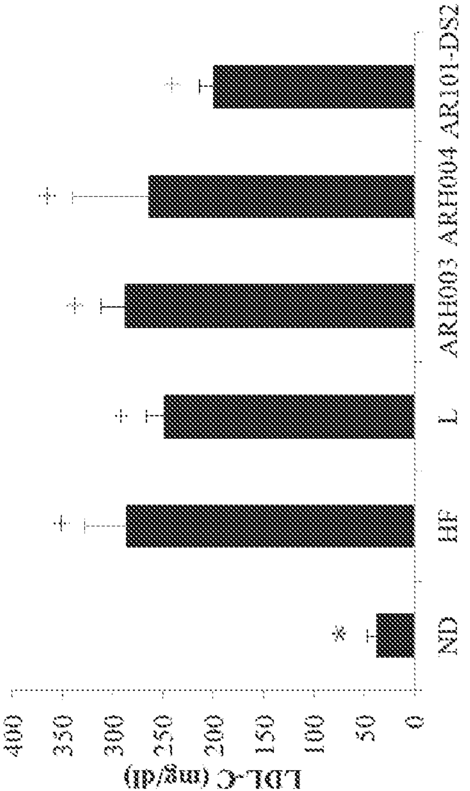
Figure 20A:
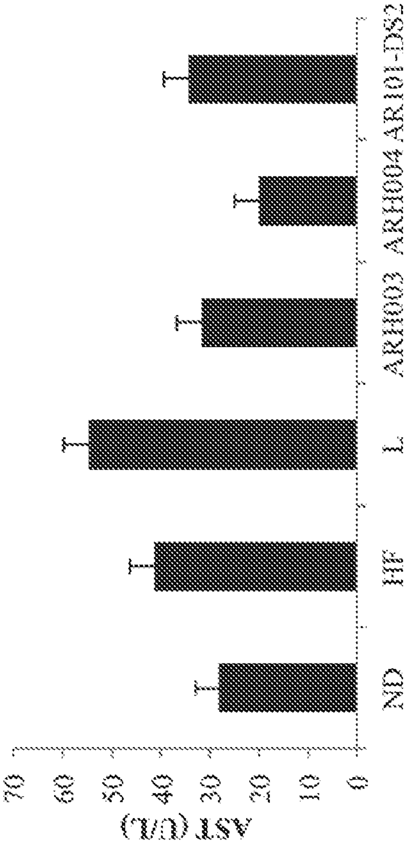
Figure 20B:
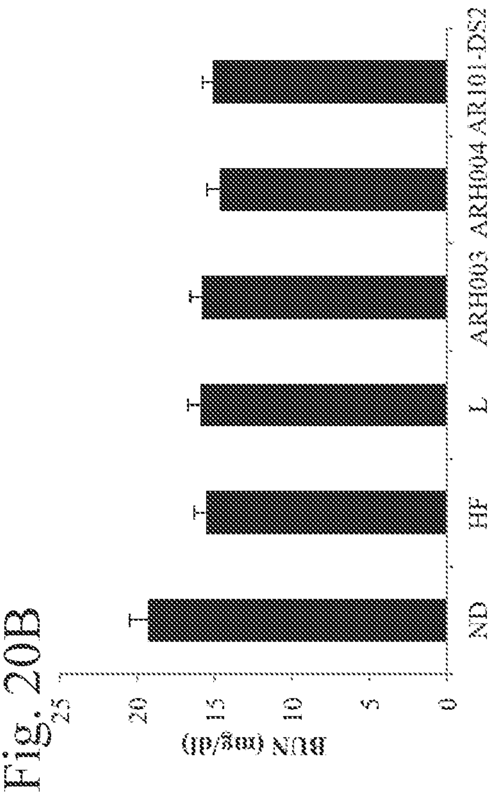
Figure 20C:
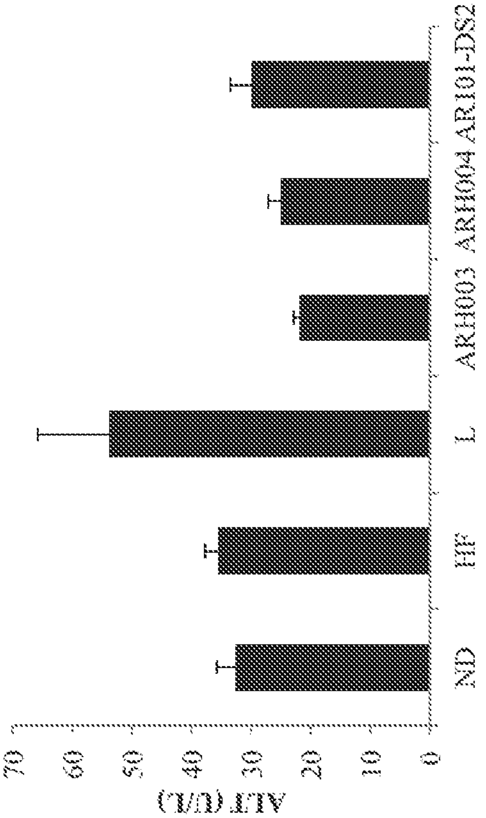
Figure 21A:
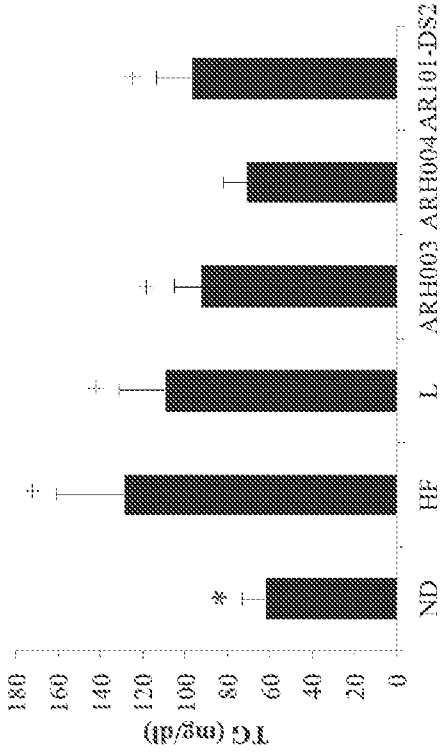
FIG. 21 depict changes in TG, TC, HDL-C, LDL-C between W8 groups in each group of rabbits. † and * indicate a P<0.05 as compared with the control group and HF group, respectively.
Figure 21B:
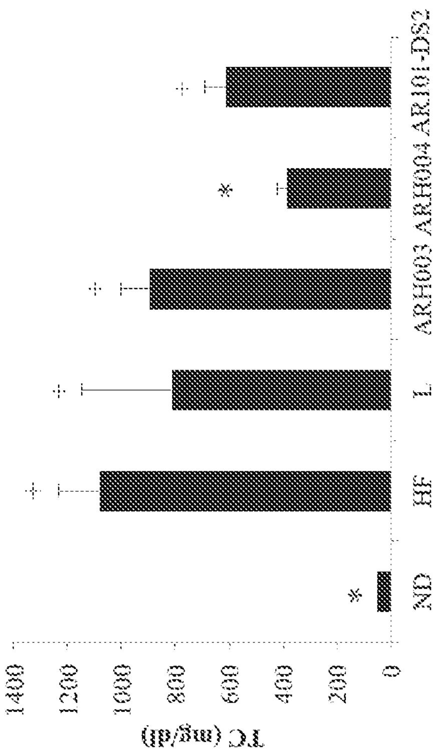
Figure 21C:
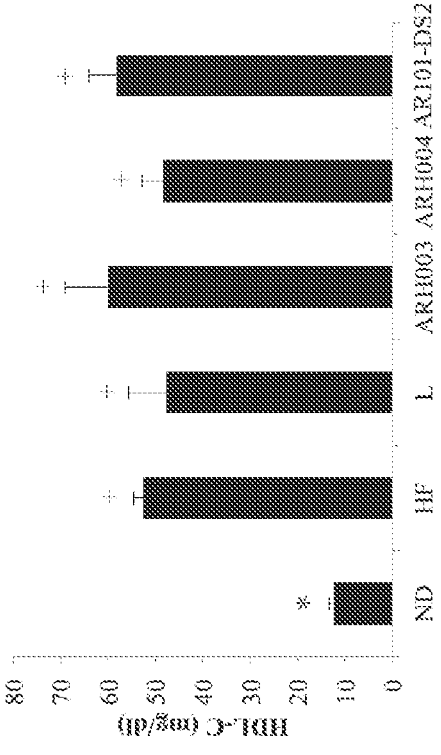
Figure 21D:
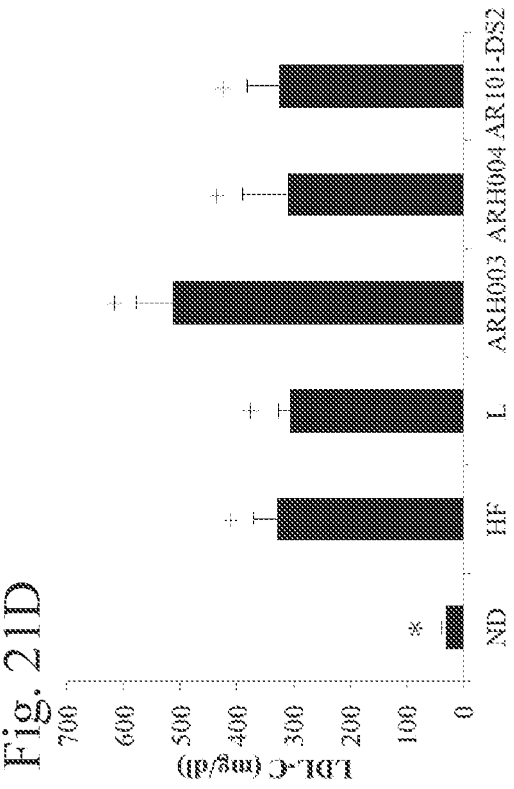
Figure 22B:
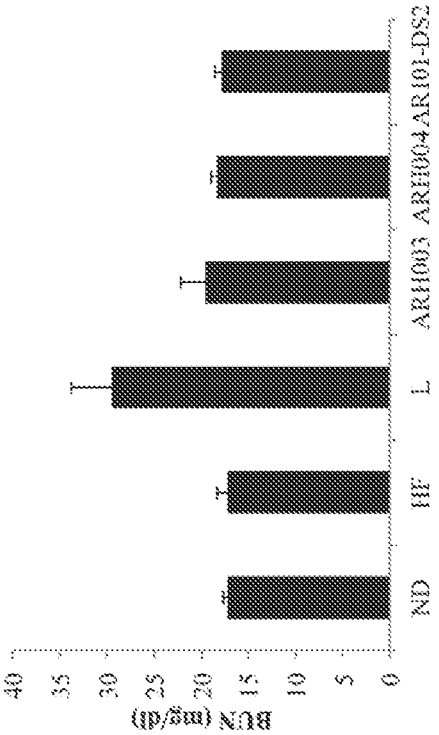
FIG. 22 depict changes in AST, ALT, BUN between W12 groups in each group of rabbits † and * indicate a P<0.05 as compared with the control group and HF group, respectively.
Figure 22A:
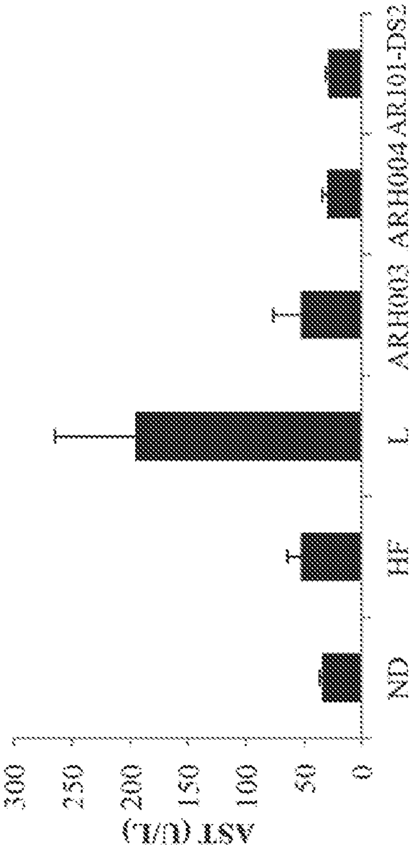
Figure 22C:
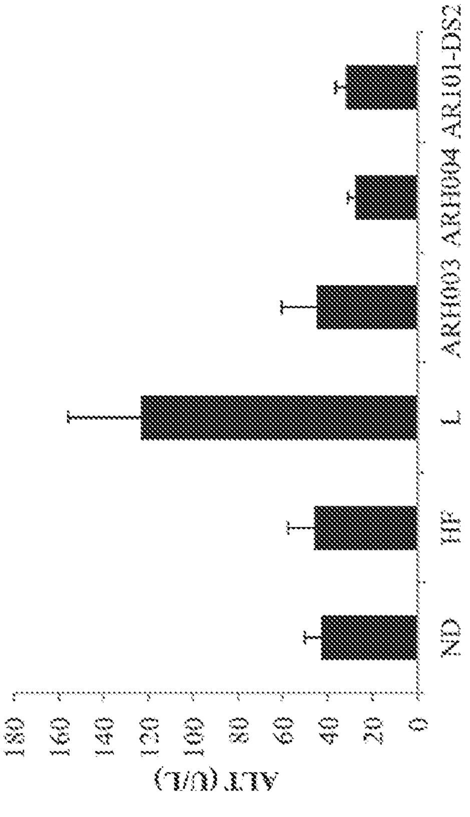
Figure 23A:
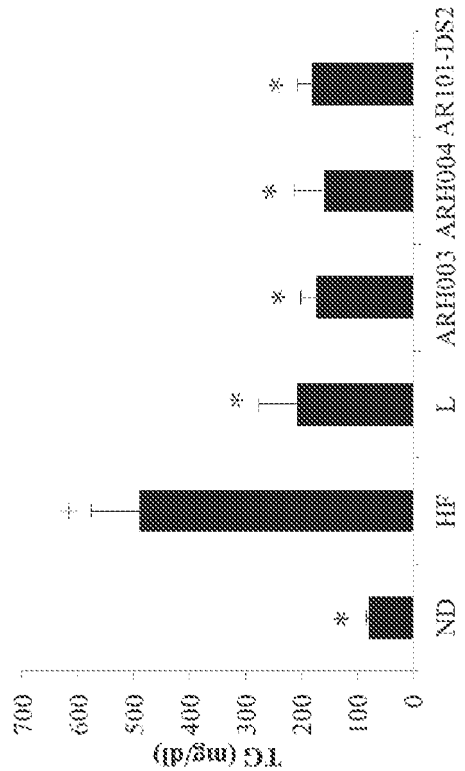
FIG. 23 depict changes in TG, TC, HDL-C, LDL-C between W12 groups in each group of rabbits. † and * indicate a P<0.05 as compared with the control group and HF group, respectively.
Figure 23B:
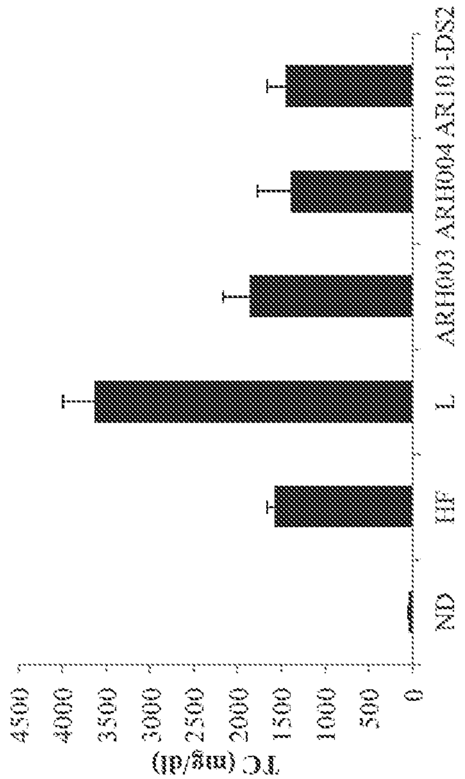
Figure 23C:
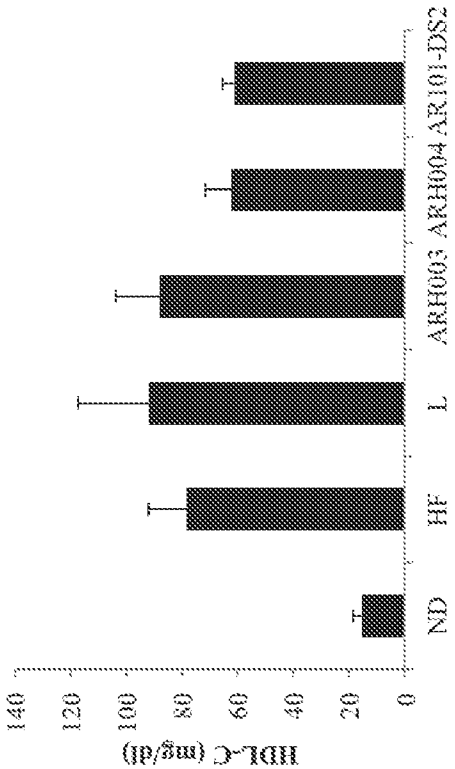
Figure 23D:
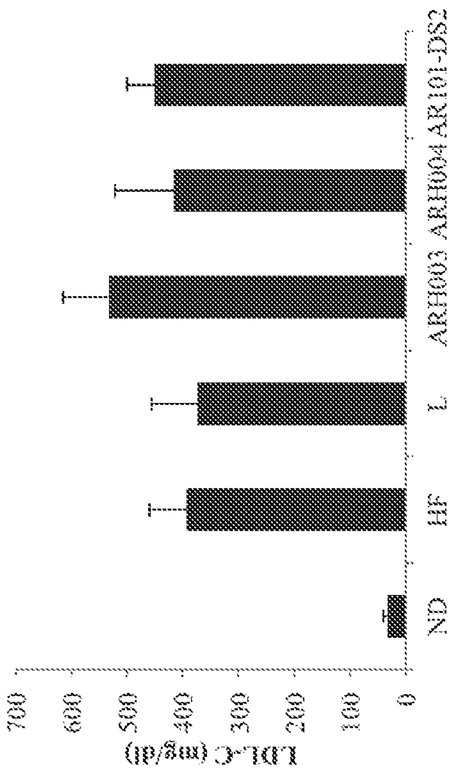

Evaluation of the Efficacy of *Antrodia camphorata* Extract and AR101-DS2 in Preventing Atherosclerosis and Liver Fibrosis Experimental Model 2 to 3 kg male, New Zealand White rabbits are individually caged and housed in temperature and humidity-controlled rooms. Light-dark cycles are 12 h each. After several days of acclimation, the animals are sequentially assigned to six feeding groups: standard rabbit chow, standard rabbit chow containing 0.5% cholesterol, standard rabbit chow containing both 0.5% cholesterol and 10 mg/kg Lovastatin, standard rabbit chow containing both 0.5% cholesterol and 1% ARH003, standard rabbit chow containing both 0.5% cholesterol and 1% ARH004, standard rabbit chow containing both 0.5% cholesterol and 10 mg/kg AR101-DS2. Except standard rabbit chow, others groups are given standard rabbit chow containing 0.5% cholesterol for 4 weeks (see FIGS. 14-15). The daily feeding amount for each rabbit is 50 g/kg body weight per day. Diets are administered for 8 weeks, after the animals had adjusted to their new environment. At the beginning and end of the 12 weeks study, the rabbits are anesthetized by an intramuscular injection of Zoletil 50 (1 mL/kg) (Virbac Ltd., France), and blood samples are harvested. Finally, the aortas (from aortic arch to the bifurcation of the iliac arteries) and whole livers are collected from the rabbits after they are sacrificed for further histopathological analyses.

2 to 3 kg male, New Zealand White rabbits (n=30) are divided into the following groups:

(ND) standard rabbit chow, n=5;

(HF) standard rabbit chow containing 0.5% cholesterol, n=6;

(L) standard rabbit chow containing both 0.5% cholesterol and 10 mg/kg Lovastatin, n=4;

(AR003) standard rabbit chow containing both 0.5% cholesterol and 1% ARH003, n=5;

(AR004) standard rabbit chow containing both 0.5% cholesterol and 1% ARH004, n=5;

(AR101-DS2) standard rabbit chow containing, both 0.5% cholesterol and 10 mg/kg AR101-DS2, n=5;

The daily feeding amount for each rabbit is 50 g/kg body weight per day.

Blood Chemistry Analysis

The animals are fasted overnight before blood drawing. The blood is collected from the marginal ear veins of rabbits into BI) Vacutainer EDTA Blood Collection Tubes, Plasma is separated by centrifugation at 3,000 rpm at 4° C. for 10 min. FIGS. 16-23 depict measurements for changes in blood chemistry parameters included serum levels of low-density lipoprotein (LEK), cholesterol (Choi), triglycerides (TG), glutamate oxaloacetate transaminase (GOT), and glutamate pyruvate transaminase (GPT).

Aortic Fatty Streak Staining

Figure 24:
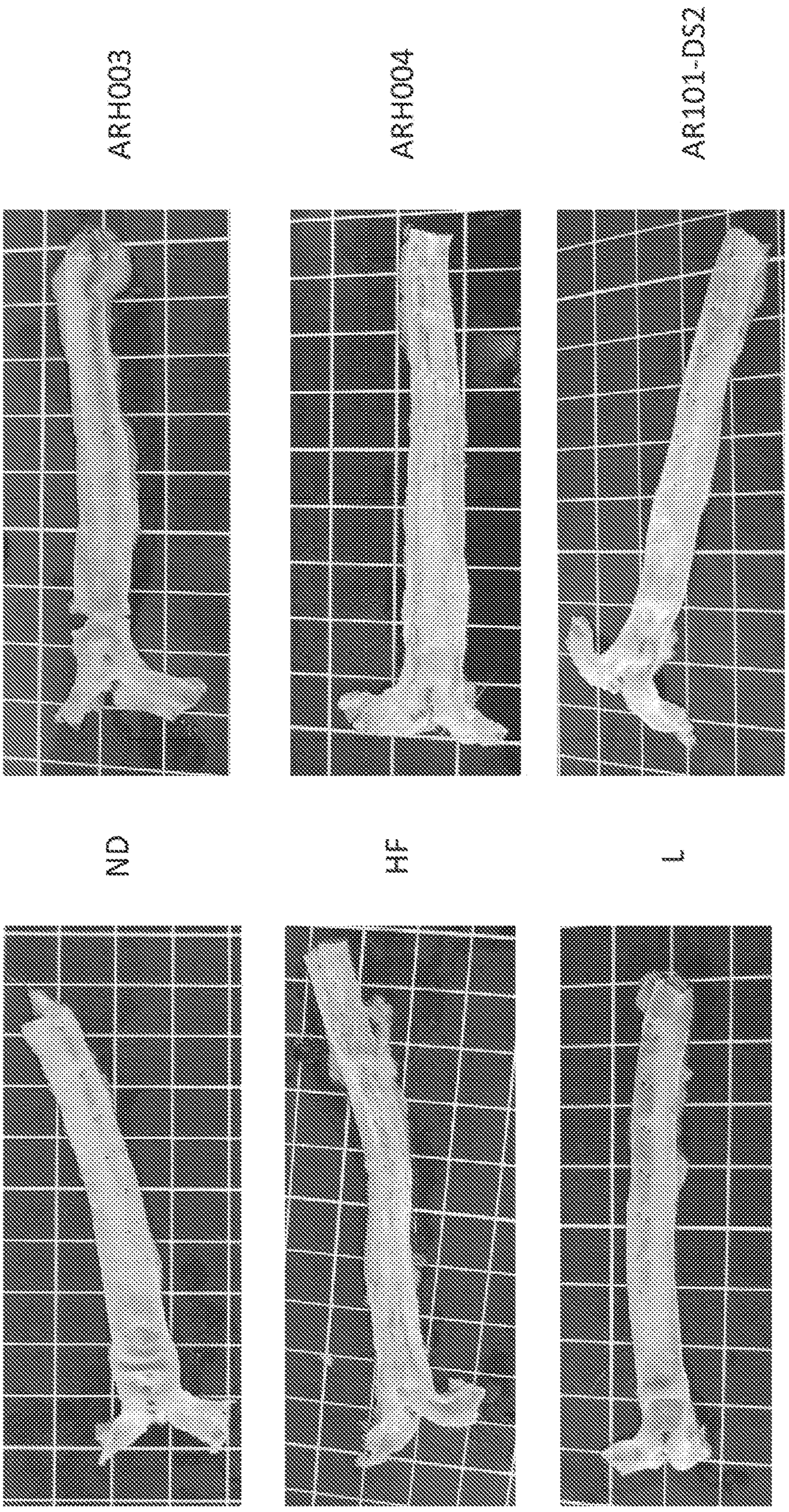
FIG. 24 depict histopathochemical examination of aortic fatty streak lesions in the hypercholesterolemic rabbit model after the 12-week study.
Figure 25:
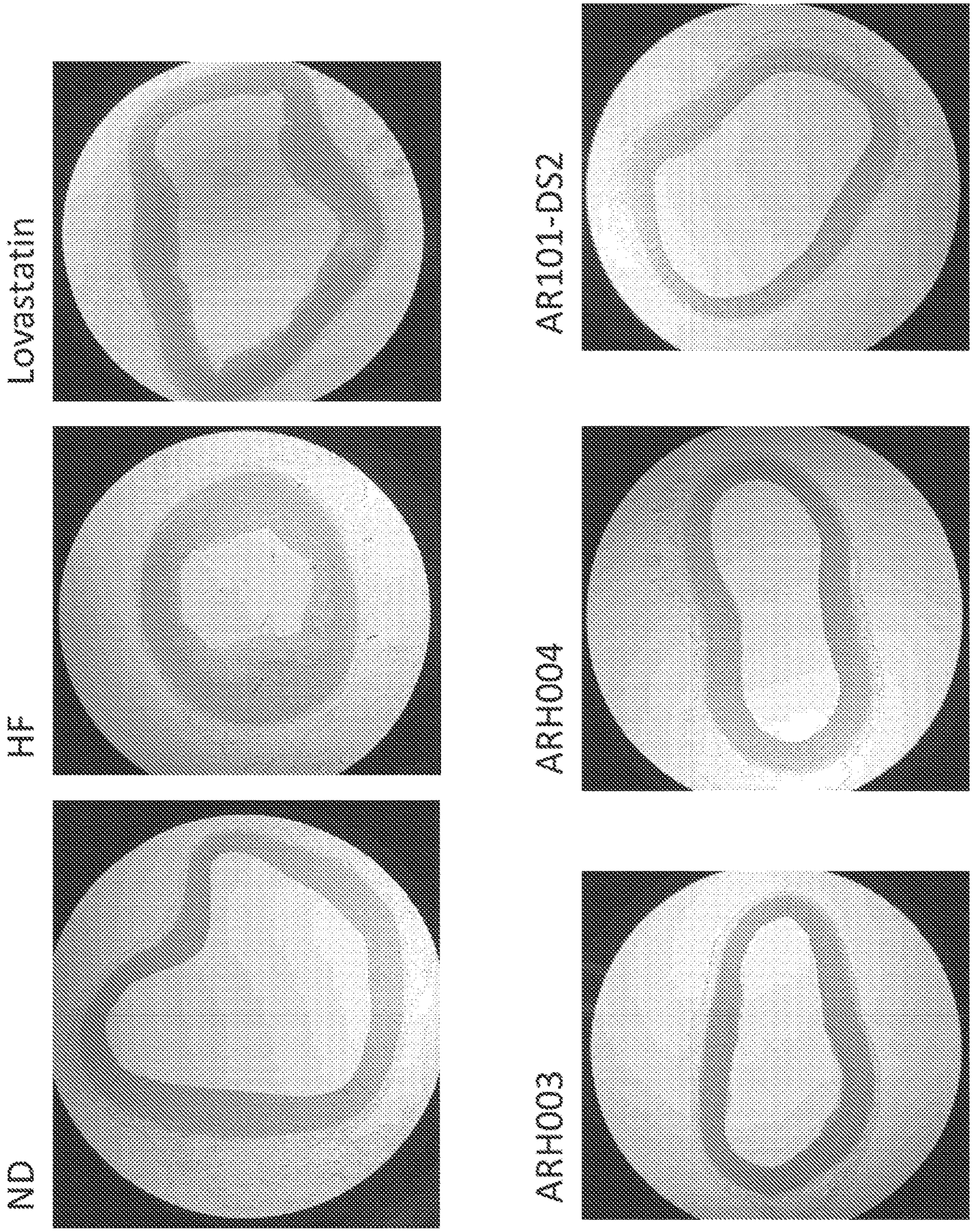
FIG. 25 depicts HE staining of coronary artery sections after sacrifice in each group of rabbits.
Figure 26:
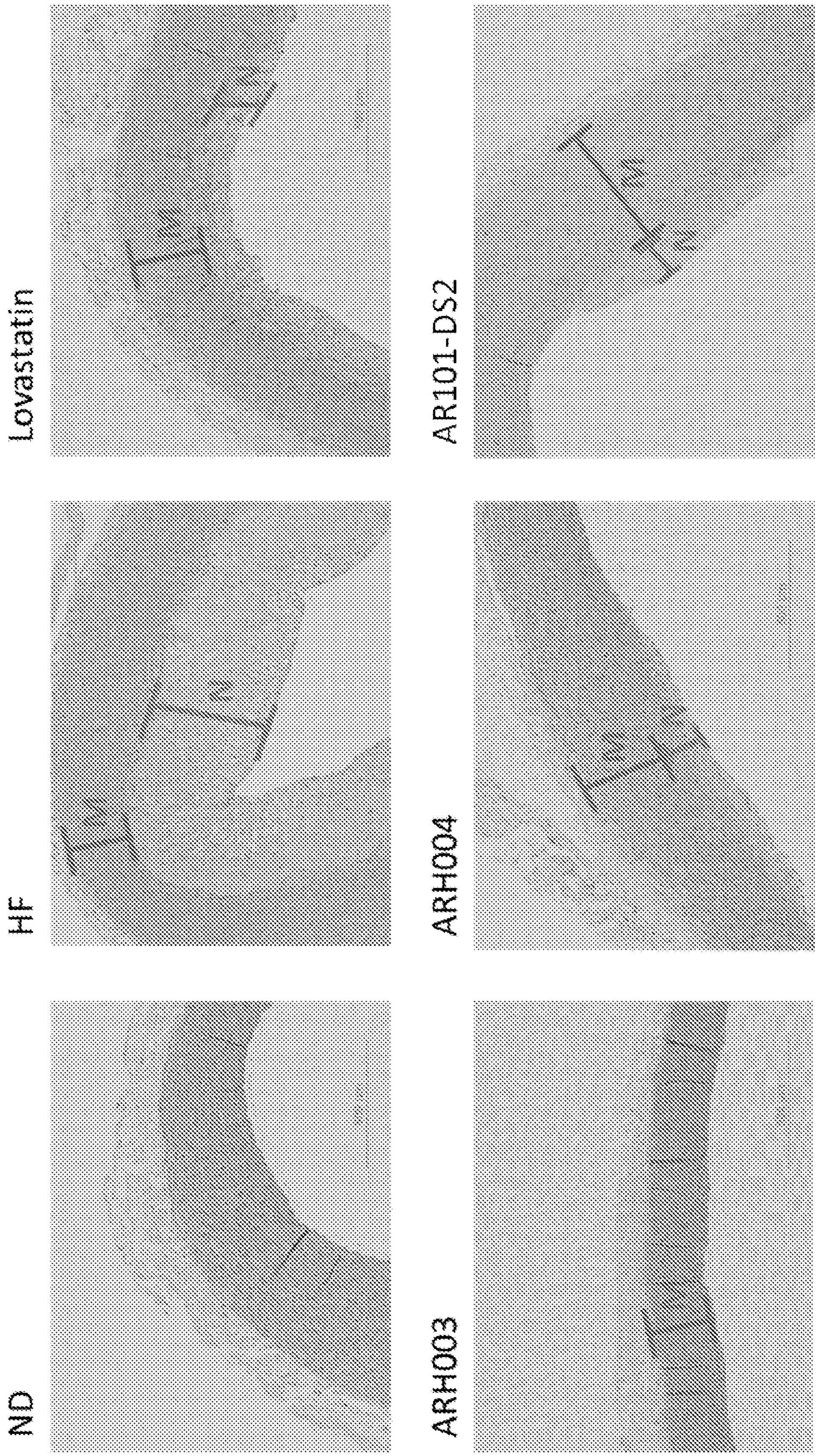
FIG. 26 depicts HE staining of coronary arteries after sacrifice in each group of rabbits. N, neointima layer; M, media layer.
Figure 27:
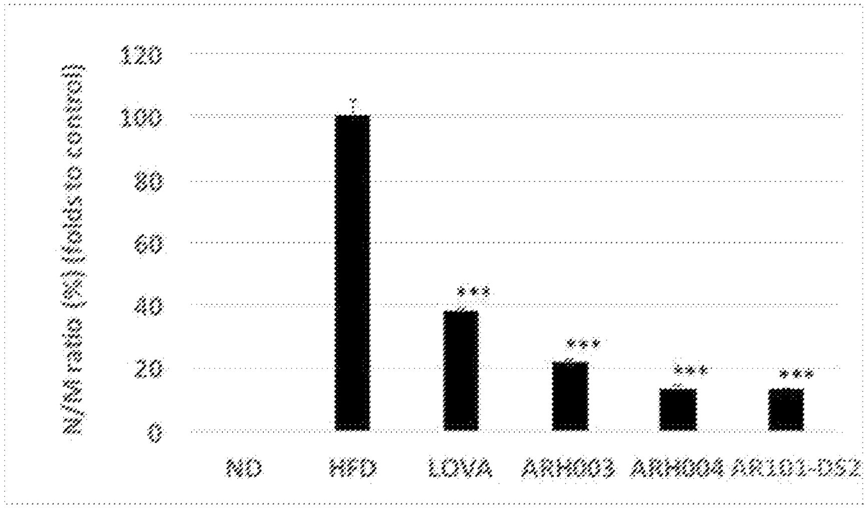
FIG. 27 depicts the manifestation of vascular restenosis is presented as the ratio of neointima-to-media area (N/M ratio) N, neointima layer; M, media layer. *p<0.05, p<0.01, and *p<0.001 compared with RFD group, respectively.
Figure 28:
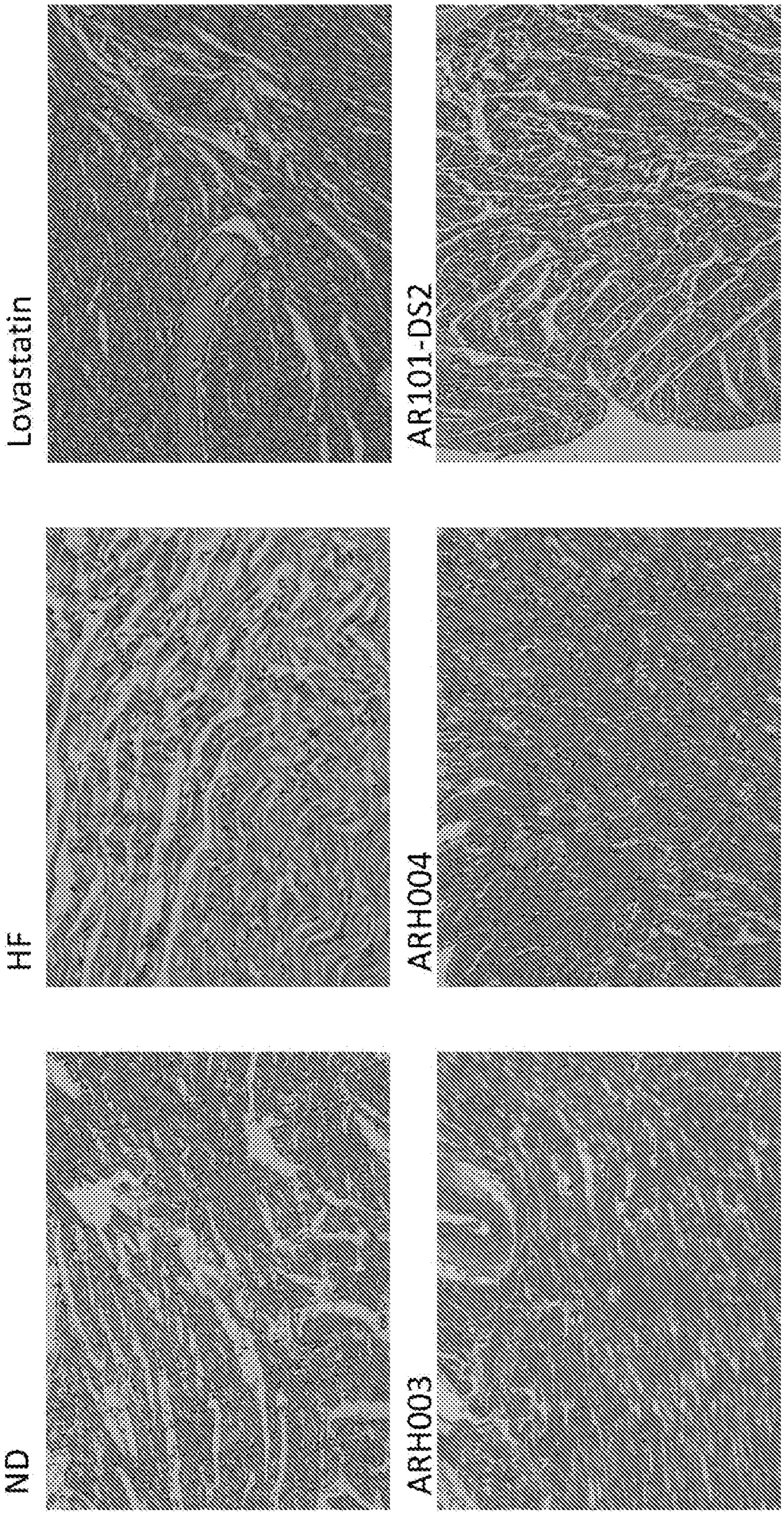
FIG. 28 depicts histopathochemical examination of heart tissues in the hypercholesterolemic rabbit model after the 12-week study.

The aortas are opened longitudinally to expose the intimal surface and rinsed gently with normal saline (see FIGS. 24-26). Aortas are incubated in 2% (w/v) Sudan IV, rinsed with several concentrations (100%, 90%, 80%, 70%, and 60%) of ethanol for 1 min, and then rinsed with pure water. The photographs shown in FIG. 28 are acquired using a digital camera (Nikon D80, Japan) and quantified on an Alpha Imager 2200 documentation system (Alpha Innotech, USA). The progression of the fatty streak lesions is presented as the percentage of the stained area to the total area (FIG. 27).

Method

1. Hydrate the cells or tissue:

i. Use a microscope slide bearing cryosections or rehydrated tissue sections (see Step 12 in Cutting Sections of Paraffin Embedded Tissues) (Fischer et al. 2008) fixed in either alcohol or an aldehyde-based fixative.

ii. Immerse the slide for 30 sec with agitation by hand in H2O.

A rinse in $H_2O$ is important; hematoxylin precipitates with salts and buffers. The staining can be performed after immunohistochemical or hybridization reactions with nonfluorescent detection systems.

2. Dip the slide into a Coplin jar containing Mayer's hematoxylin and agitate for 30 sec.

3. Rinse the slide in $H_2O$ for 1 min.

Estimate the staining intensity at this point, and repeat Steps 2 and 3 if necessary.

4. Stain the slide with 1% eosin Y solution for 10-30 sec with agitation.

5. Dehydrate the sections with two changes of 95% alcohol and two changes of 100% alcohol for 30 sec each.

Some colorimetric substrates dissolve in alcohol.

6. Extract the alcohol with two changes of xylene.

If using plastic slides or staining in plastic culture dishes, do not use xylene or xylene-based mounting media, because they dissolve plastics.

7. Add one or two drops of mounting medium and cover with a coverslip.

If alcohols cannot be used, mount the coverslip with glycerol or other aqueous mounting media.

Reagents

Cells or tissue of interest on microscope slide (see Step 1.i)

Eosin Y (1% aqueous solution; EM Diagnostic Systems)

Ethanol (95%, 100%)

Methanol or Flex alcohols (Richard-Allan Scientific) can be used instead of ethanol (see Step 5).

Hematoxylin, Mayer's (Sigma)

Mayer's hematoxylin is the easiest to use and is compatible with most colorimetric substrates.

Mounting medium (Canada Balsam, Sigma C1795)

Use glycerol or other aqueous mounting media if alcohols cannot be used (see Step 7).

Xylene

Cryosectioning of Liver Tissues

Figure 29:
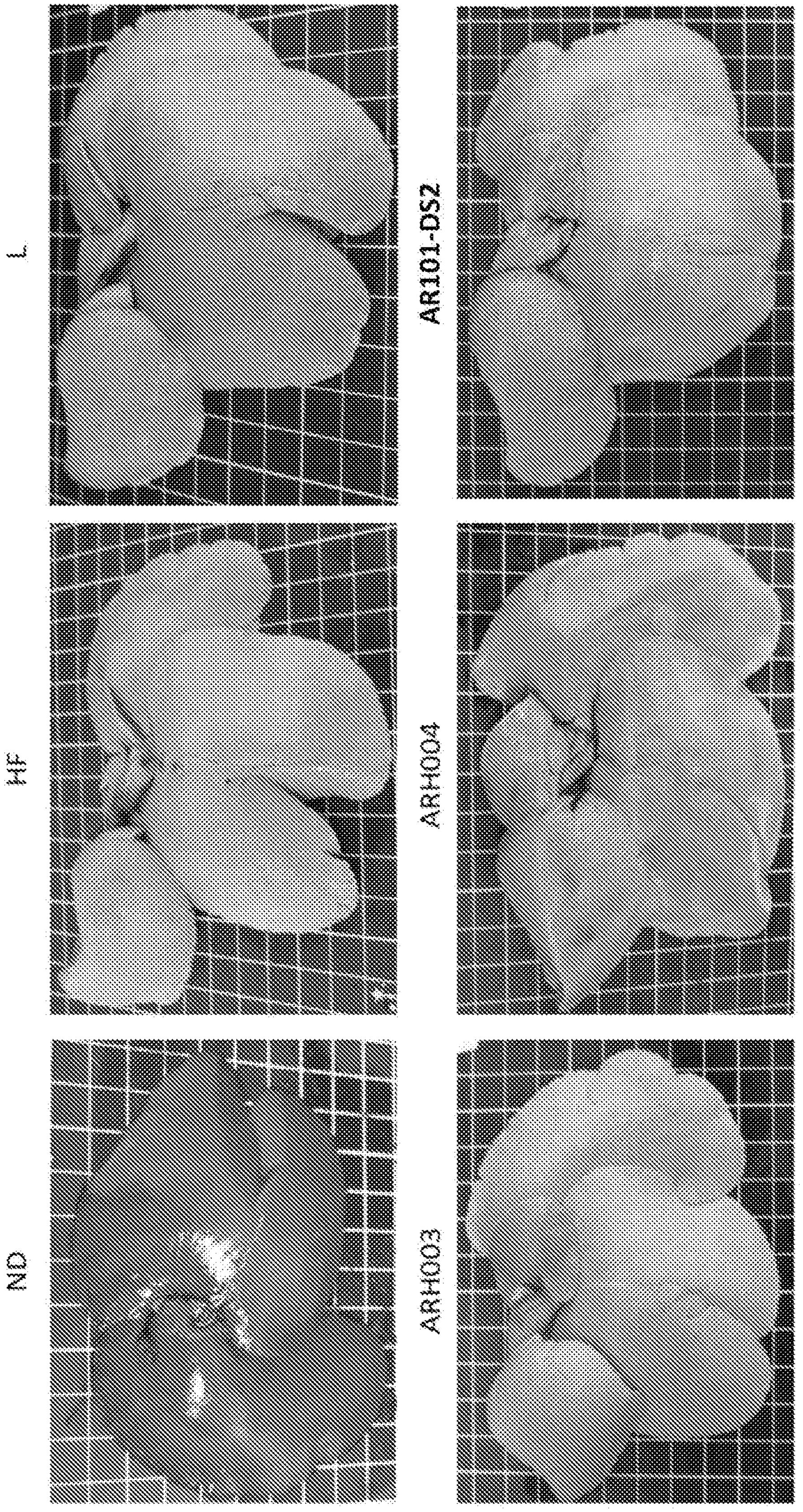
FIG. 29 depicts photographs of liver appearance in the hypercholesterolemic rabbit model after the 12-week study.
Figure 30:
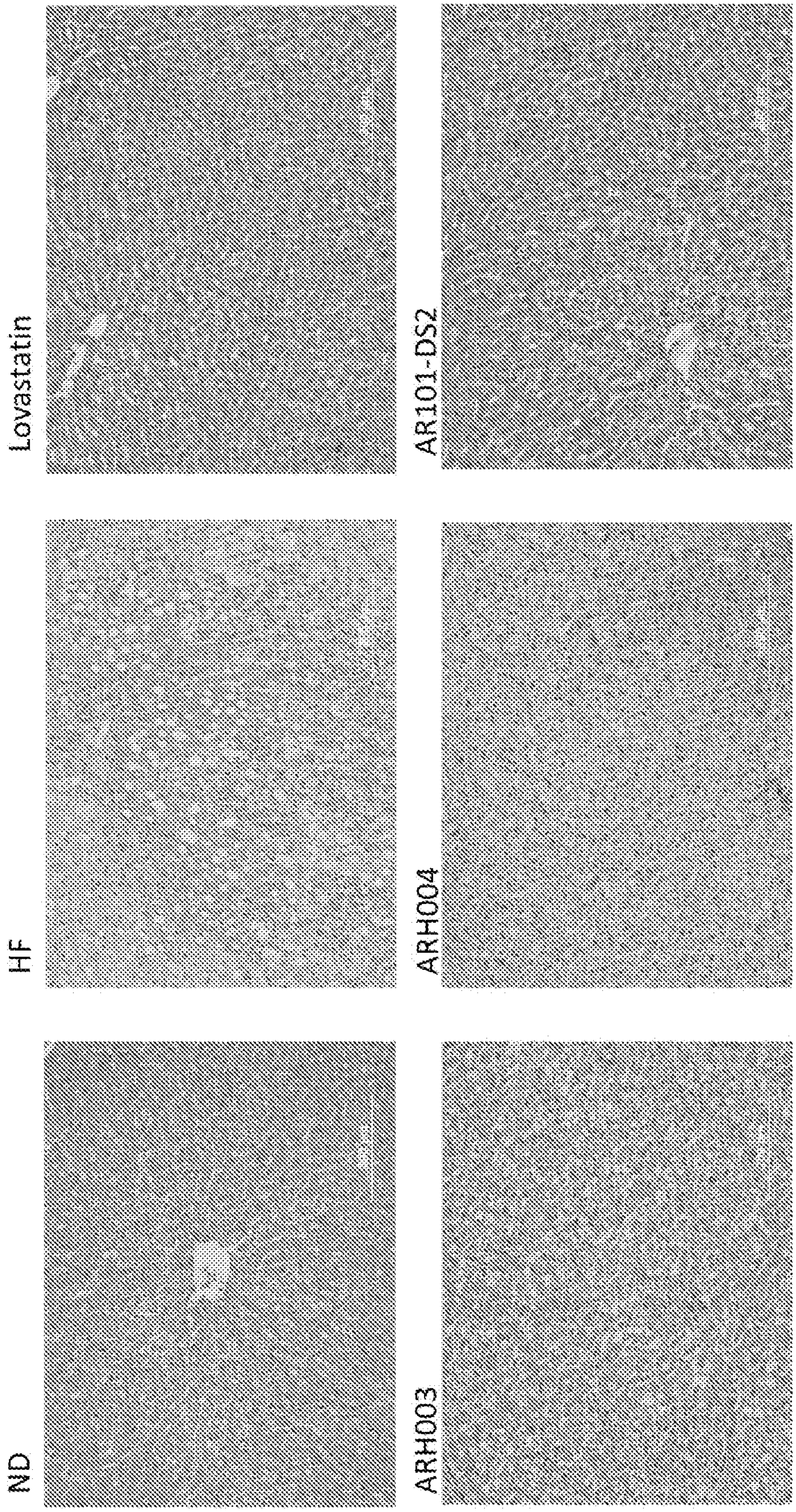
FIG. 30 depicts histopathochemical examination of liver tissues in the hypercholesterolemic rabbit model after the 12-week study.

The rabbit liver tissues (shown in FIG. 29) are perfused with normal saline and fixed in 10% (v/v) formalin-neutralized solution (J.T. Baker, Inc., USA) for 24 hr. Afterward, the tissues are embedded in Tissue Tek OCT Compound (#4583; Sakura Finetek Inc., USA). Embedded tissues are cut into 10 μm thick slices and stained with Sudan IV and hematoxylin (Merck, USA). Briefly, the slices are washed with pure water for 1 min to remove the OCT compound, washed with 50% (v/v) ethanol for 30 sec, and then stained with 2% (w/v) Sudan IV for 1 hr. After further washing with 50% (v/v) ethanol and pure water for 2 min, the slices are counterstained with hematoxylin. Photographs shown in FIG. 30 are acquired using a microscope equipped with a 10-fold magnification Objective and quantified on an Alpha Imager 2200 documentation system (Alpha Innotech, USA). The manifestation of fatty liver progression is presented as the percentage of the area of oil droplets to the total liver tissues (cells).

| | Score of Steatosis | | Score of | Score of |
|---|---|---|---|---|
| Slide No. | Grade | Location | Inflammation | Fibrosis |
| ND1 | 0 | 0 | 0 | 0 |
| ND2 | 0 | 0 | 0 | 0 |
| ND3 | 0 | 0 | 0 | 0 |
| HF1 | 3 | 3 | 2 | 2-3 |
| HF2 | 2 | 1-2 | 1 | 2-3 |
| HF3 | 3 | 2-3 | 1 | 3-4 |
| L1 | 2 | 1 | 2 | 1 |
| L2 | 2 | 1 | 1 | 0 |
| L3 | 0 | 0 | 0 | 0 |
| ARH003-1 | 3 | 2 | 1 | 0 |
| ARH003-2 | 3 | 2 | 1 | 0 |
| ARH003-3 | 2 | 2 | 1 | 0 |
| ARH004-1 | 3 | 2 | 1 | 1 |
| ARH004-2 | 3 | 2 | 0 | 0 |
| ARH004-3 | 3 | 2 | 1 | 0 |
| AR101-DS2-1 | 3 | 2 | 1 | 0 |
| AR101-DS2-2 | 3 | 1 | 2 | 0 |
| AR101-DS2-3 | 1 | 0 | 1 | 0 |

Score of Steatosis
Grade
0': low- to medium-power evaluation of parenchymal involvement <5%
1': 5-33%
2': 33-66%
3': >66%
Location
0': zone 3, centrilobular
1': zone 2, mid-zonal
2': zone 3, periortal
3': panacinar
Score of Fibrosis
0': none
1': mild perisinusoidal or periportal
2': perisinusoidal and portal/periportal
3': bridging fibrosis
4': cirrhosis
Score of Inflammation
0': no foci
1': mild, 2 foci per 200 field
2': moderate, 2-4 foci per 200 field
3': severe, 4 foci per 200 field

EXAMPLE 19

The Protective Effect of *Antrodia camphorata* Extract and Compounds on Bleomycin-Induced Pulmonary Fibrosis in Mice Animals and Treatments Specific pathogen-free ICR mice (males) (body weights 18-22 g) were purchased from the BioLASCO Taiwan Co., Ltd. (Taipei, Taiwan). The animals were housed in Plexiglas cages at a constant temperature of 22±1° C. and a relative humidity of 55±5% on a 12 h dark-light cycle for at least 2 weeks before the experiment. Animals were provided food and water ad libitum. All experimental procedures were performed according to the guidelines of the Institutional Animal Ethics Committee, and the protocol was approved by the Committee for the Purpose of Control and Supervision of Experiments on Animals.

BLM-Induced PF in Mice

Mice were divided into fifth groups with 5 animals per group according to body weight: control group, BLM group, BLM+DEX group (7.5 mg/kg), BLM+ACH dosage group (50 mg/kg), and BLM+ACM dosage group (2.5 mg/kg), BLM+ACH dosage group (50 mg/kg), and BLM+ACM dosage group (25 mg/kg) BLM+AH dosage group (50 mg/kg), and BLM+AM dosage group (25 mg/kg) BLM+BH dosage group (50 mg/kg), and BLM+BM dosage group (25 mg/kg) BLM+CH dosage group (50 mg/kg), and BLM+CM dosage group (25 mg/kg) BLM+DH dosage group (50 mg/kg), and BLM+DM dosage group (25 mg/kg) BLM+EH dosage group (50 mg/kg), and BLM+EM dosage group (25 mg/kg) BLM. Pulmonary fibrosis (PF) was established in mice via a single intratracheal administration of BLM at 7.5 mg/kg mg/kg body weight. Different doses of samples were intragastrically administered daily for 21 days after BLM injury, and DEX was used as the positive control. Control and model groups received an equal volume of vehicle (0.9% NaCl) using the same schedule and route of administration.

Mouse body weights were recorded daily. Mice were sacrificed on the 21th day using excess chloral hydrate hydrochloride anesthesia. Blood was obtained for ELISA analyses, and whole lungs were removed and weighed. The right lungs were fixed in 10% formalin, dehydrated, and embedded in paraffin The left lungs were used to determine hydroxyproline. The pulmonary coefficient was calculated using the following equation: lung weight/body weight× 100%

Experimental Design

Male C57BL/6 mice were randomly divided into the following eight groups (n=6):

1. Group control;
2. Group II: mice received single intraperitoneal injection of BLM (7.5 mg/kg BW)
3. Group III: single dose (ACH, 0.5 g/kg)
4. Group IV: Single dose (ACM, 1.0 g/kg)
5. Group V: purified AR101-DS1 (50 mg/kg)
6. Group VI: purified AR101-DS1 (25 mg/kg)
7. Group VII: purified AR101-DS2 (50 mg/kg)
8. Group VIII: purified AR101-DS2 (25 mg/kg)
7. Group VII: purified AR101-DS4 (50 mg/kg)
8. Group VIII: purified AR101-DS4 (25 mg/kg)
7. Group VII: purified AR100-DS1 (50 mg/kg)
8. Group VIII: purified AR100-DS1 (25 m/kg)
7. Group VII: purified ARH013-RA1 (50 mg/kg)
8. Group VIII: purified ARH013-RA1 (25 mg/kg)

Sampling of BALF

Under anaesthesia, BALF was performed four times through a tracheal cannula with 0.7 mL of saline. In each mouse examined, ~2.5 mL (90%) of BAL fluid (BALE) was recovered. The supernatants of BALF were stored at −80° C. until used.

Lung Histopathology

The anterior portion of the right lung from each mouse was fixed in 10% formaldehyde phosphate buffer, embedded in paraffin, cut into 5 μm sections, and then treated with an hematoxylin and eosin (H&E) stain for histological examination under the light microscopy (Nikon, ECLIPSE, TS100, Tokyo, Japan). Images were captured with a digital camera (NIS-Elements D 2.30, SP4, Build 387) at an original magnification of 400×.

Assay of Hydroxyproline

The contents of hydroxyproline were analyzed in lung tissue following the instruction of hydroxyproline assay kit (Biosource International Inc., Sunnyvale, CA, USA), The pulmonary tissues of mice were ground and homogenized with 1 ml of 6 rout potassium chloride solution, hydrolyzed at 95° C. for 5 hours, and the pH value was adjusted to 6.0-6.8, According to the instructions, the corresponding reagents were added to the reaction system and mixed thoroughly and then incubated for 15 minutes at 60° C. After cooling, the supernatants were collected after centrifuging at 3500 rpm for 10 minutes. The absorbance value of the supernatant from the samples was measured at 550 nm by a spectrophotometer and calculated for the contents of hydroxyproline on each group.

TNF-α, IL-6, and IL-1β Cytokines in Serum

The serum concentration of the pro-inflammatory cytokines (i.e. tumor necrosis factor-α (TNF-α), interleukin-6 (IL-6), and IL-1β) in serum were assessed with relevant enzyme-linked immunosorbent assay (ELISA) kits (Biosource International Inc., Sunnyvale, CA, USA), based on the manufacturer's instructions.

Myeloperoxidase (MPO) Assay

The pulmonary MPO activity was a reliable index for estimating the infiltration of inflammatory cells in lungs. The lung tissues were homogenized and the MPO levels were detected with the kits according to manufacturer's instruction.

Histopathological Analyses

The right lungs were embedded in paraffin wax, fixed in 10% formalin, and processed into sections. The sections were stained with haematoxylin and eosin (H&E) or subjected to Masson's trichrome staining.

Statistical Analysis

Data obtained from animal experiments were expressed as the means and standard errors of the means (±S.E.M.). Student's t-test were used to examine the differences among multiple groups or between two groups. Statistical significance is expressed as *p<0.05, p<0.01 and *p<0.001.

Figure 31:
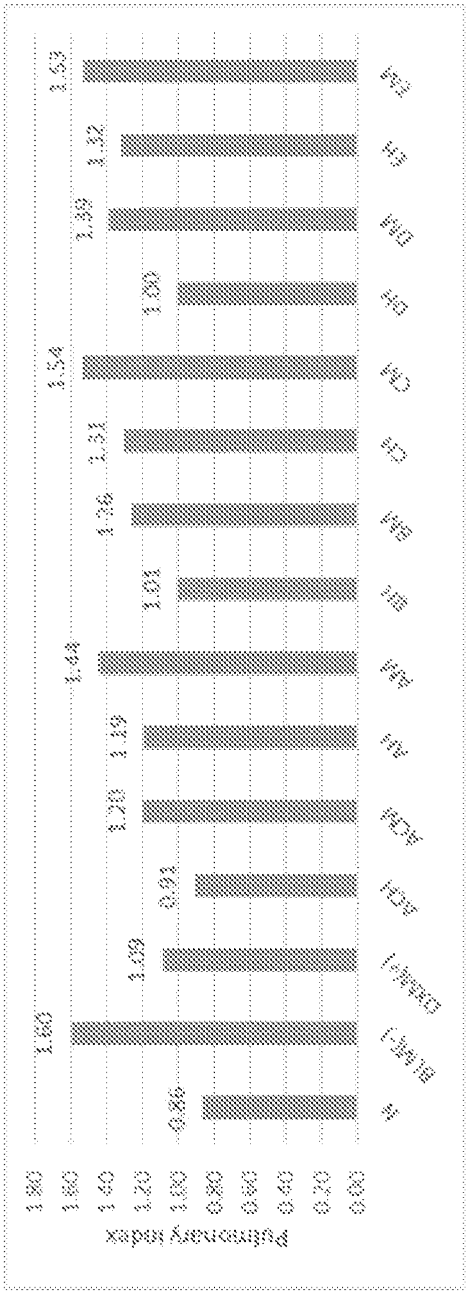
FIG. 31 depicts the animal's body weight and lung weight.

At the end point of the entire experiment, the animal's body weight and lung weight were recorded. Compared with control animals, the body weight changes of bleomycin (BLM)-administered animals were significantly reduced. Compared with other experimental groups, the lung index [(lung weight/body weight)×100] showed a significant increase in bleomycin-administered animals (Table 1 and FIG. 31). There was a significant decrease in the lung index of ACH, BH and DH.

TABLE 1

Lung index of A. camphorata Extract and Compounds on bleomycin-induced lung fibers.

| | Initial body mass/g | Final body mass/g | Pulmonary mass/g | Pulmonary index |
|---|---|---|---|---|
| Normal | 34.18 ± 0.39 | 39.73 ± 0.38 | 0.34 ± 0.01 | 0.86 ± 0.02 |
| BLM | 34.28 ± 0.39 | 35.45 ± 0.28 | 0.57 ± 0.01 | 1.60 ± 0.02### |
| DEX | 34.24 ± 0.5 | 38.50 ± 0.22 | 0.42 ± 0.01 | 1.09 ± 0.02*** |
| ACH (1.0 g/kg) | 34.28 ± 0.44 | 39.48 ± 0.24 | 0.36 ± 0.01 | 0.91 ± 0.02** |
| ACM (0.5 g/kg) | 34.35 ± 0.45 | 38.42 ± 0.27 | 0.46 ± 0.01 | 1.20 ± 0.02*** |
| AH(AR101-DS1) (50 mg/kg) | 34.22 ± 0.39 | 39.02 ± 0.37 | 0.46 ± 0.01 | 1.19 ± 0.01** |
| AM(AR101-DS1) (25 mg/kg) | 34.35 ± 0.48 | 36.45 ± 0.28 | 0.52 ± 0.01 | 1.44 ± 0.04*** |
| BH(AR101-DS2) (50 mg/kg) | 34.44 ± 0.35 | 39.7 ± 0.21 | 0.39 ± 0.01 | 1.01 ± 0.02** |
| BM(AR101-DS2) (25 mg/kg) | 34.64 ± 0.36 | 37.91 ± 0.30 | 0.48 ± 0.01 | 1.26 ± 0.03*** |
| CH(AR101-DS4) (50 mg/kg) | 34.50 ± 0.37 | 37.47 ± 0.22 | 0.49 ± 0.01 | 1.31 ± 0.01** |
| CM(AR101-DS4) (25 mg/kg) | 34.52 ± 0.29 | 36.44 ± 0.28 | 0.52 ± 0.01 | 1.54 ± 0.04* |
| DH(AR100-DS1) (50 mg/kg) | 34.43 ± 0.25 | 39.12 ± 0.30 | 0.39 ± 0.01 | 1.00 ± 0.02** |
| DM(AR100-DS1) (25 mg/kg) | 34.50 ± 0.33 | 37.33 ± 0.25 | 0.52 ± 0.02 | 1.39 ± 0.06*** |
| EH(ARH013-RA1) (50 mg/kg) | 34.28 ± 0.29 | 37.00 ± 0.42 | 0.49 ± 0.02 | 1.32 ± 0.06** |
| EM(ARH013-RA1) (25 mg/kg) | 34.44 ± 0.31 | 35.86 ± 0.25 | 0.55 ± 0.01 | 1.53 ± 0.03** |

EXAMPLE 20

Figure 32:
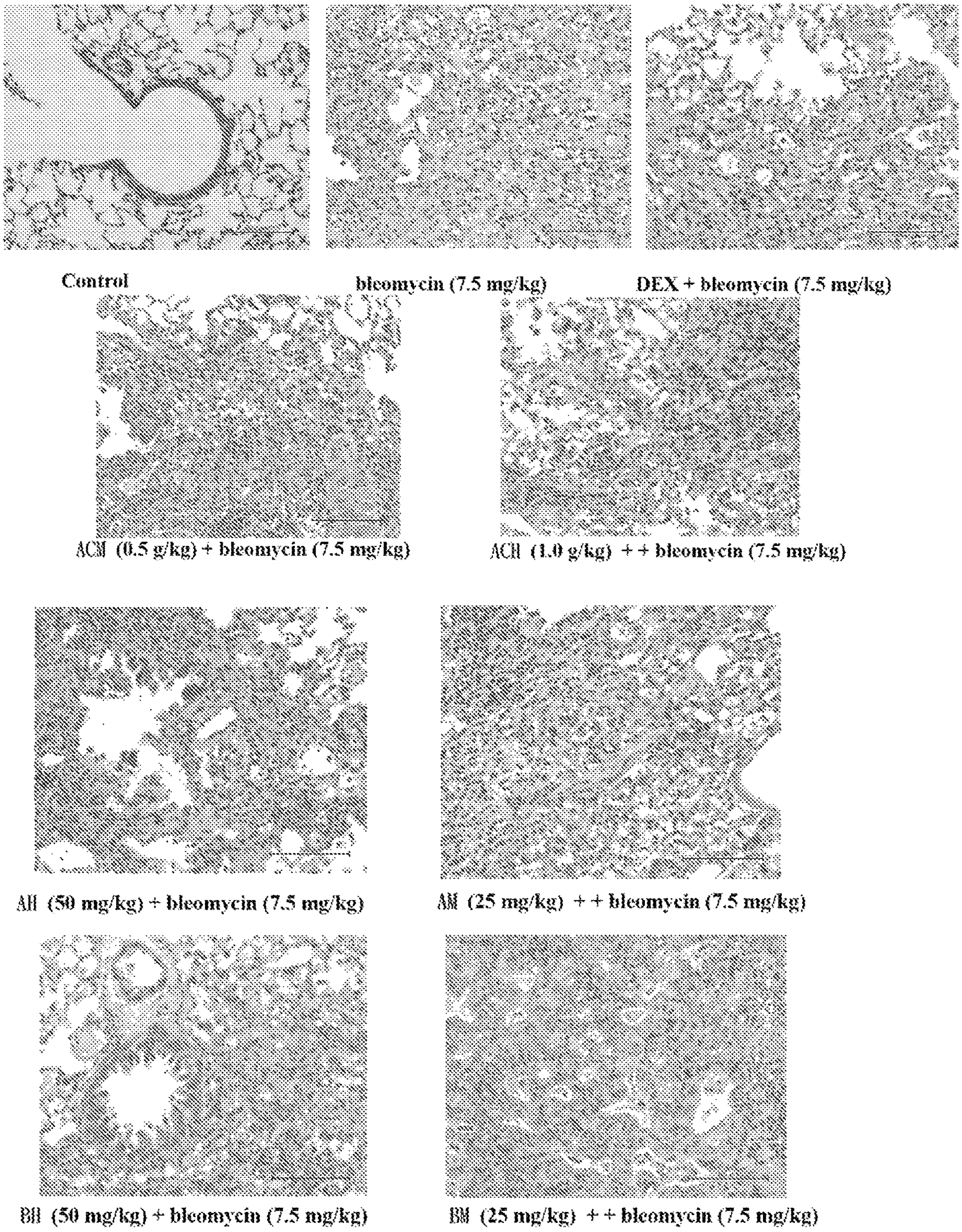
FIG. 32 depicts histopathological changes of the lungs in bleomycin-induced lung fibrosis in mice.
Figure 32:
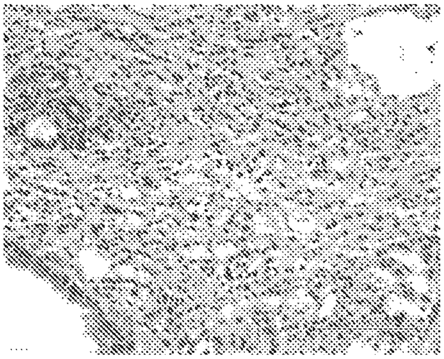
Figure 32:
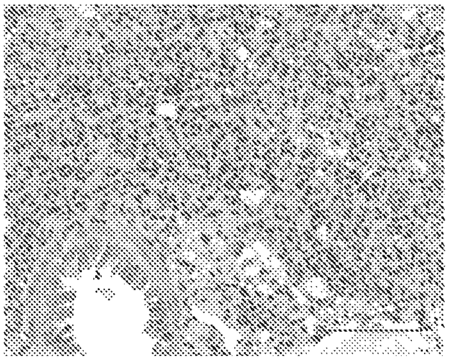
Figure 32:
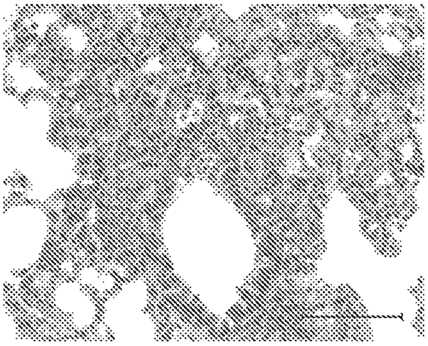
Figure 32:
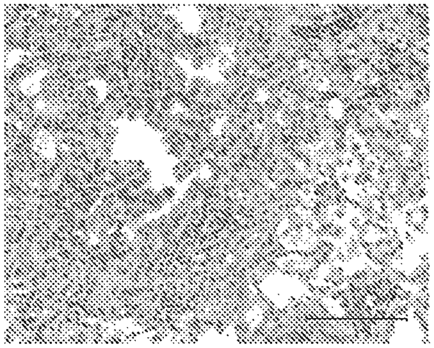
Figure 32:
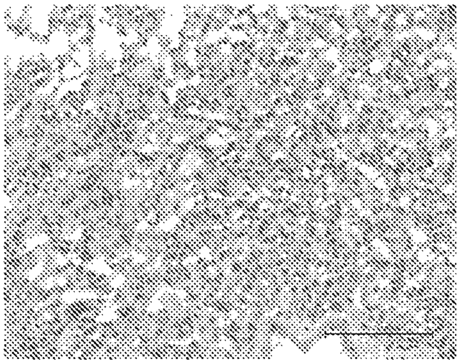
Figure 32:
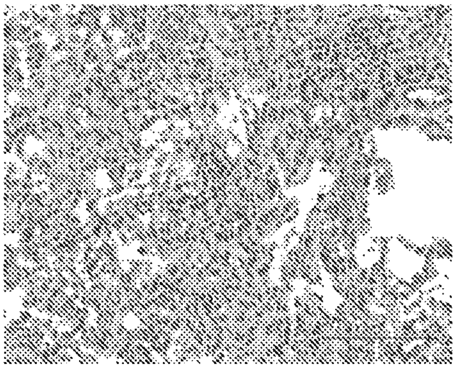
Figure 33:
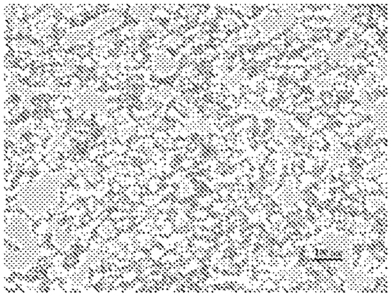
FIG. 33 depicts Masson's Trichrome staining of the lung in bleomycin-induced lung fibrosis in mice.
Figure 33:
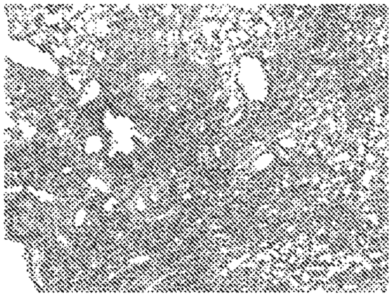
Figure 33:
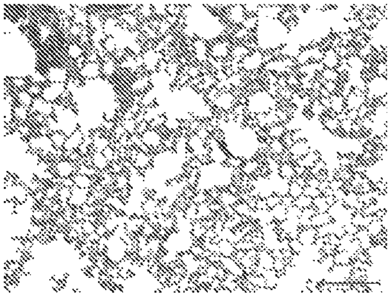
Figure 33:
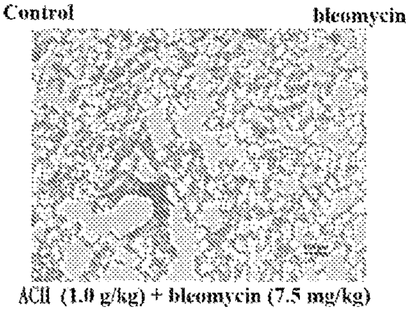
Figure 33:
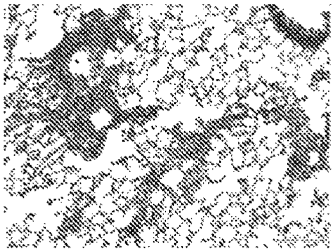
Figure 33:
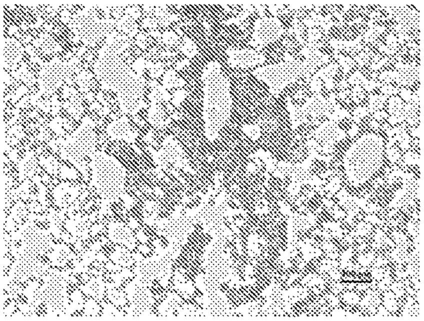
Figure 33:
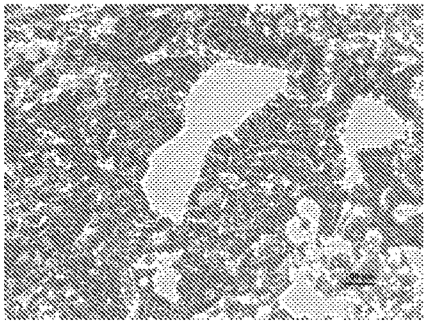
Figure 33:
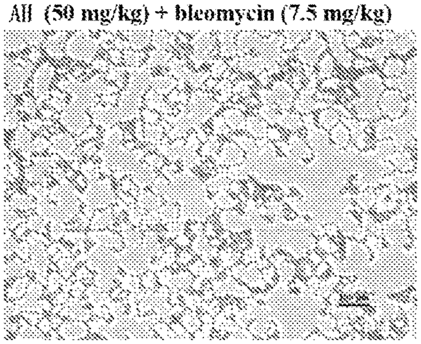
Figure 33:
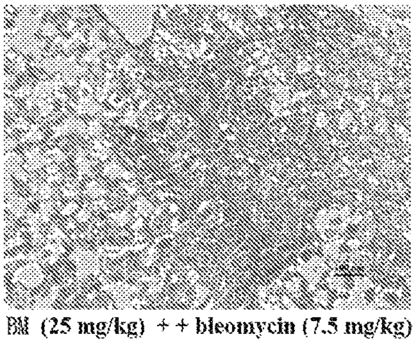
Figure 33:
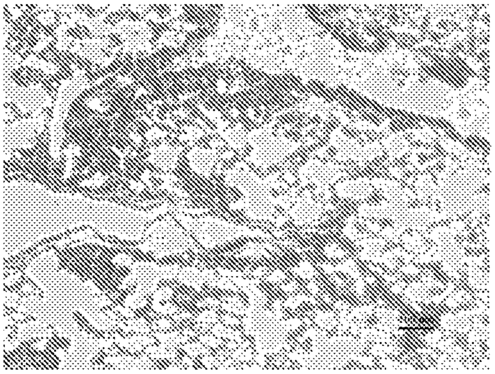
Figure 33:
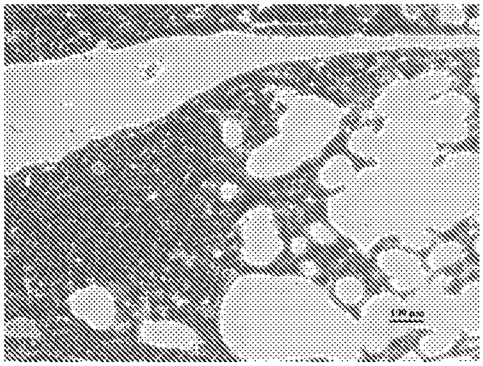
Figure 33:
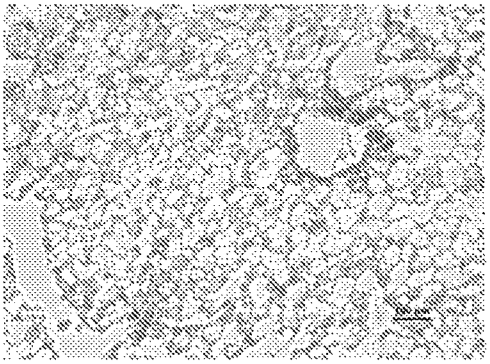
Figure 33:
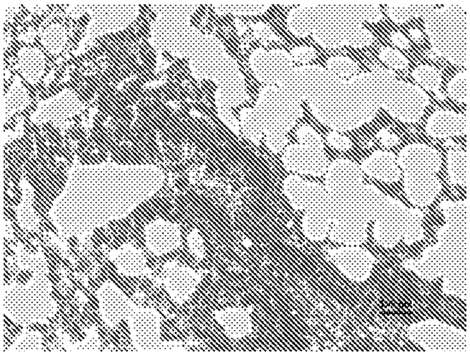
Figure 33:
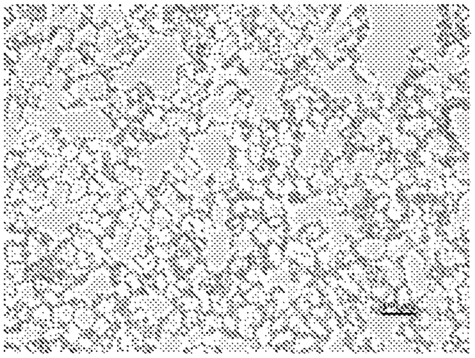
Figure 33:
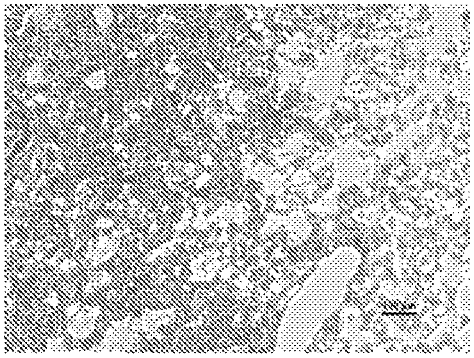

*Antrodia camphorata* Extract and Compounds Reduced Lung Dysfunction and Histopathological Changes in BLM-Induced Mice We evaluated the histopathological lung alterations in mice for exploring the therapeutic effect of *A. camphorata* extract and compounds. Inflammatory infiltration and integrity of organizational structures were observed by H&E staining (FIG. 32); the fibrosis degree of lung tissue was performed by Masson staining (FIG. 33). The control group demonstrated some histological findings such as a thin alveolar wall, intact alveolar structure, normal alveolar septum, and less inflammatory cells infiltration in the pulmonary mesenchyme. After 21 days of BIM administration, alveolar edema, a significant increase in septum width and increased inflammatory cells infiltration were Observed. Administration of *A. camphorata* extract and compounds ameliorated the inflammatory infiltration and the damaged structure in lung tissue as compared to that of the BLM group.

Masson staining extensive stained blue in the lung tissue and septum after 21-day post BLM administration, suggesting a severe degree of pulmonary fibrosis in BLM group than the normal group. After *A. camphorata* extract and compounds treatment, the blue area was decreased, and the fibrosis degree was alleviated. At 21 days after BLM modeling, the scores of alveolitis and fibrosis were significantly decreased after *A. camphorata* extract and compounds therapy. The above results suggested that *A. camphorata* extract and compounds alleviated the degree of inflammation and fibrosis in the lungs of mice with pulmonary fibrosis.

EXAMPLE 21

Pulmonary Fibrotic Markers

Figure 34:
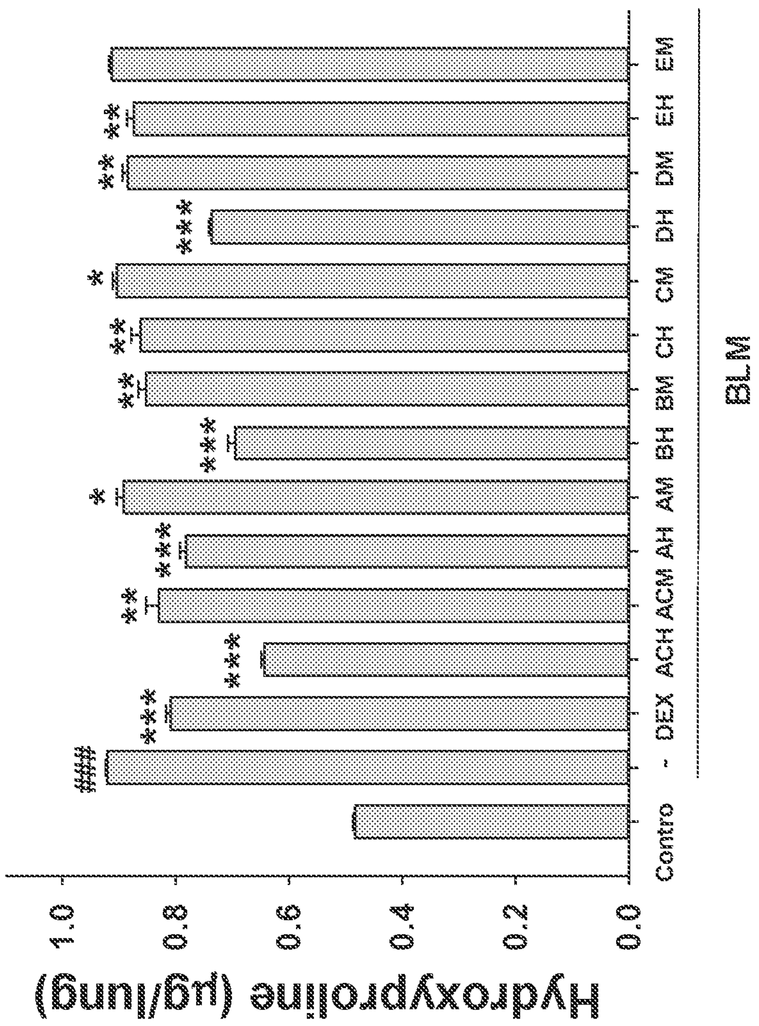
FIG. 34 depicts the effects of *A. camphorata* Extract and Compounds on hydroxyproline content in pulmonary damage of mice induced by bleomycin.

Hydroxyproline content is an important index for collagen deposition in the lung tissue. To quantify the extent of pulmonary fibrosis, the hydroxyproline content in lung tissue was measured in each group and is shown in FIG. 34. BLM obviously increased HP content ($p<0.001$) compared with the control group. *A. camphorata* Extract (1.0 g/kg) and ATI, BH and DH reduced lung HP significant recovery ($p<0.001$).

EXAMPLE 22

Figure 35A:
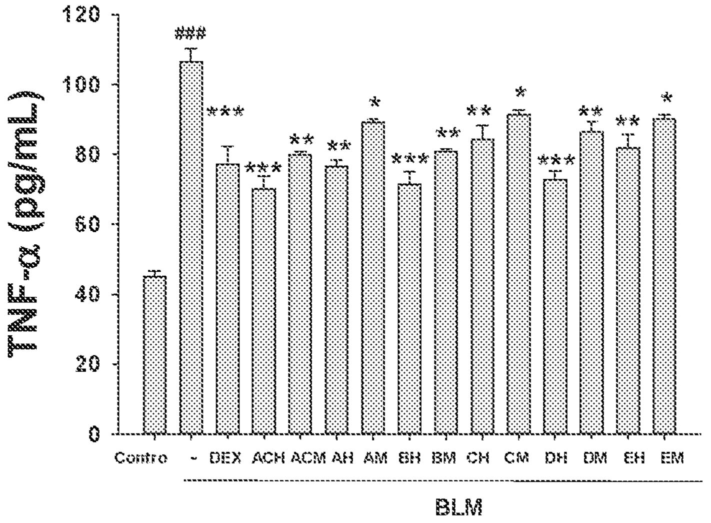
FIG. 35 depict *A. camphorata* Extract and compounds regulated (A) TNF-α, (B) 1β, (C) IL6 (D) and TGF-β(E) in BALF.
Figure 35B:
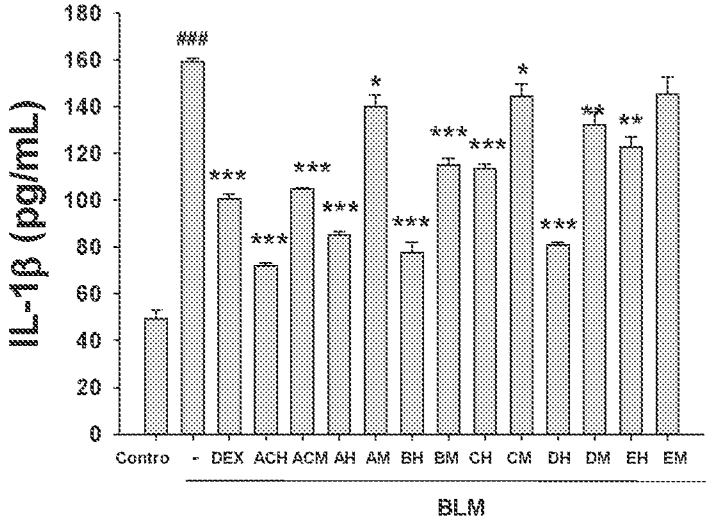
Figure 35C:
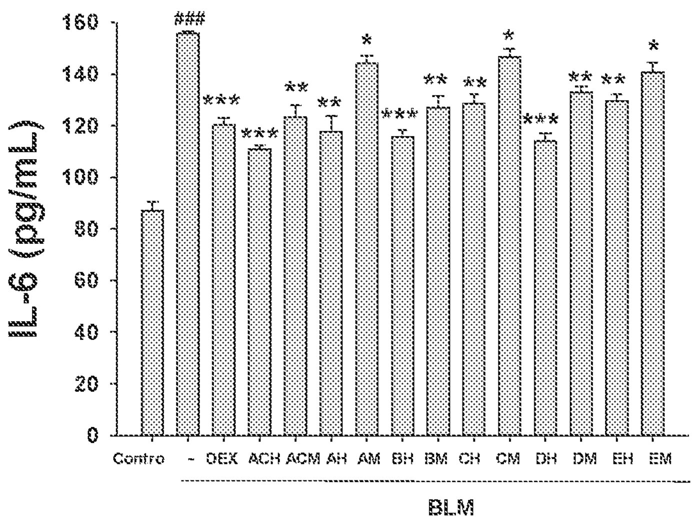
Figure 35D:
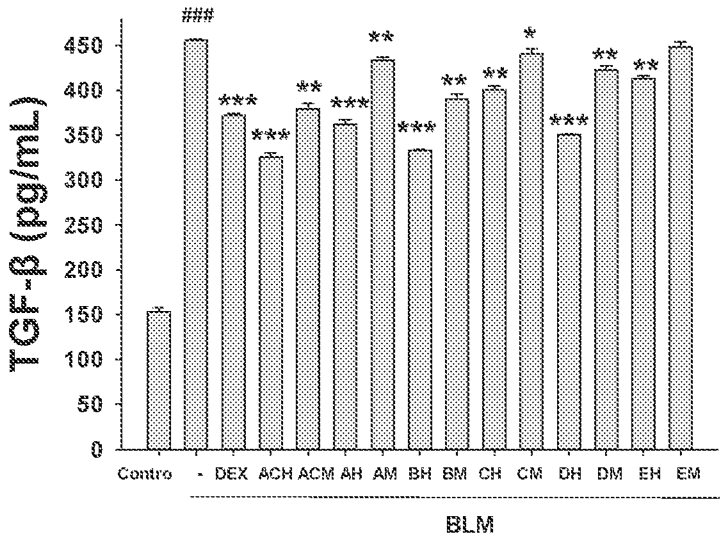

*Antrodia camphorata* Extract and Compounds Alerted the Bleomycin-Induced Changes in Pro-Inflammatory Cytokines Evaluation of proinflammatory cytokine TNF-$\alpha$, IL-1$\beta$, IL-6 and TGF-$\beta$ levels in serum were performed by ELISA. BEM-treated kidney injury mice had significantly increased NO, TNF-$\alpha$, IL-1$\beta$, and IL-6 levels in serum, compared to the control group (FIGS. 35A-34E, respectively). treatment with *A. camphorata* Extract at doses of 1.0 g/kg and compounds (BH and DH) significantly improved necrosis and inflammatory infiltrating cells in the lung tissue treatment improved TNF-$\alpha$, IL-1$\beta$, IL-6 and TGF-$\beta$ production after BLM challenge ($p<0.001$).

EXAMPLE 23

Effects of *A. camphorata* Extract and Compounds on Lung MPO Activity

Figure 36:
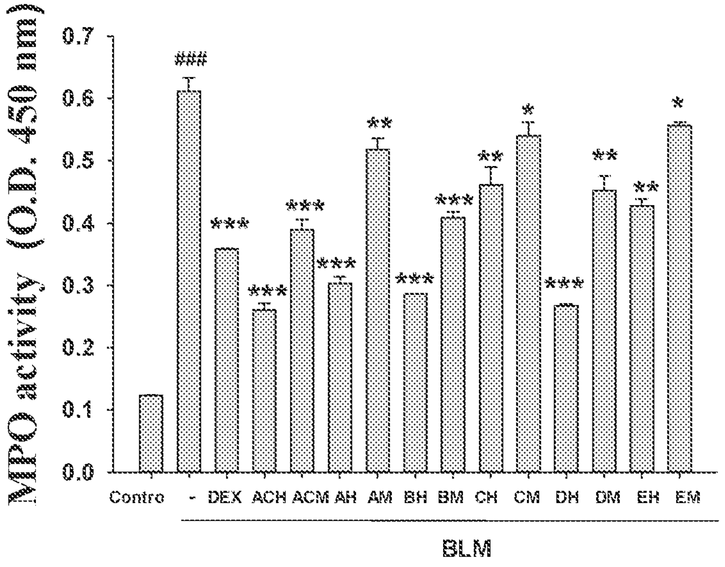
FIG. 36 depicts the effects of *A. camphorata* Extract and compounds regulated on lung MPO activity in BLM-induced mice.

As depicted in FIG. 36, there was a remarkable increase of the MPO level in response to BLM challenge compared with that in control group ($p<0.01$). On the contrary, the administration of both *A. camphorata* extract, AH, BH, DH and Dex evidently suppressed the MPO activities compared with that in BLM group ($p<0.001$), which exerted stronger effect than that in *A. camphorata* extract and compounds group ($p<0.05$) (FIG. 36).

What is claimed is:

1. A method of treating a fibrotic condition, comprising administering an effective amount of an ethanol extract of *Anisomeles indica* to a subject in need thereof, wherein the fibrotic condition is renal fibrosis, vascular fibrosis, pulmonary fibrosis, or benign prostatic hyperplasia.

2. The method of claim 1, wherein the ethanol extract of *Anisomeles indica* is obtained from an organic eluent by introducing an ethanol extract of *Anisomeles indica* into a normal phase chromatography column, and eluting the column with hexane/ethyl acetate/methanol.

3. The method of claim 1, wherein the ethanol extract of *Anisomeles indica* further alleviates renal dysfunction and renal injury.

4. The method of claim 1, wherein the ethanol extract of *Anisomeles indica* further alleviates non-alcoholic steatohepatitis (NASH), non-alcoholic fatty liver disease (NAFLD), and inflammation, vacuolation and necrosis in liver.

* * * * *